US008604162B2

(12) United States Patent
Wakamiya et al.

(10) Patent No.: US 8,604,162 B2
(45) Date of Patent: Dec. 10, 2013

(54) COLLECTIN

(75) Inventors: Nobutaka Wakamiya, Asahikawa (JP); Hiroyuki Keshi, Osaka (JP); Katsuki Ohtani, Hokkaido (JP); Takashi Sakamoto, Nara (JP); Yuichiro Kishi, Wakayama (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 393 days.

(21) Appl. No.: 13/160,091

(22) Filed: Jun. 14, 2011

(65) Prior Publication Data

US 2013/0150565 A1   Jun. 13, 2013

Related U.S. Application Data

(60) Division of application No. 12/334,052, filed on Dec. 12, 2008, now Pat. No. 7,985,833, which is a continuation of application No. 10/258,105, filed as application No. PCT/JP01/03468 on Apr. 23, 2001, now abandoned.

(30) Foreign Application Priority Data

Apr. 21, 2000 (JP) ................................. 2000-120358

(51) Int. Cl.
C07K 14/00 (2006.01)
(52) U.S. Cl.
USPC .............................................. 530/300; 514/2
(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 5,270,199 A | 12/1993 | Ezekowitz | |
| 6,787,639 B1 | 9/2004 | Wakamiya | |

FOREIGN PATENT DOCUMENTS

| | | |
|---|---|---|
| JP | 6336786 | 2/1988 |
| JP | 04330295 | 11/1992 |
| JP | 05304989 | 11/1993 |
| JP | 6181767 | 7/1994 |
| JP | 10237611 | 8/1998 |
| JP | 11206377 | 8/1999 |
| WO | WO-89/01519 | 2/1989 |
| WO | WO-89/01783 | 3/1989 |
| WO | WO-89/01974 | 3/1989 |
| WO | WO-91/06649 | 5/1991 |
| WO | WO-91/09967 | 7/1991 |
| WO | WO-91/16927 | 11/1991 |
| WO | WO-91/16928 | 11/1991 |
| WO | WO-92/01059 | 1/1992 |
| WO | WO-92/22653 | 12/1992 |
| WO | WO-93/06231 | 4/1993 |
| WO | WO-94/04679 | 3/1994 |
| WO | WO-94/13805 | 6/1994 |
| WO | WO-94/29351 | 12/1994 |
| WO | WO-98/37200 | 8/1998 |
| WO | WO-98/45332 | 10/1998 |
| WO | WO-98/55614 | 12/1998 |
| WO | WO-99/63088 | 12/1999 |
| WO | WO-00/18922 | 4/2000 |
| WO | WO-00/53755 | 9/2000 |
| WO | WO-00/73454 | 12/2000 |
| WO | WO 02/08284 A2 | 1/2002 |
| WO | WO 02/08284 A3 | 1/2002 |

OTHER PUBLICATIONS

Bruck et al., One-Step Purification of Mouse Monoclonal Antibodies from Ascitic Fluid by DEAE Affi-Gel Blue Chromatography, *J. Immuno. Methods*,53: 313-9 (1982).
Chirgwin et al., Isolation of Biologically Active Ribonucleic Acid from Sources Enriched in Ribonuclease, *Biochemistry*, 18: 5294-9 (1979).
Eda et al., Characterization of Truncated Human Mannan-Binding Protein (MBP) Expressed in *Escherichia col*, *Biosci. Biotechnol. Biochem.*, 62: 1326-31 (1998).
Epstein et. al., The Collectins in Innate Immunity, *Curr. Opin. Immunol.*, 8:29-35 (1996).
Ezekowitz et al., A Human Mannose-binding Protein is an acute-phase Reactant That Shares Sequence Homology with Other Vertebrate Lectins., *J. Exp. Med.*, 167: 1034-46 (1988).
Floros et al., Genetics of the Hydrophilic Surfactant Proteins A and D., *Biochimica et Biophysica Acta*., 1408: 312-22 (1998).
Fujita, T., Complement Activation and Lectin Pathway, *Rinsho Meneki*, 29:405-410 (1997). (Japanese with English abstract translation).
Garred et al., Increased Frequency of Homozygosity of Abnormal Mannan-Binding Protein Alleles in Patents with Suspected Immunodeficiency, *Lancet*, 346: 941-3 (1995).
Garred et al., Susceptibility to HIV Infection and Progression of AIDS in Relation to Variant Alleles of Mannose Binding Lectin, *Lancet*, 349: 236-40 (1997).
Goding, Antibody Production by Hybridomas, *J. Immunol. Methods*, 39: 285-308 (1980).
Grunstein et al., Colony Hybridization: A Method for the Isolation of Cloned DNAs That Contain a Specific Gene, *Proc. Natl. Acad. Sci. USA*, 72: 3961-5 (1975).
Gubler et al., A Simple and Very Efficient Method for Generating cDNA Libraries, *Gene*, 25: 263-9 (1983).
Hochkeppel et al., Monoclonal Antibodies Against Human Fibroblast Interferon. *Eur. J. Biochem*,. 118: 437-42 (1981).
Huynh et al., Constructing and Screening cDNA Libraries in λgt10 and λgt11. Chap. 2, DNA Cloning, vol. 1, A Practical Approach, D.M. Glover, ed., IRL Press, Oxford, 49-78. (1985).
Ikeda et al., Serum Lectin with Known Structure Activates Complement Through the Classical Pathway, *J. Biol. Chem.*, 262: 7451-4 (1987).

(Continued)

*Primary Examiner* — Anand Desai
(74) *Attorney, Agent, or Firm* — Marshall, Gerstein & Borun LLP

(57) ABSTRACT

Provided are isolated collectin (CL-L2s) genes including a base sequence set out in SEQ ID NO: 1, 3, 5, 7, 9, 12, 36, 38 or 40 relating to a novel collectin which are expected to exhibit an antibacterial activity, an antiviral activity and the like particularly in a human body; and isolated collectin proteins including an amino acid sequence set out in SEQ ID NO: 2, 4, 6, 8, 10, 13, 37, 39 or 41 and derivatives and fragments thereof.

5 Claims, 10 Drawing Sheets

(56) References Cited

OTHER PUBLICATIONS

Kase, et al., Human mannan-binding lectin inhibits the infection of influenza A virus without complement, Immunology, 97: 385-92 (1999).
Kawai et al., Cloning and Characterization of a cDNA Encoding Bovine Mannan-Binding Protein, *Gene*, 186:161-5 (1997).
Kawasaki et al., A Serum Lectin (Mannan-Binding Protein) Has Complement-Dependent Bactericidal Activity, *J. Biochem.*, 106: 483-9 (1989).
Kohler et al., Continuous Cultures of Fused Cells Secreting Antibody of Predefined Specificity, *Nature*, 256: 495-7 (1975).
Kurata, Structure and Function of Mannan-Binding Proteins Isolated from Human Liver and Serum. *J. Biochem.*, 115: 1148-54 (1994).
Lavitrano et al., Sperm Cells as Vectors for Introducing Foreign DNA into Eggs: Genetic Transformation of Mice, *Cell*, 57: 717-23 (1989).
Lim et al., Primary Structure of Bovine Collectin 43 (CL 43). Comparison with Conglutinin and Lung Surfactant Protein D, *J. Biol. Chem.*, 269: 11820-4 (1994).
Lipscombe et al., Mutations in the Human Mannose Binding Gene: Frequencies in Several Population Groups, *Eur. J. Hum. Gen.*, 4: 13-9 (1996).
Lu et al., Purification, Characterization and cDNA Cloning of Human Lung Surfactant Protein D. *Biochem. J.*, 284: 795-802 (1992).
Ma et al., Functional Expression of Human Mannan-Binding Proteins (MBPs) in Human Hepatoma Cell Lines Infected by Recombinant Vaccinia Virus: Post-Translational Modification, Molecular Assembly, and Differentiation of Serum and Liver MBP, *J. Biochem.*, 122: 810-8 (1997).
Malhortra et al., Glycosylation Changes of IgG Associated with Rheumatoid Arthritis can Activate Complement via the Mannose Binding Protein, *Nature Med.*, 1: 237-43 (1995).
Malhortra et al., Interaction of C1q Receptor with Lung Surfactant Protein A*, *Eur. J. Immun.*, 22:1437-45 (1992).
Markset al., Site-Specific Mutagenesis of the Human Fibroblast Interferon Gene, *Proc. Natl. Sci. USA*, 81: 5662-6 (1984).
Matsuda et al., Involvement of Mannan Binding Protein with Crisis and Progression of IgA Nephrosis, *J. of Nephrology Assoc. of Japan*, 39:235 (1997). (Japanese with English abstract translation).
Matteucci et al., Synthesis of Deoxyoligonucleotides on a Polymer Support, *J. Am. Chem.*, 103: 3185-91 (1981).
Maxam et al., A New Method for Sequencing DNA, *Proc. Natl. Acad. Sci. USA*, 74: 560-4 (1977).
Nepomuceno et al., cDNA Cloning and Primary Structure Analysis of C1qRp, the Human C11/MBL/SPA Receptor That Mediates Enhanced Phagocytosis in vitro, *Immunity*, 6: 119-29 (1997).
Ohta et al., The Mechanism of Carbohydrate-Mediated Complement Activation by the Serum Mannan-Binding Protein, *J. Biol. Chem.*, 265:1980-4 (1990).
Ohtani, et al., High-level and effective production of human mannan-binding lectin (MBL) in Chinese hamster ovary (CHO) cells, *J. Immunol. Methods*, 222: 135-44 (1999).
Ohtani, et al., Molecular Cloning of a Novel Human Collectin from Liver (CL-L1), *J. Biol. Chem.*, 274:13681-9 (1999).
Okayama et al., A cDNA Cloning Vector That Permits Expression of cDNA Inserts in Mammalian Cells, *Mol. Cell. Biol.*, 3:280-9 (1983).
Okayama et al., High Efficiency Cloning of Full-Length Cdna, *Mol. Cell. Biol.*, 2: 161-70 (1982).
Parce et al., Detection of Cell-Affecting Agents with a Silicon Biosensor, *Science*, 246: 243-8 (1989).
Sambrook et al., Molecular Cloning: A Laboratory Manual, Second Edition, Cold Spring Harbor Laboratory Press, 2:108 (1989).
Sampaio et al., Organization, Regulatory Sequences, and Alternatively Spliced Transcripts of the Mucosal Address in Cell Adhesion Molecule-1 (MAdCAM-1) Gene, *J. Immunol.*, 155: 2477-86 (1995).
Sanger et al., DNA Sequencing with Chain-Terminating Inhibitors, *Proc. Natl Acad. Sci. USA*, 74: 5463-7 (1977).
Sastry et al., The Human Mannose-Binding Protein Gene: Exon Structure Reveals its Evolutionary Relationship to a Human Pulmonary Surfactant Gene and Localization to Chromosome 10, *J. Exp. Med.*, 170: 1175-89 (1989).
Sato et al., Molecular Characterization of a Novel Serine Protease Involved in Activation of the Complement System by Mannose-Binding Protein, *Int. Immunol.*, 6: 665-9 (1994).
Secher et al., A Monoclonal Antibody for Large-Scale Purification of Human Leukocyte Interferon, *Nature*, 285: 446-50 (1980).
Sumiya et. al., Mannose Binding Protein, Genetic Variants and the Risk of Infection, *Q. J. Med.*, 89: 723-6 (1996).
Sumiya et. al., Molecular Basis of Opsonic Defect in Immunodeficient Children, *Lancet*, 337: 1569-70 (1991).
Summerfield et al., Mannose Binding Protein Gene Mutations Associated with Unusual and Severe Infections in Adults, *Lancet*, 345: 886-9 (1995).
Super et. al., Association of Low Levels of Mannan Binding Protein with a Common Defect of Opsonisation, *Lancet*, 2: 1236-9 (1989).
Suzuki et al., Characterization of Recombinant Bovine Conglutinin Expressed in a Mammalian Cell, *Biochem. Biophys. Res. Commun.*, 238: 856-63 (1997).
Suzuki et al., Cloning and Sequencing of a cDNA Coding for Bovine Conglutinin, *Biochem. Biophys. Res. Commun.*, 191: 335-42 (1993).
Takeuchi et al., Induction of the Gene Encoding Mucosal Vascular Address in Cell Adhesion Molecule 1 by Tumor Necrosis Factor alpha is mediated by Nf-kB Proteins, *Proc. Natl. Acad. Sci. USA*, 92: 3561-5 (1995).
Tan et al., Improvements on the Purification of Mannan-Binding Lectin and Demonstration of its $Ca^{2+}$-Independent Association with a C1s-Like Serine Protease, *Biochem. J.*, 391: 329-32 (1996).
Taylor et al., Structure and Evolutionary Origin of the Gene Encoding a Human Serum Mannose Binding Protein, *Biochem J.*, 262: 763-71 (1989).
Thomas, et al., Mutation of Gene for Mannose Binding Protein Associated with Chronic Hepatitis B Viral Infection, *Lancet*, 348: 1417-9 (1996).
Uemura et al., Correlation Between Structure and Function of Calcium Dependence Animal Lectin on Host Defense, *Jikken Igaku*, 13 (1995). (Japanese with English abstract translation).
Wada et al., Characterization of Rat Liver Mannan-Binding Protein Gene, *J. Biochem.*, 111: 66-73 (1992).
Wakamiya et. al., Anti-Viral Activity by Collectin, *Rinsho Meneki.*, 29: 508-13 (1997). (Japanese with English abstract translation).
Wakamiya et. al., Isolation and Characterization of Conglutinin as an Influenza A Virus Inhibitor, *Biochem. Biophys. Res. Comm.*, 187: 1270-8 (1992).
Wakamiya et. al., The Mannose Binding Protein and Congulutinin in Bovine Serum Have a Antiviral Activity Against Influenza Virus, *Glycoconjugate J.*, 8: 235 (1991).
Wakamiya, Novel Collectin, SEQ ID No. 4 alignment result 5, Database: Issued_Patents_AA, US-09-600-932-3, Jan. 23, 1998.
Wakamiya, Novel Collectin, SEQ ID No. 6 alignment result 5, Database: Issued_Patents_AA, US-09-600-932-3, Jan. 23, 1998.
Wakamiya, Novel Collectin, SEQ ID No. 8 alignment result 5, Database: Issued_Patents_AA, US-09-600-932-3, Jan. 23, 1998.
Wakamiya, Novel Collectin, SEQ ID No. 10 alignment result 5, Database: Issued_Patents_AA, US-09-600-932-3, Jan. 23, 1998.
Supplemental Partial European Search report dated Jul. 28, 2004 on the corresponding European Patent Application No. 01922014.

```
MBP                         ------SERKALQTEMARIKKWLTESLGKQVGNKFFLTNGEIMTF
SP-A     GQKGDPG-KSPDGDSSLAA-FAHLDEELQATLH-----FHQILTRGALS--LQGSI-------MTVGEKVFSSNGQSINF
SP-D     GDKGIPGD-RGAKGESGLPDVASLRQQVEALQGQVQHLQAAFSQYKKVELFPNGQSVGEKIFKTAGFVKPF
CL-L1    -----------------IVCDQGRYRRFVGQLDISIARIKISMKFVKN--VIAGIRTEEKFMYIVQEEKNM
CL-L2-1  -----------------LPQGSQLRKAIGEMDNQVSQTSEIKFIKN--AVAGVRETESKIYILVKEERY

EKVKALQVKFQASVETRNAENGAIQNLI----KEE-AFLGITEKTEGQFVDLTGNRIT-YTNWNEGEP
         DAIQEAQRIAVERNPEENEALSFVKKIYNTY-AYVGLTEGPSPGDFRYSDGTFVN-YTNWYRGEP
         TEAQLLCTQAGQLASERSAPENAALQQLMVAKNEA-AFLSMTDSKTEGKFTYPTGESIV-YSNWAPGEP
         RESLTHQRIRGGMLAMPKDEAANTLIADYVARSGFFRVFIGVNDLEREGQYMFTDNTPLQNYSNWNEGEP
         ADAQISQGRGCTLSMPKDEAANGIMAAMLAQAGLARVFIGINDLEKEGAFVYSDHSMRTFNKWRSGEP

NNEGSDEDCVLLIKNGQWNDVPGSSHLAVCEFPI*----
         AGRG-KEQCVEMYIDGQWNDRNQLYSRLTICEF*-----
         NDDGSEDCVELFTNGKWNDRAGEKRLVCEF*-----
         SDPYGHEDCVEMLSSGRWNCTECHIMYFVCEFIKKK*
         NNAVDEDCVEMVASGGMNDVACHTTMYFMCEFDKENM*
```

Fig. 6

1: α-D-mannose BP-probe
2: α-L-fucose BP-probe
3: α-acetylgalactosamine BP-probe
4: α-acetylneuraminic acid BP-probe
5: α-D-mannose-6-phosphoric acid BP-probe
6: negative control

COLLECTIN

This application is a divisional of U.S. patent application Ser. No. 12/334,052 filed Dec. 12, 2008, which in turn is a continuation of U.S. patent application Ser. No. 10/258,105 filed Oct. 21, 2002, which in turn is a U.S. National Phase of International (PCT) Application No. PCT/JP2001/03468 filed Apr. 23, 2001, which claims the benefit of priority of Japanese Application No. 2000-120358 filed Apr. 21, 2000. Each of the foregoing applications is incorporated herein by reference.

FIELD OF THE INVENTION

The present invention relates to isolated human and mouse collectins (herein referred to as "hCL-L2" and "mCL-L2" respectively, or merely as "CL-L2" when discrimination of both is not intended), genes and proteins, the homologues, mutants, modified forms and polymorphic variants thereof (these are collectively referred to as "derivatives"), fragments thereof (hereinafter collectively referred to as "CL-L2s" for all of these), and the detection of the same. The present invention further relates to compositions which comprise CL-L2s for pharmaceutical use, diagnostic use and research use, and methods for the production and use of the same. Additionally, the present invention relates to agonists and antagonists of CL-L2s proteins, as well as methods for screening drugs using CL-L2s. Moreover, the present invention also relates to expression vectors comprising CL-L2s gene, transformed cells that were transformed with the expression vector, antibodies to CL-L2s protein, and cells that produce the antibody.

BACKGROUND OF THE INVENTION

Complement systems that play an important role in a body defense mechanism are known to include: a classic pathway in which an immunoglobulin serves as a recognition molecule followed by the activation of C1 that is the first component of the complement; and an alternative pathway in which C3, which is the third component of the complement, is directly coupled to foreign substances such as bacteria. In addition to these pathways of the complement activation, a lectin pathway was illustrated in which a mannose binding protein (hereinafter referred to as "MBP"), which is a serum lectin, activates the complement system through the direct recognition of and coupling with a carbohydrate chain on the surface of the foreign substance, in recent years (Sato, T. et al., Int. Immunol., 6, 665-669, 1994).

MBP is a C type lectin which specifically binds to mannose, N-acetylglucosamine and the like in the presence of Ca, of which structure comprises a collagen-like domain containing at least one (Gly-Xaa-Yaa)n, and carbohydrate chain recognition domain (CRD). Similarly to MBP, lectins having a collagen-like domain and CRD are generically called as collectin (Malhotora, R. et al., Eur. J. Immunol., 22, 1437-1445, 1992), which include collectin-43 (CL-43), surfactant protein A (SP-A), surfactant protein D (SP-D), bovine conglutinin (BKg) and the like, in addition to MBP. Collectin has an opsonic activity, which is believed to participate in fundamental immunity against a variety of microorganisms such as bacteria and viruses (Kawasaki, N. et al., J. Biochem., 106, 483-489, 1989; Ikeda, K. et al., J. Biol. Chem., 262, 7451-7454, 1987; Ohta, M. et al., J. Biol. Chem., 265, 1980-1984, 1990; Summerfield, J. A. et al., Lancet, 345, 886, 1995).

These collectins are known to be constituted from a basic structure containing characteristic domains such as (1) CRD and (2) collagen-like domain and the like as shown in FIG. 1(a) (Malhortra et al., Eur. J. Immunol., 22, 1437-1445, 1992). This basic structure forms a subunit through composing a triple helix at the collagen-like domain, and thus these subunits further form an oligomer structure such as trimer, tetramer, hexamer and the like.

Recently, collectins were suggested to participate in non-specific immune response, e.g., it was reported that for example, they are playing important roles in neutralizing and excluding various microorganisms in infants having insufficient maternal antibodies from mother or having specific defense systems which were insufficiently developed (Super et al., Lancet, 2, 1236-1239, 1989). Moreover, results of investigation are reported involving in roles of these collectins in the body defense system of a host, which for example, suggest that the host becomes more susceptible to infections through the lowered concentration of MBP in blood resulting from genetic mutation of MBP (Sumiya et al., Lancet, 337, 1569-1570, 1991). In addition, it was reported that serum MBP content shows a lowered level upon the failure of opsonization (Madsen, H. O. et al., Immuno genetics, 40, 37-44, 1994), whilst bacterial infections readily occur (Garred, P. et al., Lancet, 346, 941-943, 1995). Therefore, MBP can be believed to play important roles in an immune system.

The present inventors previously found that BKg and MBP inhibit infections by H1 and H3 types influenzae A viruses as well as a haemagglutination activity (Wakamiya et al., Glycoconjugate J., 8, 235, 1991; Wakamiya et al., Biochem. Biophys. Res. Comm., 187, 1270-1278, 1992). Thereafter, a cDNA clone encoding BKg was obtained, and the relevance between BKg and SP-D and the like has been also found (Suzuki et al., Biochem. Biophys. Res. Comm., 191, 335-342, 1993).

Accordingly, collectins are substances to which usefulness in the elucidation of body defense mechanisms and utilities as a biologically active substance are expected. Thus, the finding of novel molecular species belonging to this family may greatly contribute in various medical fields and biological fields in addition to the therapy of infectious diseases.

DISCLOSURE OF THE INVENTION

The object of the present invention is to provide materials that can be utilized in the elucidation of mechanisms of fundamental immunity; in the elucidation of mechanisms of the development of a wide variety of diseases such as bacterial infections; in the diagnostic, prophylactic and therapeutic methods thereof; and for the development of reagents and drugs for the same.

Accordingly, aspects provided by the present invention are as described below.

(1) A protein comprising an amino acid sequence consisting of 271 amino acids set out in the amino acid position 1-271 of SEQ ID NO: 2, or a protein consisting of an amino acid sequence set out in SEQ ID NO: 2 having deletion, substitution or addition of one or several amino acids therein and having an equal property to that of the protein having an amino acid sequence set out in the amino acid position 1-271 of SEQ ID NO: 2, or a derivative or a fragment thereof;

(2) A base sequence set out in SEQ ID NO: 45 (corresponding to a base sequence set out in the base position 265-1077 of SEQ ID NO: 1), a base sequence encoding an amino acid sequence set out in the amino acid position 1-271 of SEQ ID NO: 2 or a fragment thereof, or a base sequence that hybridizes to any one of said base sequences or a base sequence complementary thereto under a stringent condition and encodes a protein having an equal property to that of the protein having an amino acid sequence set out in the amino acid position 1-271 of SEQ ID NO: 2;

(3) A protein comprising an amino acid sequence consisting of 245 amino acids et out in the amino acid position 1-245 of SEQ ID NO: 4, or a protein consisting of an amino acid sequence set out in the amino acid position 1-245 of SEQ ID NO: 4 having deletion, substitution or addition of one or several amino acids therein and having an equal property to that of the protein having an amino acid sequence set out in the amino acid position 1-245 of SEQ ID NO: 4, or a derivative or a fragment thereof;

(4) A base sequence set out in SEQ ID NO: 46 (corresponding to a base sequence set out in the base position 141-875 of SEQ ID NO: 3), a base sequence encoding an amino acid sequence set out in the amino acid position 1-245 of SEQ ID NO: 4 or a fragment thereof, or a base sequence that hybridizes to any one of said base sequences or a base sequence complementary thereto under a stringent condition and encodes a protein having an equal property to that of the protein having an amino acid sequence set out in the amino acid position 1-245 of SEQ ID NO: 4;

(5) A protein comprising an amino acid sequence consisting of 159 amino acids set out in SEQ ID NO: 47 (corresponding to an amino acid sequence set out in the amino acid position 113-271 of SEQ ID NO: 2), or a protein consisting of an amino acid sequence set out in SEQ ID NO: 2 having deletion, substitution or addition of one or several amino acids therein and having an equal property to that of the protein having an amino acid sequence set out in the amino acid position 113-271 of SEQ ID NO: 2, or a derivative or a fragment thereof;

(6) A base sequence set out in SEQ ID NO: 48 (corresponding to a base sequence set out in the base position 601-1077 of SEQ ID NO: 1), a base sequence encoding an amino acid sequence set out in the amino acid position 113-271 of SEQ ID NO: 2 or a fragment thereof, or a base sequence that hybridizes to any one of said base sequences or a base sequence complementary thereto under a stringent condition and encodes a protein having an equal property to that of the protein having an amino acid sequence, set out in the amino acid position 113-271 of SEQ ID NO: 2;

(7) The protein further comprising a sequence (Gly-Xaa-Yaa)n, wherein n represents an integer of from 1 to 50, Xaa and Yaa represent an amino acid residue, which may be the same or different, at an N-terminal of the protein according to (5);

(8) The protein according to (7) wherein said (Gly-Xaa-Yaa)n is selected from the group of sequences consisting of:
Gly-Leu-Lys-Gly-Asp-Ala-Gly-Glu-Lys-Gly-Asp-Lys-Gly-Ala-Pro-Gly-Arg-Pro-Gly-Arg-Val-Gly-Pro-Thr-Gly-Glu-Lys-Gly-Asp-Met-Gly-Asp-Lys-Gly-Gln-Lys-Gly-Ser-Val-Gly-Arg-His-Gly-Lys-Ile-Gly-Pro-Ile-Gly-Ser-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 49 (corresponding to the amino acid position 41-112 of SEQ ID NO: 2)),
Gly-Asp-Ala-Gly-Glu-Lys-Gly-Asp-Lys-Gly-Ala-Pro-Gly-Arg-Pro-Gly-Arg-Val-Gly-Pro-Thr-Gly-Glu-Lys-Gly-Asp-Met-Gly-Asp-Lys-Gly-Gln-Lys-Gly-Ser-Val-Gly-Arg-His-Gly-Lys-Ile-Gly-Pro-Ile-Gly-Ser-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 50 (corresponding to the amino acid position 44-112 of SEQ ID NO: 2, or the amino acid position 18-86 of SEQ ID NO: 4))
Gly-Glu-Lys-Gly-Asp-Ser-Gly-Asp-Ile-Gly-Pro-Pro-Gly-Pro-Asn-Gly-Glu-Pro-Gly-Oly-Leu-Pro (SEQ ID NO: 51 (corresponding to the amino acid position 92-112 of SEQ ID NO: 2 or the amino acid position 66-86 of SEQ ID NO: 4)),
Gly-Asp-Met-Gly-Asp-Lys-Gly-Gln-Lys-Gly-Ser-Val-Gly-Arg-His-Gly-Lys-Ile-Gly-Pro-Ile-Gly-Ser-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 52 (corresponding to the amino acid position 68-112 of SEQ ID NO: 2 or the amino acid position 42-86 of SEQ ID NO: 4)),
Gly-Asp-Ala-Gly-Glu-Lys-Gly-Asp-Lys-Gly-Ala-Pro-Gly-Arg-Pro-Gly-Arg-Val-Gly-Pro-Thr-Gly-Glu-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 11 (corresponding to the amino acid position 44-67 and 92-112 of SEQ ID NO: 2 or the amino acid position 18-41 and 66-86 of SEQ ID NO: 4)), Gly-Leu-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 43 (corresponding to the amino acid position 41-43 and 92-112 of SEQ ID NO: 2)),
Gly-Leu-Lys-Gly-Asp-Met-Gly-Asp-Lys-Gly-Gln-Lys-Gly-Ser-Val-Gly-Arg-His-Gly-Lys-Ile-Gly-Pro-Ile-Gly-Ser-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 42 (corresponding to the amino acid position 41-43 and 68-112 of SEQ ID NO: 2)), or
Gly-Leu-Lys-Gly-Asp-Ala-Gly-Glu-Lys-Gly-Asp-Lys-Gly-Ala-Pro-Gly-Arg-Pro-Gly-Arg-Val-Gly-Pro-Thr-Gly-Glu-Lys-Gly-Glu-Lys-Gly-Asp-Ser-Gly-Asp-Ile-Gly-Pro-Pro-Gly-Pro-Asn-Gly-Glu-Pro-Gly-Leu-Pro (SEQ ID NO: 44 (corresponding to the amino acid position 41-67 and 92-112 of SEQ ID NO: 2));

(9) A base sequence encoding the protein according to (7) or (8);

(10) A protein comprising an amino acid sequence of:
Met-Arg-Gly-Asn-Leu-Ala-Leu-Val-Gly-Val-Leu-Ile-Ser-Leu-Ala-Phe-Leu-Ser-Leu-Leu-Pro-Ser-Gly-His-Pro-Gln-Pro-Ala-Gly-Asp-Asp-Ala-Cys-Ser-Val-Gln-Ile-Leu-Val-Pro (SEQ ID NO: 53 (corresponding to the amino acid position 1-40 of SEQ ID NO: 2)) at an N-terminal of the sequence (Gly-Xaa-Yaa)n of the protein according to (7) or (8) in addition thereto;

(11) A protein comprising a sequence of:
Met-Trp-Trp-Val-Pro-Pro-Ser-Pro-Tyr-Gly-Cys-Leu-Pro-Cys-Ala-Leu-Pro (SEQ ID NO: 54 (corresponding to the amino acid position 1-17 of SEQ ID NO: 4)) at an N-terminal of the sequence (Gly-Xaa-Yaa)n of the protein according to (7) or (8) in addition thereto.

(12) A base sequence encoding the protein according to (10) or (11);

(13) A protein comprising an amino acid sequence consisting of 197 amino acids set out in the amino acid position 1-197 of SEQ ID NO: 6, or a protein consisting of an amino acid sequence set out in the amino acid position 1-197 of SEQ ID NO: 6 having deletion, substitution or addition of one or several amino acids therein and having an equal property to that of the protein having an amino acid sequence set out in the amino acid position 1-197 of SEQ ID NO: 6, or a derivative or a fragment thereof;

(14) A base sequence set out in SEQ ID NO: 55 (corresponding to a base sequence set out in the base position 141-731 of SEQ ID NO: 5), a base sequence encoding an amino acid sequence set out in the amino acid position 1-197 of SEQ ID NO: 6 or a fragment thereof, or a base sequence that hybridizes to any one of said base sequences or a base sequence complementary thereto under a stringent condition and encodes a protein having an equal property to that of the protein having an amino acid sequence set out in the amino acid position 1-197 of SEQ ID NO: 6;

(15) A protein comprising an amino acid sequence consisting of 221 amino acids set out in the amino acid position 1-221 of SEQ ID NO: 8, or a protein consisting of an amino acid sequence set out in the amino acid position 1-221 of SEQ ID NO: 8 having deletion, substitution or addition of one or several amino acids therein and having an equal property to that of the protein having an amino acid sequence set out in the amino acid position 1-221 of SEQ ID NO: 8, or a derivative or a fragment thereof;

(16) A base sequence set out in SEQ ID NO: 56 (corresponding to a base sequence set out in the base position 141-803 of SEQ ID NO: 7), a base sequence encoding an amino acid sequence set out in the amino acid position 1-221 of SEQ ID NO: 8 or a fragment thereof, or a base sequence that hybridizes to any one of said base sequences or a base sequence complementary thereto under a stringent condition and encodes a protein having an equal property to that of the protein having an amino acid sequence set out in the amino acid position 1-221 of SEQ ID NO: 8;

(17) A protein comprising an amino acid sequence consisting of 221 amino acids set out in the amino acid position 1-221 of SEQ ID NO: 10, or a protein consisting of an amino acid sequence set out in the amino acid position 1-221 of SEQ ID NO: 10 having deletion, substitution or addition of one or several amino acids therein and having an equal property to that of the protein having an amino acid sequence set out in the amino acid position 1-221 of SEQ ID NO: 10, or a derivative or a fragment thereof;

(18) A base sequence set out in SEQ ID NO: 57 (corresponding to a base sequence set out in the base position 141-803 of SEQ ID NO: 9), a base sequence encoding an amino acid sequence set out in the amino acid position 1-221 of SEQ ID NO: 10 or a fragment thereof, or a base sequence that hybridizes to any one of said base sequences or a base sequence complementary thereto under a stringent condition and encodes a protein having an equal property to that of the protein having an amino acid sequence set out in the amino acid position 1-221 of SEQ ID NO: 10;

(19) A protein comprising an amino acid sequence consisting of 271 amino acids set out in the amino acid position 1-271 of SEQ ID NO: 13, or a protein consisting of an amino acid sequence set out in the amino acid position 1-271 of SEQ ID NO: 13 having deletion, substitution or addition of one or several amino acids therein and having an equal property to that of the protein having an amino acid sequence set out in the amino acid position 1-271 of SEQ ID NO: 13, or a derivative or a fragment thereof;

(20) A base sequence set out in SEQ ID NO: 58 (corresponding to a base sequence set out in the base position 157-969 of SEQ ID NO: 12), a base sequence encoding an amino acid sequence set out in the amino acid position 1-271 of SEQ ID NO: 13 or a fragment thereof, or a base sequence that hybridizes to any one of said base sequences or a base sequence complementary thereto under a stringent condition and encodes a protein having an equal property to that of the protein having an amino acid sequence set out in the amino acid position 1-271 of SEQ ID NO: 13;

(21) A protein comprising an amino acid sequence consisting of 223 amino acids set out in the amino acid position 1-223 of SEQ ID NO: 37, or a protein consisting of an amino acid sequence set out in the amino acid position 1-223 of SEQ ID NO: 37 having deletion, substitution or addition of one or several amino acids therein and having an equal property to that of the protein having an amino acid sequence set out in the amino acid position 1-223 of SEQ ID NO: 37, or a derivative or a fragment thereof;

(22) A base sequence set out in SEQ ID NO 59 (corresponding to a base sequence set out in the base position 265-933 of SEQ ID NO: 36), a base sequence encoding an amino acid sequence set out in the amino acid position 1-223 of SEQ ID NO: 37 or a fragment thereof, or a base sequence that hybridizes to any one of said base sequences or a base sequence complementary thereto under a stringent condition and encodes a protein having an equal property to that of the protein having an amino acid sequence set out in the amino acid position 1-223 of SEQ ID NO: 37;

(23) A protein comprising an amino acid sequence consisting of 247 amino acids set out in the amino acid position 1-247 of SEQ ID NO: 39, or a protein consisting of an amino acid sequence set out in the amino acid position 1-247 of SEQ ID NO: 39 having deletion, substitution or addition of one or several amino acids therein and having an equal property to that of the protein having an amino acid sequence set out in the amino acid position 1-247 of SEQ ID NO: 39, or a derivative or a fragment thereof;

(24) A base sequence set out in SEQ ID NO: 60 (corresponding to a base sequence set out in the base position 265-1005 of SEQ ID NO: 38), a base sequence encoding an amino acid sequence set out in the amino acid position 1-247 of SEQ ID NO: 39 or a fragment thereof, or a base sequence that hybridizes to any one of said base sequences or a base sequence complementary thereto under a stringent condition and encodes a protein having an equal property to that of the protein having an amino acid sequence set out in the amino acid position 1-247 of SEQ ID NO: 39;

(25) A protein comprising an amino acid sequence consisting of 247 amino acids set out in the amino acid position 1-247 of SEQ ID NO: 41, or a protein consisting of an amino acid sequence set out in the amino acid position 1-247 of SEQ ID NO: 41 having deletion, substitution or addition of one or several amino acids therein and having an equal property to that of the protein having an amino acid sequence set out in the amino acid position 1-247 of SEQ ID NO: 41, or a derivative or a fragment thereof;

(26) A base sequence set out in SEQ ID NO: 61 (corresponding to a base sequence set out in the base position 265-1005 of SEQ ID NO: 40), a base sequence encoding an amino acid sequence set out in the amino acid position 1-247 of SEQ ID NO: 41 or a fragment thereof, or a base sequence that hybridizes to any one of said base sequences or a base sequence complementary thereto under a stringent condition and encodes a protein having an equal property to that of the protein having an amino acid sequence set out in amino acid position 1-247 of SEQ ID NO: 41;

(27) A vector comprising a base sequence according to (2), (4), (6), (9), (12), (14), (16), (18), (20), (22), (24) or (26);

(28) A transformed cell carrying a base sequence according to (2), (4), (6), (9), (12), (14), (16), (18), (20), (22), (24) or (26) in a manner to allow the expression;

(29) A process for the production of a protein which comprises the steps of: culturing a cell transformed with the base sequence according to (2), (4), (6), (9), (12), (14), (16), (18), (22), (24) or (26); and harvesting thus produced hCL-L2s protein;

(30) A process for the production of a protein which comprises the steps of: culturing a cell transformed with the base sequence according to (20); and harvesting thus produced mCL-L2s protein;

(31) The process according to (29) or (30) wherein said cell is *Escherichia coli*, an animal cell or an insect cell;

(32) A transgenic non-human animal having an altered expression level of CL-L2s gene;

(33) A knockout mouse wherein a function of mCL-L2s gene is deficient;

(34) An antibody to the protein according to (1), (3), (5), (7), (8), (10), (11), (13), (15), (17), (19), (21), (23) or (25), or a fragment thereof;

(35) The antibody according to (34), which is a polyclonal antibody, a monoclonal antibody or a peptide antibody;

(36) A process for measuring a CL-L2s protein or a fragment thereof on the basis of an immunological binding between the antibody according to (34) or (35) and the CL-L2s protein or a fragment thereof;

(37) An agonist that stimulates a function of the protein according to (1), (3), (5), (7), (8), (10), (11), (13), (15), (17), (19), (21), (23) or (25);

(38) An antagonist that inhibits a function of the protein according to (1), (3), (5), (7), (8), (10), (11), (13), (15), (17), (19), (21), (23) or (25);

(39) A process for screening a drug wherein the protein according to (1), (3), (5), (7), (8), (10), (11), (13), (15), (17), (19), (21), (23) or (25) is used;

(40) A drug which is obtained by the process for the screening according to (39).

BRIEF DESCRIPTION OF THE DRAWINGS

FIG. 2 is a drawing illustrating a preceding half of an alignment of amino acid sequences of four kinds of collectins reported heretofore (MBP—SEQ ID NO: 62; SP-A—SEQ ID NO: 63; SP-D—SEQ ID NO: 64; and CL-L1—SEQ ID NO: 65).

FIG. 3 is a drawing illustrating a latter half of the alignment to that of FIG. 2 (MBP—SEQ ID NO: 62; SP-A—SEQ ID NO: 63; SP-D—SEQ ID NO: 64; and CL-L1—SEQ ID NO: 65).

FIG. 5 is a drawing illustrating a preceding half of an alignment of amino acid sequences of four kinds of collectins reported heretofore and the novel collectin (hCL-L2-1—SEQ ID NO: 1) of the present invention (MBP—SEQ ID NO: 62; SP-A—SEQ ID NO: 63; SP-D—SEQ ID NO: 64; and CL-L1—SEQ ID NO: 65).

FIG. 6 is a drawing illustrating a latter half of the alignment to that of FIG. 5 (MBP—SEQ ID NO: 62; SP-A—SEQ ID NO: 63; SP-D—SEQ ID NO: 64; CL-L1—SEQ ID NO: 65), and CL-L2-1—SEQ ID NO: 1).

BEST EMBODIMENT FOR CARRYING OUT THE INVENTION

The present inventors successfully cloned human and mouse novel collectin genes (hCL-L2-1 and mCL-L2). A CRD (amino acid position 113-271 of SEQ ID NOs: 2 and 13, amino acid position 87-245 of SEQ ID NO: 4), which is believed to participate in fundamental immunity, and a collagen-like domain (the amino acid position 41-112 of SEQ ID NOs: 2 and 13, the amino acid position 18-86 of SEQ ID NO: 4) having a sequence of (Gly-Xaa-Yaa)n were present at C-terminal of the novel CL-L2.

Figure 4:
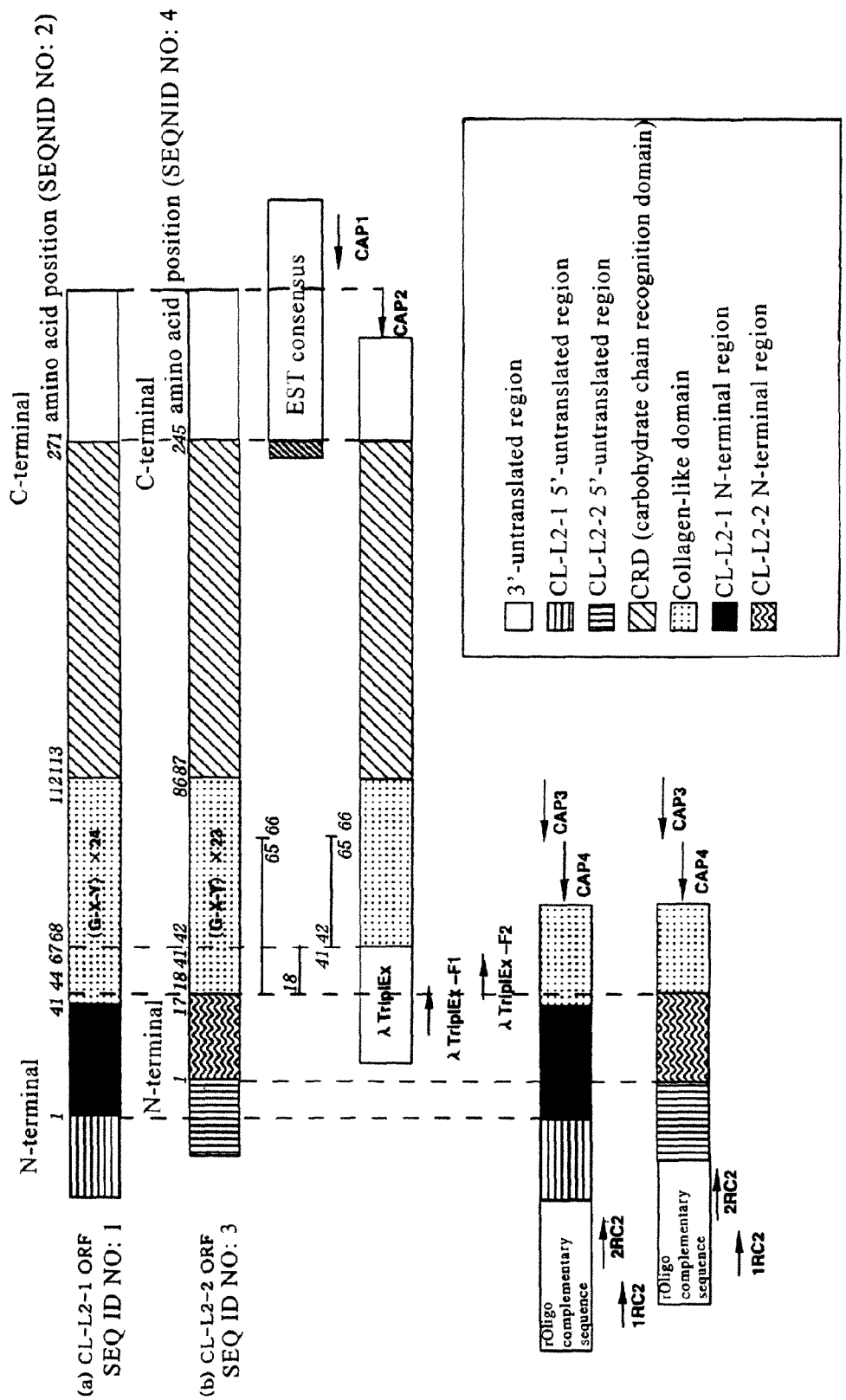
FIG. 4 depicts drawings (a) and (b) showing each primer employed for the determination of the sequence of the novel collectin of the present invention, and the novel collectin obtained thereby.

Moreover, two kinds of proteins (CL-L2-1 and CL-L2-2) having different N-terminal amino acid sequences were found for hCL-L2 as shown in FIG. 4. Specifically, N-terminal amino acids of CL-L2-1 (position 1-43) set out in SEQ ID NO: 2 and N-terminal amino acids of CL-L2-2 (position 1-17) set out in SEQ ID NO: 4 were different, whilst the rest being identical. Further, although position of 1-43 of N-terminal amino acid of CL-L2-1 contained a signal sequence and one coil of a collagen-domain and the like, there were neither a signal sequence nor one coil of a collagen-like domain in position of 1-17 of N-terminal amino acid of CL-L2-2.

In addition, there existed three kinds of proteins corresponding to CL-L2-2, which result from alternative splicing of mRNA. Those are referred to as CL-L2-2v1 (SEQ ID NO: 5, 6), CL-L2-2v2 (SEQ ID NO: 7, 8) and CL-L2-2v3 (SEQ ID NO: 9, 10). CL-L2-2v1 is a form derived from CL-L2-2 set out in SEQ ID NO: 4 with deletion of the amino acid position of from 18 to 65 (i.e., deletion of the base position of from 192 to 335 of CL-L2-2 set out in SEQ ID NO: 3); CL-L2-2v2 is a form derived from CL-L2-2 set out in SEQ ID NO: 4 with deletion of the amino acid position of from 18 to 41 (i.e., deletion of the base position of from 192 to 263 of CL-L2-2 set out in SEQ ID NO: 3); and CL-L2-2v3 is a form derived from CL-L2-2 set out in SEQ ID NO: 4 with deletion of the amino acid position of from 42 to 65 (i.e., deletion of the base position of from 264 to 335 of CL-L2-2 set out in SEQ ID NO: 3). These three kinds of proteins all resulted from differential splicing of CL-L2-2 within the collagen-like domain thereof.

Furthermore, there existed three kinds of proteins corresponding to CL-L2-1, which result from alternative splicing of mRNA. Those are referred to as CL-L2-1v1 (SEQ ID NO: 36, 37), CL-L2-1v2 (SEQ ID NO: 38, 39) and CL-L2-1v3 (SEQ ID NO: 40, 41). CL-L2-1v1 is a form derived from CL-L2-1 set out in SEQ ID NO: 2 with deletion of the amino acid position of from 44 to 91 (i.e., deletion of the base position of from 394 to 537 of CL-L2-1 set out in SEQ ID NO: 1); CL-L2-1v2 is a form derived from CL-L2-1 set out in SEQ ID NO: 2 with deletion of the amino acid position of from 44 to 67 (i.e., deletion of the base position of from 394 to 465 of CL-L2-1 set out in SEQ ID NO: 1); and CL-L2-1 v3 is a form derived from CL-L2-1 set out in SEQ ID NO: 2 with deletion of the amino acid position of from 68 to 91 (i.e., deletion of the base position of from 466 to 537 of CL-L2-1 set out in SEQ ID NO: 1). These three kinds of proteins all resulted from differential splicing of CL-L2-1 within the collagen-like domain thereof.

hCL-L2 gene used herein includes hCL-L2-1 set out in SEQ ID NO: 1, hCL-L2-2 set out in SEQ ID NO: 3, hCL-L2-2v1 set out in SEQ ID NO: 5, hCL-L2-2v2 set out in SEQ ID NO: 7, hCL-L2-2v3 set out in SEQ ID NO: 9, hCL-L2-1v1 set out in SEQ ID NO: 36, hCL-L2-1v2 set out in SEQ ID NO: 38, and hCL-L2-1v3 set out in SEQ ID NO: 40 respectively, unless otherwise stated. hCL-L2 protein used herein includes hCL-L2-1 set out in SEQ ID NO: 2, hCL-L2-2 set out in SEQ ID NO: 4, hCL-L2-2v1 set out in SEQ ID NO: 6, hCL-L2-2v2 set out in SEQ ID NO: 8, hCL-L2-2v3 set out in SEQ ID NO: 10, hCL-L2-lyl set out in SEQ ID NO: 37, hCL-L2-1v2 set out in SEQ ID NO: 39, and hCL-L2-1v3 set out in SEQ ID NO: 41 respectively, unless otherwise stated. In addition, homologues, variants, modified forms and polymorphic variants thereof (these are collectively referred to as "derivatives"), and fragments of the same are also included. These may be naturally occurring or artificially produced. The present invention includes any of the foregoing substances.

mCL-L2 gene used herein includes mCL-L2 set out in SEQ ID NO: 12, unless otherwise stated. mCL-L2 protein used herein includes mCL-L2 set out in SEQ ID NO: 13, unless otherwise stated. In addition, homologues, variants, modified forms and polymorphic variants thereof (these are collectively referred to as "derivatives"), and fragments of the same are also included. These may be naturally occurring or artificially produced. The present invention includes any of the foregoing substances.

Moreover, the present invention also involves amino acid sequences substantially similar to the amino acid sequence set out in SEQ ID NO: 2, 4, 6, 8, 10, 13, 37, 39 or 41, SEQ ID NO: 47 (corresponding to the amino acid position of 113-271 of SEQ ID NO: 2), or to the amino acid sequence set out in the amino acid position of 113-271 of SEQ ID NO: 13; and base sequences encoding amino acid sequences substantially similar to the amino acid sequence set out in SEQ ID NO: 2, 4, 6, 8, 10, 13, 37, 39 or 41, SEQ ID NO: 47 (corresponding to the amino acid position of 113-271 of SEQ ID NO: 2), or to the amino acid sequence set out in the amino acid position of 113-271 of SEQ ID NO: 13. Furthermore, proteins comprising these amino acid sequences are also involved. The amino acid sequence substantially similar to the amino acid sequence set out in SEQ ID NO: 2, 4, 6, 8, 10, 13, 37, 39 or 41, SEQ ID NO: 47 (corresponding to the amino acid position of 113-271 of SEQ ID NO: 2), or to the amino acid sequence set out in the amino acid position of 113-271 of SEQ ID NO: 13 refers to the amino acid sequence having alteration such as substitution, deletion, addition and/or insertion of one or several amino acids therein as long as the protein has an equal property to that of the protein comprising an amino acid sequence set out in SEQ ID NO: 2, 4, 6, 8, 10, 13, 37, 39 or 41, SEQ ID NO: 47 (corresponding to the amino acid position of 113-271 of SEQ ID NO: 2), or the amino acid sequence set out in the amino acid position of 113-271 of SEQ ID NO: 13. These may be naturally occurring, or artificially synthesized.

Such deletion, substitution, and/or addition of one or several amino acids referred to herein may be deletion, substitution, and/or addition of amino acid(s) without large extent of alteration of residues having hydrophobic, hydrophobic, acidic, basic group or the like of the novel collectin, and with small extent of alteration of each fundamental characteristics of (1) $Ca^{2+}$ dependent carbohydrate chain recognition domain (CRD) and (2) collagen-like domain. On the basis of amino acid sequences and structures of proteins of collectin family reported heretofore, it is believed that deletion, substitution, and/or addition of for example, (1) from about 1 to 10 amino acids in $Ca^{2+}$ dependent carbohydrate chain recognition domain (CRD) and (2) from about 1 to 50, preferably from about 1 to 15 amino acids in collagen-like domain may be allowed.

Equal property herein refers to a property inherent to a protein having an amino acid sequence prior to the alteration, e.g., a feature involving in tertiary structure of a protein.

Furthermore, the present invention also involves a nucleic acid sequence set out in SEQ ID NO: 1, 3, 5, 7, 9, 12, 36, 39 or 41, SEQ ID NO: 48 (corresponding to the base position of 601-1077 of SEQ ID NO: 1) or in the nucleic acid position of 493-969 of SEQ ID NO: 12, or a nucleic acid sequence comprising a fragment thereof, or a nucleic acid sequence that can hybridize to a nucleic acid sequence complementary thereto (hereinafter, referred to as "specified sequence") under a stringent condition. The stringent condition according to the present invention may involve a condition for example; incubating in a solution containing 5×SSC, 5% Denhardt's solution (0.1% BSA, 0.1% Ficol 1400, 0.1% PVP), 0.5% SDS and 20 μg/ml denatured sermon sperm DNA at 37° C. overnight followed by a wash with 2×SSC containing 0.1% SDS at room temperature. SSPE may be employed in place of SSC. Thus resultant nucleic acid sequence is speculated to exhibit at least 50% or greater homology to the specified sequence. Many of the proteins encoded by a nucleic acid sequence that can hybridize to the specified sequence under a stringent hybridization condition are believed to have an equal property to CL-L2s protein. Therefore, such proteins are also involved in the present invention as long as they have an equal property to CL-L2s protein.

In particular, the amino acid sequence of hCL-L2-1 set out in SEQ ID NO: 2 (amino acid position 1-271) represents a protein consisting of 271 amino acids, and thus the base sequence encoding the same (SEQ ID NO: 45) consists of 813 bases. Characteristic amino acid sequences such as those of a signal sequence, a collagen-like domain, a CRD domain and the like were present in the sequence. The base sequence encoding this protein is set out in SEQ ID NO: 1.

The amino acid sequence of hCL-L2-2 set out in SEQ ID NO: 4 (amino acid position 1-245) represents a protein consisting of 245 amino acids, and thus the base sequence encoding the same (SEQ ID NO: 46) consists of 735 bases. Characteristic amino acid sequences such as those of a collagen-like domain, a CRD domain and the like were present in the sequence. The base sequence encoding this protein is set out in SEQ ID NO: 3.

The amino acid sequence of hCL-L2-2v1 set out in SEQ ID NO: 6 (amino acid position 1-197) represents a protein consisting of 197 amino acids, and thus the base sequence encoding the same (SEQ ID NO: 55) consists of 591 bases. Characteristic amino acid sequences such as those of a collagen-like domain, a CRD domain and the like were present in the sequence. The base sequence encoding this protein is set out in SEQ ID NO: 5.

The amino acid sequence of hCL-L2-2v2 set out in SEQ ID NO: 8 (amino acid position 1-221) represents a protein consisting of 221 amino acids, and thus the base sequence encoding the same (SEQ ID NO: 56) consists of 663 bases. Characteristic amino acid sequences such as those of a collagen-like domain, a CRD domain and the like were present in the sequence. The base sequence encoding this protein is set out in SEQ ID NO: 7

The amino acid sequence of hCL-L2-2v3 set out in SEQ ID NO: 10 (amino acid position 1-221) represents a protein consisting of 221 amino acids, and thus the base sequence encoding the same (SEQ ID NO: 57) consists of 663 bases. Characteristic amino acid sequences such as those of a collagen-like domain, a CRD domain and the like were present in the sequence. The base sequence encoding this protein is set out in SEQ ID NO: 9.

The amino acid sequence of hCL-L2-1v1 set out in SEQ ID NO: 37 (amino acid position 1-223) represents a protein consisting of 223 amino acids, and thus the base sequence encoding the same (SEQ ID NO: 59) consists of 669 bases. Characteristic amino acid sequences such as those of a collagen-like domain, a CRD domain and the like were present in the sequence. The base sequence encoding this protein is set out in SEQ ID NO: 36.

The amino acid sequence of hCL-L2-1v2 set out in SEQ ID NO: 39 (amino acid position 1-247) represents a protein consisting of 247 amino acids, and thus the base sequence encoding the same (SEQ ID NO: 60) consists of 741 bases.

Characteristic amino acid sequences such as those of a collagen-like domain, a CRD domain and the like were present in the sequence. The base sequence encoding this protein is set out in SEQ ID NO: 38.

The amino acid sequence of hCL-L2-1v2 set out in SEQ ID NO: 41 (amino acid position 1-247) represents a protein consisting of 247 amino acids, and thus the base sequence encoding the same (SEQ ID NO: 61) consists of 741 bases. Characteristic amino acid sequences such as those of a collagen-like domain, a CRD domain and the like were present in the sequence. The base sequence encoding this protein is set out in SEQ ID NO: 40.

Moreover, the amino acid sequence of mCL-L2 set out in SEQ ID NO: 13 (amino acid position 1-271) represents a protein consisting of 271 amino acids, and thus the base sequence encoding the same (SEQ ID NO: 58) consists of 813 bases. Characteristic amino acid sequences such as those of a collagen-like domain, a CRD domain and the like were present in the sequence. The base sequence encoding this protein is set out in SEQ ID NO: 12.

Homologues used herein refer to nucleic acid sequences or amino acid sequences that bear high homology, which are homologous at least 50% or more, preferably 70% or more, more preferably 90% or more. When deletion or insertion is present in the sequence, homologous search may be conducted which allows for gap junction. For example, the search may be performed using a procedure of multiple alignment (trade name: SODHO, Fujitsu Limited). In addition, as the algorithm for searching homology, Smith-Waterman algorithm, which is the most accurate, may be employed. Alternatively, FASTA or BLAST may be also utilized via the Internet.

Mutants used herein include for example, those resulting from allele, Single Nucleotide Polymorphism (SNP) and the like. Furthermore, the nucleic acid sequence of the present invention may also include the mutated nucleic acid sequences derived from the changes in the range of degeneracy of the codon. Partial alteration of the codon of a nucleic acid sequence may be achieved according to a conventional procedure using such site directed mutagenesis methods as those in which a primer is employed consisting of a synthesized oligonucleotide that encodes the desired alteration (Mark, D. F. et al., Proc. Natl. Acad. Sci. USA., 81, 5662, 1984). Thus resultant artificial genetic mutants are also involved in the nucleic acid sequence of the present invention. Furthermore, the mutated amino acid translated by the mutated codon has preferably similar properties to those of normal amino acid even in the case where the mutation is beyond the range of degeneracy of the codon. The mutation may be preferably as follows, which are among amino acids having similar properties, functions, characteristics and the like, for example: the mutation among aliphatic amino acids such as alanine, valine, leucine and isoleucine; the mutation among neutral amino acids such as glycine, alanine, serine, threonine, valine, leucine, isoleucine, cysteine, methionine, phenylalanine, tyrosine, proline, tryptophan, asparagines and glutamine; the mutation among acidic amino acids such as aspartic acid and glutamic acid; the mutation among basic amino acids such as arginine, lysine and histidine; the mutation among serine and threonine, having a hydroxyl group; the mutation among phenylalanine and tyrosine, having an aromatic ring; and the like. These artificially or naturally mutated proteins are also included in the protein of the present invention. For the artificial mutation, site-directed mutagenesis may be caused using a PCR method, or alternatively, other known methods may be used to cause mutation at any optional site.

Modified forms used herein may be prepared using conventional techniques, for example, by acetylation, acylation, ADP-ribosylation, amidation, myristoylation, glycosylation, hydroxylation, phosphorylation, sulfation, formylation, methylation, polyethyleneglycolation, lipid coupling, nucleotide coupling, metal coupling (calcium addition and the like), fusion with other protein (albumin and the like), dimerization, and the like. For example, since glycosylation does not occur when the host is in *Escherichia coli*, the expression may be conducted in eucaryotic cells when glycosylation is intended. Insect cells may be also used because glycosylation proceeds post-translationally in these cells, similarly to in mammalian cells.

Polymorphic variants used herein involve for example, polymorphisms caused by structural or conformational differences in chromosomal DNA, polymorphisms resulting from a change of a gene into its allelic gene, or the like. In general, genes of eucaryotic cells often exhibit polymorphic event, and this event may lead to the substitution of one or more amino acid(s), whilst the activity of the protein may be retained in spite of the substitution. Therefore, any of the genes encoding a protein obtained by artificially modifying the gene encoding any of the amino acid sequence set out in either SEQ ID NO: 2, 4, 6, 8, 10 or 13, 37, 39 or 41, SEQ ID NO: 47 (corresponding to the amino acid position of 113-271 of SEQ ID NO: 2), or in the amino acid position of 113-271 of SEQ ID NO: 13 is involved in the present invention as far as the protein has a characteristic function of a gene according to the present invention. In addition, any of the proteins prepared by artificial modification of amino acid sequence set out in either SEQ ID NO: 2, 4, 6, 8, 10 or 13, 37, 39 or 41, SEQ ID NO: 47 (corresponding to the amino acid position of 113-271 of SEQ ID NO: 2), or in the amino acid position of 113-271 of SEQ ID NO: 13 is involved in the present invention as far as it has a characteristics of a protein according to the present invention. The modification is construed as involving substitution, deletion, addition and/or insertion.

Fragments used herein refer to any optional fragments derived from the amino acid sequence of CL-L2s described above, which may include for example, an extracellular domain, an intracellular domain, a transmembrane domain, a collagen-like domain, a CRD domain, a collectin-like domain, a hydrophobic domain (a transmembrane domain and the like), a hydrophilic domain (domains other than hydrophobic domains), and the like, as well as fragments obtained by the fusion of these fragments.

For example, in the amino acid sequence of hCL-L2-1 set out in SEQ ID NO: 2, exemplary fragments may include: a fragment comprising amino acids of approximately from the position 113 to 271 that form a CRD domain; a fragment comprising amino acids of approximately from the position 41 to 271 that form a CRD domain and a collagen-like domain; and a fragment comprising amino acids of approximately from the position 41 to 112 that form a collagen-like domain. Furthermore, in the amino acid sequence of hCL-L2-2 set out in SEQ ID NO: 4, exemplary fragments may include: a fragment comprising amino acids of approximately from the position 18 to 245 that form a CRD domain and a collagen-like domain, and a fragment comprising amino acids of approximately from the position 18 to 86 that form a collagen-like domain; in the amino acid sequence of hCL-L2-2v1 set out in SEQ ID NO: 6, exemplary fragments may include: a fragment comprising amino acids of approximately from the position 18 to 197 that form a CRD domain and a collagen-like domain, a fragment comprising amino acids of approximately from the position 18 to 38 that form a collagen-like domain; in the amino acid sequence of hCL-L2-

2v2 set out in SEQ ID NO: 8, exemplary fragments may include: a fragment comprising amino acids of approximately from the position 18 to 221 that form a CRD domain and a collagen-like domain, a fragment comprising amino acids of approximately from the position 18 to 62 that form a collagen-like domain; in the amino acid sequence of hCL-L2-2v3 set out in SEQ ID NO: 10, exemplary fragments may include: a fragment comprising amino acids of approximately from the position 18 to 221 that form a CRD domain and a collagen-like domain, a fragment comprising amino acids of approximately from the position 18 to 62 that form a collagen-like domain. Moreover, in the amino acid sequence of hCL-L2-1v1 set out in SEQ ID NO: 37, exemplary fragments may include: a fragment comprising amino acids of from the position approximately 41 to 223 that form a CRD domain and a collagen-like domain, a fragment comprising amino acids of approximately from the position 41 to 64 that form a collagen-like domain; in the amino acid sequence of hCL-L2-1v2 set out in SEQ ID NO: 39, the fragments included may be: a fragment comprising amino acids of approximately from the position 41 to 247 that form a CRD domain and a collagen-like domain, a fragment comprising amino acids of approximately from the position 41 to 88 that form a collagen-like domain; in the amino acid sequence of hCL-L2-1v3 set out in SEQ ID NO: 41, exemplary fragments may include: a fragment comprising amino acids of approximately from the position 41 to 247 that form a CRD domain and a collagen-like domain, a fragment comprising amino acids of approximately from the position 41 to 88 that form a collagen-like domain. Additionally, in the amino acid sequence of mCL-L2 set out in SEQ ID NO: 13, exemplary fragments may also include: a fragment comprising amino acids of approximately from the position 113 to 271 that form a CRD domain; a fragment comprising amino acids of approximately from the position 41 to 271 that form a CRD domain and a collagen-like domain; and a fragment comprising amino acids of approximately from the position 41 to 112 that form a collagen-like domain.

Process for Obtaining CL-L2s Gene

A CL-L2s gene according to the present invention may be those obtained through any processes. For example, the base sequence encoding CL-L2s of the present invention can be obtained by preparing mRNA from the cells that are expressing the protein, and converting it into a double stranded DNA by a conventional technique. For the preparation of mRNA, guanidine isothiocyanate calcium chloride method (Chirwin, et al., Biochemistry, 18, 5294, 1979) and the like can be employed. For the preparation of poly(A)$^+$ RNA from total RNA, supports bound with oligo(dT), for example, affinity chromatography in which sepharose or latex particles are used, can be employed. Double stranded cDNA can be obtained by using thus obtained RNA described accordingly as a template to treat with reverse transcriptase, using oligo (dT) that is complementary to poly(A) chain present at 3'-terminus, or a random primer or a synthesized oligonucleotide corresponding to a part of the amino acid sequence of CL-L2s as a primer (Mol. Cell. Biol., 2, 161, 1982; Mol. Cell. Biol., 3, 280, 1983; Gene, 25, 263, 1983); and by treating thus resulting cDNA strand with for example, *E. coli* RNaseH, *E. coli* DNA polymerase 1, *E. coli* DNA ligase to alter into the DNA strand. A cDNA library can be produced by incorporating this cDNA into a plasmid vector, a phage vector or a cosmid vector to transform *E. coli*, or by transfecting it into *E. coli* following in vitro packaging.

The plasmid vector that can be used herein is not particularly limited as long as it can be replicated and maintained in the host. Phage vector is not also particularly limited as long as it can proliferate in the host. Cloning vectors include, for example, pBR322, pUC19, λgt10, λgt11 and the like. Moreover, upon subjecting to immunological screening, the vector has preferably a promoter that enables the expression of a CL-L2s gene in the host.

To incorporate cDNA into a plasmid, the process of Maniatis et at (Molecular Cloning, A Laboratory Manual, second edition) and the like can serve as a reference. Further, to incorporate cDNA into a phage vector, the process disclosed in Hyunh et at (DNA cloning, a practical approach, 1, 49, 1985) and the like can serve as a reference.

As the process for introducing the expression vector described above into host cells, methods for example, transfection by lipopolyamine method, DEAE-dextran method, Hanahan method, lipofectin method, calcium phosphate method; microinjection, and electroporation and the like (Molecular Cloning, A Laboratory Manual, second edition) may be involved. In vitro packaging can be readily effected by using commercially available kits (manufactured by Stratagene, or Amersham).

The process for the isolation of cDNA encoding a CL-L2s protein from a cDNA library prepared as described above may involve a general process, which may be used in combination, for the screening of cDNA. For example, a probe labeled with $^{32}$P is produced, and a clone containing the desired cDNA can be screened by a colony hybridization method (Proc. Natl. Acad. Sci. USA, 72, 3961, 1975), or a plaque hybridization method (Molecular Cloning, A Laboratory Manual, second edition, Cold Spring Harbor Laboratory, 2, 108, 1989). Further, a clone may be selected by a PCR method. Additionally, the desired clone can be selected through the use of an antibody that recognizes CL-L2s when a cDNA library is produced using a vector that can express cDNA.

Furthermore, when a CL-L2s gene is isolated from cells that express CL-L2s gene, for example, the expressing cells are dissolved using SDS or proteinase K, followed by a phenol treatment. Unwanted RNA is digested with ribonuclease. Thus resultant DNA is digested with restriction enzyme, and the resulting DNA fragments are amplified using phage or cosmid to produce a library. Thereafter, the desired clone is selected, and then a CL-L2s gene can be obtained.

The base sequence of the DNA obtained accordingly can be determined by a Maxam-Gilbert method (Proc. Natl. Acad. Sci. USA, 74, 560, 1977) or a Sanger's method (Proc. Natl. Acad. Sci. USA, 74, 5463, 1977). The CL-L2s gene can be obtained by excising from the clone as obtained above.

Through use of the primer synthesized on the basis of the base sequence of CL-L2, cloning can be also effected by a RT-PCR method using poly(A)$^+$ RNA of the cells expressing CL-L2s as a template. Further, the desired cDNA can be also obtained by directly screening the cDNA library after producing/synthesizing a probe based on the base sequence of CL-L2s, not by way of the PCR. The gene of the present invention can be selected among the genes obtained by the methods described herein above through the verification of the base sequence of the gene. The gene of the present invention can be also produced according to the conventional process in which chemical synthesis of a nucleic acid, e.g., phosphoimidite method (Mattencci, M. D. et al., J. Am. Chem. Soc., 130, 3185, 1981) or the like, is employed.

Process for Producing Expression Vector

The present invention also relates to a vector comprising a nucleic acid sequence of CL-L2s. The vector is not particularly limited so far as it can express the CL-L2s protein, however, a plasmid vector, an RNA vector, a DNA vector, a virus vector, a phage vector and the like may be employed.

Specifically, examples thereof include pBAD/His, pRSETA, pcDNA2.1, pTrcHis2A, pYES2, pBlueBac4.5, pcDNA3.1 or pSecTag2 manufactured by Invitrogen, pET or pBAC manufactured by Novagen Co., pGEM manufactured by Promega, pBluescriptII, pBs, Phagescript, pSG or pSV2CAT manufactured by Stratagene, or pGEX, pUC18/19, pBPV, pSVK3 or pSVL manufactured by Pharmacia Co.

The cDNA sequence of CL-L2s ligated to the expression vector is operatively linked to a promoter. The promoter includes for example, phage λPL promoter, E. coli lac, trp, tac promoter, SV40 early and late promoter, T7 and T3 promoter, retrovirus LTR promoter. Specifically, the prompter for use in eukaryotic cells include CMV promoter, HSV promoter, SV40 early and late promoter, retrovirus LTR promoter, RSV promoter, metallothionein promoter. In addition, the expression vector may contain a marker to allow the selection of the transformed host, and an enhancer. Examples of the marker include dihydrofolate reductase gene, neomycin resistant gene, ampicillin resistant gene and the like. Examples of the enhancer include SV40 enhancer, cytomegalovirus early enhancer promoter, adenovirus enhancer and the like.

Process for Producing Transformed Cells

The present invention further provides transformed cells carrying a base sequence of the present invention to allow the expression thereof by means of the vector as described above that is carrying the base sequence. The host cell for use as a transformed cell in the present invention may preferably include animal cells and insect cells, however, included may be all of the cells (microorganisms may be also included), which can express a CL-L2s protein in the expression vector of the present invention.

Exemplary animal cells or insect cells of the present invention may respectively include cells derived from human, or cells derived from fly or silkworm (Bombyx mor). For example, CHO cells, COS cells, BHK cells, Vero cells, myeloma cells, HEK293 cells, HeLa cells, Jurkat cells, mouse L cells, mouse C127 cells, mouse FM3A cells, mouse fibroblast, osteoblast, chondrocyte, S2, Sf9, Sf21, High Five™ cells may be included. The microorganism according to the present invention include *Escherichia coli, Saccharomyces cerevisiae* and the like. For the introduction of a vector into such hosts, the method as described above may be employed.

The cells expressing CL-L2s of the present invention can be used for analyzing a collectin pathway involving in infectious diseases, immunity and the like. Further, those cells can be utilized in manufacturing a CL-L2s protein or a CL-L2s protein having a carbohydrate chain. The cells can also be utilized in screening for the purpose of obtaining an agonist or an antagonist to the CL-L2s protein.

Process for Obtaining Protein

The present invention also relates to a process for the production of a CL-L2s protein which comprises culturing a cell transformed with the base sequence of the present invention as set forth above, and harvesting thus produced CL-L2s. Cell culture, isolation of the protein, and purification thereof may be carried out with conventionally known processes.

The protein according to the present invention can be expressed as a recombinant fusion protein, which can be readily isolated, purified, and recognized per se. The recombinant fusion protein is a protein expressed by adding an appropriate peptide chain to the N-terminal end and/or C-terminal end of a protein expressed from a nucleic acid sequence encoding the desired protein. In order to facilitate the purification of the expressed protein, the protein may be expressed as a fusion protein having a signal for extracellular secretion. In addition, the protein can be obtained from several kinds of sources such as cultured cells, cultured tissues, transformed cells and the like using conventionally known methods, for example, known purification methods including: salting out such as ammonium sulfate precipitation technique and the like; gel filtration technique using Sephadex and the like; ion exchange chromatographic technique; hydrophobic chromatographic technique; dye gel chromatographic technique; electrophoresis technique; dialysis; ultrafiltration technique; affinity chromatographic technique; high performance liquid chromatographic technique; and the like.

Process of the Utilization of Gene

Probes for detecting CL-L2s gene can be specified on the basis of the base sequence set out in either SEQ ID NO: 1, 3, 5, 7, 9, 12, 36, 38 or 40, SEQ ID NO: 48 (corresponding to the base position of 601-1077 of SEQ ID NO: 1) or in the nucleic acid position of 493-969 of SEQ ID NO: 12. Alternatively, primers can be specified for the amplification of DNA or RNA including such a base sequence. To specify a probe or a primer based on a given sequence is ordinarily carried out by those skilled in this art. An oligonucleotide having a specified base sequence can be obtained through chemical synthesis. When a suitable label is added to the oligonucleotide, it can be utilized for hybridization assay in several formats. Alternatively, it can be also utilized in reactions for synthesis of nucleic acids such as PCR. The oligonucleotide that is utilized as a primer is of at least 10 bases in length, and suitably of 15 to 50 bases in length. It is desirable that the oligonucleotide that is used as a probe be of from 100 bases to its full length. Further, they can be also used for the diagnosis of diseases caused by mutation of a CL-L2s gene because they can be used for detecting genetic mutation encoding a CL-L2s protein and for detecting SNP. They are expected to be available for the diagnosis of a variety of diseases including for example, bacterial infections and the like. In addition, they are also useful for gene therapy whereby CL-L2s gene is introduced into a living body to allow the expression thereof.

Moreover, it is also possible to obtain a promoter region and an enhancer region of the CL-L2s gene that is present in a genome, based on a cDNA base sequence of CL-L2s provided by the present invention. In particular, these control regions can be obtained by similar methods to those disclosed in Japanese unexamined patent publication No. 6-181767; J. Immunol., 155, 2477, 1995; Proc. Natl. Acad. Sci, USA., 92, 3561, 1995, and the like. Promoter region referred to herein means a DNA region which controls the expression of a gene that exists upstream of a transcription initiation site. Enhancer region herein refers to a DNA region that enhances the expression of a gene that exists in an intron, a 5'-untranslated region, or a 3'-untranslated region.

Process of the Utilization of Protein

CL-L2s proteins of the present invention can be utilized in the elucidation of mechanisms of fundamental immunity; in the elucidation of mechanisms of the development of a wide variety of diseases such as bacterial infections; in the diagnostic, prophylactic and therapeutic methods thereof; and for the development of reagents and drugs for the same. Furthermore, they can be used as an antigen for producing antibodies to CL-L2s. Additionally, they can be utilized in the screening processes of an agonist or an antagonist.

Agonist and Antagonist

The present invention also relates to agonists which stimulate the activity or the activation of CL-L2s of the present invention. In addition, the present invention also relates to antagonists which inhibit the activity or the activation of CL-L2s of the present invention. For screening the antagonist, a competitive experimental system can be used, for example, in which mannose or an antibody, and a candidate inhibitor are subjected to the interaction with cells expressing CL-L2s protein thereby allowing the candidate inhibitor to screen based on the binding ratio to mannose. Otherwise, conventionally known methods may also be carried out to effect the screening. Further, the antagonists also include antisense nucleic acids that inhibit the expression of CL-L2s gene. Included in the examples of the other methods for the screening may be methods in which a change in extracellular pH is measured, which is caused by the activation of a receptor (Science, 246, 181-296, 1989), and the like.

Transgenic Non-Human Animal

The present invention relates to transgenic non-human animals having an altered expression level of CL-L2s gene. CL-L2s gene herein includes cDNA, genomic DNA or synthesized DNA encoding hCL-L2s or mCL-L2s. For expression of a gene, any one of the steps of transcription and translation should be comprised. The transgenic non-human animals according to the present invention are useful for the investigation of functions or expression mechanisms of CL-L2, elucidation of mechanisms of diseases that are anticipated to be involved in CL-L2s, development of diseased animal models for use in screening and safety tests of pharmaceutical products.

In the present invention, the gene can be artificially modified to increase or decrease the expression level in comparison with the native expression level of the gene by introducing mutation such as deletion, substitution, addition and/or insertion into a part of some key sites (enhancer, promoter, intron or the like) that regulate the expression of the gene to be proper. The introduction of the mutation can be carried out by known methods to obtain a transgenic animal.

Transgenic animals in their narrow means refer to animals having germ cells into which a foreign gene was artificially introduced by a genetic recombination technique. In their broader means, they include: antisense transgenic animals having a particular gene of which function was suppressed using an antisense RNA; knockout animals having a particular gene knocked out using embryonic stem cells (ES cell); and animals having point mutation of DNA introduced, all of which are animals having a chromosome with a foreign gene being stably introduced therein at an early stage of the development of the individual, and having a genotype that can be transmitted to the progeny thereof.

Transgenic animals referred to herein should be comprehended in their broader means including all vertebrates other than human. The transgenic animals according to the present invention are useful for the investigation of functions or expression mechanisms of CL-L2s, elucidation of mechanisms of diseases that are involved in cells expressed in human, development of diseased animal models for use in screening and safety tests of pharmaceutical products.

Process for producing a transgenic mouse may include: a process in which a gene is directly introduced into a nucleus of an ovum in a anterior nucleus phase with a micropipette under a phase contrast microscope (microinjection technique, U.S. Pat. No. 4,873,191); a process in which embryonic stem cells (ES cells) are used. Alternatively, a process in which a gene is introduced into a retrovirus vector or an adenovirus vector followed by infection into an ovum; a sperm vector technique in which a gene is introduced into an ovum via a sperm; and the like have been developed.

The sperm vector technique is a genetic recombinant process in which a foreign gene is attached to a sperm, or a foreign gene is introduced into a sperm cell with an electroporation technique, and then the foreign gene is introduced into an ovum by fertilizing the ovum (M. Lavitranoet et al., Cell, 57, 717, 1989). Alternatively, site directed genetic recombination in vivo may be also employed by a cre/loxP recombinase system of bacteriophage P1, a FLP recombinase system of Saccharomyces cerevisiae, or the like. Additionally, a process has been also reported in which a transgene of a desired protein is introduced into a non-human animal using retrovirus.

Process for the production of a transgenic animal with a microinjection technique is carried out as described below, for example.

First, a transgene is required, which is substantially constituted from a promoter involved in expression control, a gene encoding a specified protein, and a poly(A) signal. The manner of the expression and/or the expression level of a specified molecule may be affected by the promoter activity. In addition, because transgenic animals are different among the produced lineages in respect to the number of the copies of the introduced transgene, or the introduced site in the chromosome, the manner of the expression and/or the expression level must be confirmed for each of the lineages. Since it has been elucidated that the expression level is altered depending on the untranslated region or splicing, an intron sequence to be spliced at a preceding site of poly (A) signal may be previously introduced. It is important to use a gene, which is introduced into a fertilized ovum, has as high purity as possible. The animal to be used may include mice for use in collecting fertilized ova (5-6 weeks old), male mice for use in mating, female pseudopregnant mice, vas deferens ligated male mice, and the like.

In order to efficiently obtain the fertilized ova, gonadotropin or the like may be used for inducing the ovulation. The fertilized ova are harvested, and thereafter, a gene in an injection pipette is introduced into a male pronucleus of the ovum by a microinjection technique. An animal (a pseudopregnant mouse or the like) for use in repositioning the injected ova to an oviduct is provided, to which 10-15 ova are transplanted per one animal. Thereafter, the born mouse can be examined for the introduction of the transgene by: extracting genomic DNA from the end portion of the tail; and detecting the transgene by a Southern method or a PCR technique, alternatively by a positive cloning technique where a marker gene is inserted which is activated upon only the occurrence of homologous recombination. Moreover, in order to ascertain the expression of the transgene, a transcription product derived from the transgene is detected by a Northern method or a RT-PCR technique. Alternatively, a western blotting method may be carried out with a specific antibody to the protein or a fragment thereof.

Knockout Mouse

The knockout mouse according to the present invention is one that was treated in a manner to deprive the function of CL-L2s gene. Knockout mouse refers to a transgenic mouse in which an arbitrary gene is destroyed by a homologous recombination technique to impair the corresponding function. The knockout mouse can be produced by homologous recombination using ES cells, followed by the selection of the embryonic stem cell having one of the allelic gene altered/destroyed. A chimeric mouse, which carry cells derived from the embryonic stem cells and cells derived from the embryo being mixed, may be obtained by, for example, injecting the embryonic stem cell that had been genetically engineered at blastocyst stage or morulae stage of the fertilized ovum. When this chimeric mouse (chimera refers to a single individual built-up with somatic cells on the basis of more than two fertilized ova) is crossbred with a normal mouse, a heterozygotic mouse can be produced having one of the allelic gene is entirely altered/destroyed. Further, a homozygotic mouse can be produced by crossbreeding heterozygotic mice each other.

Homologous recombination refers to the recombination that is caused by a mechanism of genetic recombination between two genes having identical or extremely similar base sequences. For the selection of cells with the homologous recombination, PCR can be employed. PCR reaction, in which primers corresponding to a part of the inserted gene and a part of the region expected to be inserted are used, may be carried out to reveal the homologous recombination occurring in cells that could yield the amplification products. Also, when the homologous recombination is caused to a gene expressed in embryonic stem cells, the gene to be introduced may be joined to a neomycin resistant gene to allow the selection after the introduction into cells by making them resistant to neomycin. Accordingly, known methods and the modified methods thereof can be employed to enable the easy selection.

Process for Producing Antibodies

The present invention further provides antibodies that recognize CL-L2s or fragments thereof. The antibodies in accordance with the present invention include for example, the antibodies to a protein comprising an amino acid sequence set out in SEQ ID NO: 2, 4, 6, 8, 10, 13, 37, 39 or 41, SEQ ID NO: 47 (corresponding to the amino acid position of 113-271 of SEQ ID NO: 2), or in the amino acid position of 113-271 of SEQ ID NO: 13, or a fragment thereof. The antibodies (e.g., polyclonal antibodies, monoclonal antibodies, peptide antibodies) or antisera to CL-L2s or a fragment thereof can be produced using CL-L2s or a fragment thereof of the present invention as an antigen according to any process for producing the antibodies or antisera which is known per se. In particular, antibodies that can control the function of CL-L2s (e.g., antibodies that recognize CRD, a collagen like domain and the like) are useful for pharmaceutical products containing the antibody.

CL-L2s or a fragment thereof according to the present invention may be administered neat or with a diluent or a carrier to a warm-blooded animal at a site that enables the production of the antibody upon the administration. In order to facilitate the production of antibodies upon the administration, complete Freund's adjuvant or incomplete Freund's adjuvant may be administered. The administration may be usually conducted once per 1 to 6 weeks, and two to ten times in total. The warm-blooded animal used may include for example, monkey, rabbit, dog, guinea pig, mouse, rat, sheep, goat, chicken, and the like. Among these, mouse and rat may be preferably used. Rat that may be preferably used includes Wistar and SD strain rat, and mouse that may be preferably used includes BALB/c, C57BL/6 and ICR strain mouse and the like.

Upon the production of cells that produce a monoclonal antibody, an individual with the antibody titer that can be recognized therein is selected from the warm-blooded animals e.g., mice that had been immunized with an antigen. On two to five days after final immunization, spleen or lymph node is collected, and the antibody producing cells contained therein are subjected to the fusion with myeloma cells to effect the preparation of monoclonal antibodies producing cells. The determination of the antibody titer in the antiserum may be carried out for example, by subjecting a labeled CL-L2s described below to a reaction with the antiserum, and thereafter measuring the activity of the label bound to the antibody. The fusion operation can be performed in accordance with a known technique for example, the process of Köhler and Milstein (Nature, 256, 495, 1975) and the modified process thereof (J. Immunol. Method, 39, 285, 1980; Eur. J. Biochem., 118, 437, 1981; Nature, 285, 446, 1980). Examples of the fusion accelerating agent may include polyethylene glycol (PEG), Sendai virus and the like, and polyethylene glycol may be preferably used. In addition, lectin, poly-L-lysine or DMSO may be added ad libitum to raise the efficiency of the fusion.

Examples of the myeloma cell include X-63Ag8, NS-1, P3U1, SP2/0, AP-1 and the like, and SP2/0 may be preferably used. The ratio of antibody producing cell (spleen cell) number to myeloma cell number preferably used is 1:20-20:1. PEG (preferably, PEG 1000-PEG6000) is added at approximately 10-80%. The fusion mixture is incubated at 20-40° C., preferably at 30-37° C. for 1-10 min. Such a condition enables efficient cell fusion. Screening of the hybridoma that produces anti-CL-L2s antibody may be performed by using various methods, which include for example, a process in which a supernatant of hybridoma culture is added to a solid phase (e.g., a microplate) adsorbed with CL-L2s antigen directly or with a carrier, and then an anti-immunoglobulin antibody (when the cells used for the cell fusion was derived from a mouse, anti-mouse immunoglobulin antibody may be used) that was labeled with a radioactive substance, enzyme or the like, or protein A is added thereto thereby detecting the anti-CL-L2s antibody bound to the solid phase; or a process in which a supernatant of hybridoma culture is added to a solid phase adsorbed with an anti-immunoglobulin antibody or protein A, and then CL-L2s labeled with a radioactive substance, enzyme or the like is added thereto thereby detecting the anti-CL-L2s monoclonal antibody bound to the solid phase.

Selection and cloning of the anti-CL-L2s antibody can be carried out by known methods per se, or the modified methods thereof. Usually, the process is carried out in a medium for animal cells added with HAT (hypoxanthine, aminopterin, thymidine). The medium for use in the selection, cloning and growing may be any one of the media in which hybridoma can grow. For example, RPMI medium containing 1-20%, preferably 10-20% of fetal bovine serum, GIT medium containing 1-10% of fetal bovine serum, or serum free medium for hybridoma culture, and the like. The temperature of the culture may be preferably about 37° C. The culture period may be usually five days to three weeks, preferably one week to two weeks. The culture is usually conducted in the presence of 5% carbon dioxide gas. The antibody titer of the supernatant of the hybridoma culture can be measured in a similar manner to the measurement of the antibody titer of anti-CL-L2s antibody in an antiserum as described above. In other words, a radioimmunoassay (RIA) technique, an enzyme linked immunosorbent assay (ELISA) technique, a FIA (fluorescent immunoassay) technique, a plaque measurement technique, an agglutination reaction technique and the like may be employed as the measurement process, however, the ELISA technique as described below is preferred.

The screening by an ELISA technique can be carried out in accordance with the following procedure. A protein, which was prepared by a similar process to that for the immunoantigen, is immobilized on the surface of each well of an ELISA plate. Next, BSA, MSA, OVA, KLH, gelatin or skimmed milk or the like is immobilized for the purpose of preventing non-specific adsorption. To each well of this plate added with a supernatant solution of the hybridoma culture, followed by allowing the immunoreaction by standing for a predetermined time. Each well is washed using a washing solution such as PBS or the like. Surfactant may be preferably added to this washing solution. An enzyme-labeled secondary antibody is added, and the mixture is allowed to stand for a predetermined time. The enzyme for labeling which can be used includes β-galactosidase, alkaline phosphatase, peroxidase and the like. After the washes with the same washing solution, enzyme reaction is effected through adding a substrate solution of the labeled enzyme that was employed. When the desired antibody is present in the added supernatant solution of the hybridoma culture, the enzyme reaction proceeds to change the color of the substrate solution.

Cloning can be usually carried out by known methods per se, such as a semisolid agar technique, a limiting dilution technique or the like. Specifically, after the well in which the desired antibody is produced is confirmed by the process described above, a single clone is obtained through conducting the cloning. The process for cloning may involve a limiting dilution technique or the like, in which hybridoma cells are diluted so that one colony per one well of a culture plate is formed, and thereafter the culture is conducted. Cloning by a limiting dilution technique may be performed through the use of feeder cells in order to elevate the colony formation ability, otherwise, a cell growth factor such as interleukin 6 may be added thereto. Alternatively, FACS and single cell manipulation techniques can be employed for the cloning. The cloned hybridoma is cultured preferably in a cell free medium, and an appropriate amount of the antibody is added to the supernatant thereof. Thus resulting single hybridoma may be subjected to a large scale culture using a flask or a cell culture equipment, or may be cultured in the peritoneal cavity of an animal (J. Immunol. Meth., 53, 313, 1982) to give a monoclonal antibody. When the culture is conducted in a flask, a medium for cell culture (IMDM, DMEM, RPMI 1640, MEM and the like) containing 0-20% of FCS can be used. When the culture is conducted in the peritoneal cavity of an animal, an animal of the same species, and the same strain as the animal from which myeloma cells derived that were used for the cell fusion; otherwise an athymic nude mouse may be preferably used. Hybridoma is transplanted after mineral oil such as pristine or the like is previously administered to the animal. Ascites containing the monoclonal antibody can be obtained after one to two weeks passed, when the myeloma cells enough proliferate.

The monoclonal antibody of the present invention can be obtained as the antibody, which does not cross-react with other proteins, by selecting one which recognizes an epitope specific for CL-L2s. In general, an epitope, which is presented by serial amino acid residues of at least more that or equal to five, preferably 7 to 20 amino acids among the amino acid sequence constituting the protein, is referred to as an epitope inherent in the protein. Therefore, the monoclonal antibody that recognizes an epitope constituted from a peptide having an amino acid sequence, which were selected from the protein comprising an amino acid set out in any of SEQ ID NO: 2, 4, 6, 8, 10, 13, 37, 39 or 41, SEQ ID NO: 47 (corresponding to the amino acid position of 113-271 of SEQ ID NO: 2), or in the amino acid position of 113-271 of SEQ ID NO: 13, and consisting of at least five serial amino acid residues may be identified as the monoclonal antibody specific to hCL-L2s or mCL-L2s according to the present invention. When an amino acid sequence is chosen which is conserved among the amino acid sequence set out in SEQ ID NO: 2, 4, 6, 8, 10, 13, 37, 39 or 41, an epitope common to CL-L2s can be selected. Alternatively, a monoclonal antibody can be selected which enables the discrimination of each protein, with a region including an amino acid sequence specific for each of the sequences.

The separation and purification of anti-CL-L2s monoclonal antibody can be carried out according to the separation and purification process of an immunoglobulin similarly to the usual separation and purification process of the polyclonal antibodies. Known purification process which can be adopted may include for example, a salt precipitation technique, an alcohol precipitation technique, an isoelectric point precipitation technique, an electrophoretic technique, an ammonium sulfate precipitation technique, an adsorption/desorption technique by an ion exchanger (e.g., DEAE), an ultracentrifugation technique, a gel filtration technique, and a specific purification technique in which an antibody alone is collected by an antigen-bound solid phase or an active adsorbent such as protein A or protein G, or the like, followed by dissociation of the binding to give the antibody. For the purpose of preventing the formation of aggregates, or the decrease in the antibody titer in the purification step, for example, human serum albumin may be added at a concentration of 0.05-2%. Otherwise, amino acids such as glycine, α-alanine and the like, in particular, basic amino acid such as lysine, arginine, histidine and the like, saccharides such as glucose, mannitol and the like, salts such as sodium chloride may be also added. In the case of IgM, which is known to be liable to agglutinate, it may be treated with β-propionolactone and acetic anhydride.

The polyclonal antibody according to the present invention can be produced by known methods per se, or the modified methods thereof. For example, to produce a polyclonal antibody, an immunoantigen (a protein antigen) itself or a complex, which was formed with the immunoantigen and a carrier protein, is used for the immunization of a warm-blooded animal in a similar manner to the process for producing the monoclonal antibody described above, followed by collecting the preparation containing the antibody to the protein of the present invention or a fragment thereof from the warm-blooded animal, and then the antibody is purified/isolated. In respect to the complex of an immunoantigen and a carrier protein for use in the immunization of the warm-blooded animal, the kind of the carrier protein and the mixing ratio of the carrier and hapten may be optionally determined as long as the antibody can be efficiently produced to the hapten subjected to the immunization after crosslinking with the carrier. Thus, any kind of the carrier protein may be crosslinked at any ratio, however, the process in which about 0.1-20, preferably about 1-5 of bovine serum albumin, bovine thyroglobulin, hemocyanin or the like, for example, is coupled with 1 of hapten by weight may be used. In addition, various condensing agents may be used for the coupling of the hapten and carrier, which may include glutaraldehyde and carbodiimide, and active ester reagents containing maleimide active ester, thiol group, dithiopyridyl group and the like. The condensation product is administered neat or with a carrier or a diluent to a warm-blooded animal at a site that enables the production of the antibody upon the administration. In order to facilitate the production of antibodies upon the administration, complete Freund's adjuvant or incomplete Freund's adjuvant may be administered. The administration may be usually conducted once per 2 to 6 weeks, and three to ten times in total. Polyclonal antibodies can be collected from the blood, ascites and the like, and preferably from the blood, of the warm-blooded animal immunized by a process as described above. The measurement of the antibody titer in antiserum can be carried out in a similar manner to the measurement of the antibody titer of the antiserum as described above. The separation and purification of the polyclonal antibody can be carried out according to the separation and purification process of an immunoglobulin similarly to the separation and purification process of a monoclonal antibody described above.

Process of the Utilization of Antibody

Monoclonal antibodies and polyclonal antibodies to CL-L2s or a fragment thereof can be utilized in diagnosis and therapy of the diseases relating to the cells that are expressing CL-L2s. CL-L2s or a fragment thereof can be measured using these antibodies, on the basis of the immunological binding with CL-L2s or the fragment thereof according to the present invention. Specifically, the process for measuring CL-L2s or a fragment thereof using such an antibody may include for example, sandwich techniques in which a sandwich complex is detected which was produced by subjecting CL-L2s or a fragment thereof to a reaction with an antibody coupled to an insoluble support and a labeled antibody; or competitive techniques in which CL-L2s or a fragment thereof in a sample is measured by subjecting labeled CL-L2s, and CL-L2s or a fragment thereof in a sample to a competitive reaction with the antibody followed by the measurement of CL-L2s or a fragment thereof in a sample from the amount of the labeled antigen that reacted with the antibody.

Upon the measurement of CL-L2s or a fragment thereof by the sandwich technique, two-step methods in which CL-L2s or a fragment thereof is first subjected to a reaction with an immobilized antibody; thereafter, unreacted materials are completely removed by washes; and then a labeled antibody is added thereto to have the immobilized antibody—CL-L2s labeled antibody formed, alternatively, one-step methods in which an immobilized antibody, a labeled antibody and CL-L2s or a fragment thereof are mixed concurrently.

Insoluble support for use in the measurement include for example, synthetic resin such as polystyrene, polyethylene, polypropylene, polyvinyl chloride, polyester, polyacrylic acid ester, nylon, polyacetal, fluorine-contained resin and the like; polysaccharides such as cellulose, agarose and the like; glasses; metals; and the like. The insoluble support may be in a variety of forms, and for example, tray-like, spherical, fibrous, cylindrical, discal, vessel-like, cell-like, tubular, and the like may be adopted. The support onto which the antibody had been adsorbed may be stored ad libitum in cold, in the presence of an antiseptic agent such as sodium azide and the like.

For the immobilization of the antibody, known chemical coupling processes or physical adsorption processes may be adopted. Chemical coupling process includes for example, processes in which glutaraldehyde is used; maleimide processes in which N-succinimidyl-4-(N-maleimidemethyl)cyclohexane-1-carboxylate and N-succinimidyl-2-maleimide acetate and the like are used; carbodiimide processes in which 1-ethyl-3-(3-dimethylaminopropyl) carbodiimide hydrochloride and the like is used. Other process includes maleimidebenzoyl-N-hydroxysuccinimide ester processes, N-succimidyl-3-(2-pyridylthio) propionic acid processes, bisdiazobenzidine processes, dipalmityl lysine processes. Alternatively, a complex that had been formed previously by subjecting the substance to be detected to a reaction with two kinds of antibodies of which epitopes are different can be captured by the third antibody to the antibody, which had been immobilized in a similar manner to those described above.

The material to be used for labeling may include enzyme, fluorescent materials, luminescence materials, radioactive materials, metal chelates and the like. Examples of enzyme may include peroxidase, alkaline phosphatase, β-D-galactosidase, malate dehydrogenase, *staphylococcus* nuclease, delta-5-steroid isomerase, α-glycerolphosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholine esterase and the like. Fluorescent materials may include for example, fluorescein isothiocyanate, phycobilin protein, rhodamine, phycoerythrin, phycocyanin, allophycocyanin, orthophthalic aldehyde and the like. Luminescence materials may include isoluminol, lucigenin, luminol, aromatic acridinium esters, imidazole, acridinium salts and modified esters thereof, luciferin, luciferase, aequorin and the like. Radioactive materials may include $^{125}I$, $^{127}I$, $^{131}I$, $^{14}C$, $^{3}H$, $^{32}P$, $^{35}S$ and the like. These materials are not limited thereto as long as the material can be used in immunological determination methods. In addition, low molecular weight hapten such as biotin, dinitrophenyl, pyridoxal or fluorescamine may be conjugated to the antibody. Preferably, horseradish peroxidase may be used as a labeling enzyme. This enzyme can react with many kinds of substrates, which can be readily conjugated to the antibody by a periodic acid method.

When an enzyme is used as a labeling agent, a substrate for measuring its activity, and a color-developing agent as needed may be employed. When peroxidase is used as an enzyme, $H_2O_2$ may be used as a substrate solution, and 2,2'-azino-di-[3-ethylbenzthiazolin sulfonate] ammonium (ABTS), 5-aminosalicylic acid, orthophenylenediamine, 4-aminoantipyrine, 3,3',5,5'-tetramethylbenzidine or the like may be used as a color-developing agent. When alkaline phosphatase is employed as an enzyme, orthophenylphosphate, paranitrophenylphosphate or the like may be used as a substrate. Alternatively, when β-D-galactosidase is used as an enzyme, fluorescein-di-(β-D-galactopyranoside), 4-methyl-umbelliferyl-β-D-galactopyranoside, or the like may be used as a substrate. The present invention also involves kit products including a monoclonal antibody, a polyclonal body described above, and reagents.

Available crosslinking agents include N,N'-orthophenylenedimaleimide, 4-(N-maleimidemethyl)cyclohexanoyl N-succinimide ester, 6-maleimidehexanoyl N-succinimide ester, 4,4'-dithiopyridine, and other known crosslinking agents. The reaction of such a crosslinking agent with the enzyme and the antibody may be conducted in accordance with known methods depending upon the properties of the respective crosslinking agents. Additionally, the antibodies to be used may be any fragments of the antibodies for example, Fab', Fab, $F(ab')_2$ depending on the condition. Furthermore, enzymatically labeled antibodies may be prepared by using a similar process to any one of those for polyclonal antibodies and monoclonal antibodies. When the enzymatically labeled antibody that was obtained by using the aforementioned crosslinking agent is purified by any known methods such as affinity chromatography or the like, more sensitive immunological determination system can be achieved. The enzymatically labeled antibody, which was purified in such a manner, is stored in a cold and dark place after adding thimerosal, glycerol or the like as a stabilizer, alternatively, after being lyophilized.

The subject sample for the measurement may be a sample containing CL-L2s, which may include body fluids such as plasma, serum, blood, urine, tissue fluid, cerebrospinal fluid and the like, various types of cells, tissues, and the like.

Process for Producing Humanized Antibody

It is ethically impermissible to produce antibodies by immunizing human with an optional antigen. Further, when a mouse monoclonal antibody is administered to a human body, there is a risk of the occurrence of a variety of adverse effects, because the antibody is a heterogeneous protein to human. Therefore, an antibody with lowered antigenicity to human is preferred when the antibody is administered to human.

Process for the production of human monoclonal antibodies involves transformation techniques with Epstein-Barr virus (EBV), and fusion techniques in which thus transformed cells and parent cells are fused; processes in which a chimeric antibody or a humanized antibody is produced using genetic engineering techniques; and the like in addition to cell fusion techniques. Chimeric antibody refers to an antibody that was produced by linking immunoglobulin gene fragments from heterogeneous animals. Humanized antibody refers to an antibody having a substituted primary structure in part other than a complementarity determining region (CDR) of H chain and L chain with the corresponding primary structure of a human antibody through introducing the alteration to a mouse antibody or the like that is heterogeneous to human.

For the production of a chimeric antibody, a mouse is immunized first, and an antibody variable region (V region) that binds to an antigen is excised from a gene of the mouse monoclonal antibody. Thereafter, the V region is linked to a gene of an antibody constant region (C region) derived from human myeloma to give a chimeric gene. Upon expression of this chimeric gene in a host cell, human-mouse monoclonal antibody can be produced. Because chimeric antibodies are less antigenic to human, they can be utilized as a monoclonal antibody for therapeutic use to be administered into a human body, or for use in diagnostic imaging. Known techniques relevant to chimeric antibodies involve Japanese patent unexamined publication No. Hei 05-304989, Japanese patent unexamined publication No. Hei 04-330295, WO9106649, Japanese patent unexamined publication No. Sho 63-036786, Japanese patent examined publication No. Hei 06-98021, and the like.

Moreover, humanized antibodies were recently developed, which are appreciated as being more useful than chimeric antibodies. Humanized antibody refers to an antibody that is humanized as a whole molecule except for CDR of an antibody molecule by grafting only a sequence of a gene for an antigen-binding site (CDR: complementarity determining region) of an antibody molecule into a gene of a human antibody (CDR grafting). This antibody is appreciated as being safer with less antigenicity than the human-mouse chimeric antibody because it has less part derived from a mouse antibody. When SHM-D 33 strain (ATCC CRL 1668) or RF-S1 strain, both of which being human/mouse heteromyeloma, is used as a parent cell for producing a human monoclonal antibody, high fusion efficiency can be achieved that is equivalent to mouse parent cells. Hybridoma that was obtained using these parent cells can be cloned without feeder cells, and it can produce IgG type antibody in a comparatively stable manner at a large amount. For the culture of the parent cells, ERDF medium supplemented with 15% FCS may be used, although other operation may be similarly carried out to the operation for the murine cells. Additionally, in order to produce an IgG type human monoclonal antibody, human lymphocytes collected from peripheral blood may be preferably employed, which were sufficiently sensitized with an antigen. When it is difficult to obtain sufficiently sensitized lymphocytes, sensitization with an antigen may be also conducted in vitro. In Japan, clinical trials have been currently carried out for humanized antibodies to adult T cell leukemia. In respect to the production of human antibodies and the related art, for example, reference should be made to those disclosed in Genentech Inc., USA (WO9222653, WO9845332, WO9404679, WO9837200, WO9404679) and Celltech Inc., England (WO9429451, WO9429351, WO9413805, WO9306231, WO9201059, WO9116927, WO9116928, WO9109967, WO8901974, WO8901783), and the like.

Using the methods and the like described above, the antibodies according to the present invention can be humanized, and such antibodies would be extremely useful upon the administration to human.

Composition

The CL-L2s polynucleotides or proteins are possibly utilized in diagnostic, prophylactic and therapeutic methods, and for the development of reagents and drugs for various types of diseases including bacterial infections and the like.

Pharmaceutical composition according to the present invention may comprise CL-L2s polynucleotides or proteins, substances that stimulate or inhibit the activity or activation of CL-L2s protein, substances including antibodies to CL-L2s protein and the like (hereinafter, referred to as "CL-L2s related substance"). The CL-L2s related substances can be used neat, or after subjecting to several kinds of treatment such as dilution in water and the like, however, they can be used after blending in pharmaceutical products, quasi drugs and the like. In these cases, the amount of the substance to be blended may be determined ad libitum. When the substance is formulated for the systemic administration, 0.001-50% by weight, in particular, 0.01-10% by weight is permissible. When the amount is less than 0.001%, sufficient action of lacrimation may not be enabled. When the amount is greater than 50%, properties such as stability, flavor and the like of the composition itself may be deteriorated.

The route of administration can be optionally selected from the administration via mucosa, transdermal administration, intramuscular administration, subcutaneous administration, endorectal administration, topical ocular administration, and the like, in addition to oral administration and intravenous administration described above.

The CL-L2s related substance according to the present invention may be included in the formulation as a salt. Pharmaceutically acceptable salts include for example, salts with base such as inorganic base, organic base and the like; acid addition salts such as those of inorganic acid, organic acid, basic or acidic amino acid. Inorganic bases include for example, alkaline metal such as sodium, potassium and the like; alkaline earth metal such as calcium, magnesium and the like; aluminum, ammonium and the like. Organic bases include for example, primary amines such as ethanolamine and the like; secondary amines such as diethylamine, diethanolamine, dicyclohexylamine, N,N'-dibenzylethylenediamine and the like; tertiary amines such as trimethylamine, triethylamine, pyridine, picoline, triethanolamine and the like. Inorganic acids include for example, hydrochloric acid, hydrobromic acid, nitric acid, sulfuric acid, phosphoric acid and the like. Organic acids include for example, formic acid, acetic acid, lactic acid, trifluoroacetic acid, fumaric acid, oxalic acid, tartaric acid, maleic acid, benzoic acid, citric acid, succinic acid, malic acid, methanesulfonic acid, ethanesulfonic acid, benzenesulfonic acid, p-toluenesulfonic acid and the like. Basic amino acids include for example, arginine, lysine, ornithine and the like. Acidic amino acids include for example, aspartic acid, glutamic acid and the like.

Examples of dosage forms for use in oral administration include powdered formulations, granulated formulations, encapsulated formulations, pills, tablets, elixirs, suspensions, emulsions, syrups and the like, which may be selected ad libitum. In addition, such formulations may be modified, which may involve release control, stabilization, facilitation of disintegration, blocking of disintegration, enteric coating, facilitation of absorption and the like. Moreover, examples of dosage forms for the intraoral topical administration include chewable formulations, sublingual formulations, buccal formulations, lozenges, ointments, plasters, liquid formulations and the like, which may be selected ad libitum. Further, such formulations may be modified, which may involve release control, stabilization, facilitation of disintegration, blocking of disintegration, enteric coating, facilitation of absorption and the like.

Known drug delivery system (DDS) techniques may be applied to dosage forms as described above. DDS formulation referred to herein involves sustained release formulations, topically applied formulations (lozenges, buccal formulations, sublingual formulations), drug controlled release formulations, enteric coated formulations, formulations soluble in stomach and the like, which are formulations that are prepared so that most appropriate dosage form is accomplished taking into account of the administration route, bio-availability, adverse effect and the like.

Components for DDS essentially comprise a drug, a drug release module, a coating and a therapy program. In detail, the drug having a short half life is preferred, which permits rapid decline of the blood concentration particularly upon cessation of the release thereof. The coating is preferably nonreactive to the body tissue of the part to which the drug is administered. In addition, the therapy program is preferably configured so that the most optimal drug concentration is kept during the predetermined period. The drug release module substantially has a drug storage, a release control part, an energy source, and a release opening or a release surface. All of these fundamental components are not necessarily required, and thus addition, deletion or the like may be optionally carried out to select the best mode.

Examples of materials which can be used for DDS include polymers, cyclodextrin derivatives, lecithin and the like. The polymer may include insoluble polymers (silicone, ethylene-vinyl acetate copolymer, ethylene-vinyl alcohol copolymer, ethylcellulose, cellulose acetate and the like), water soluble polymers and hydroxyl gel-forming polymers (polyacrylamide, polyhydroxyethyl methacrylate cross-linked form, polyacryl cross-linked form, polyvinyl alcohol, polyethyleneoxide, water soluble cellulose derivatives, cross-linked poloxamer, chitin, chitosan and the like), slow dissolving polymers (ethyl cellulose, a partial ester of methylvinyl ether-maleic anhydride copolymer and the like), polymers soluble in stomach (hydroxylpropylmethyl cellulose, hydroxylpropyl cellulose, carmellose sodium, macrogol, polyvinylpyrrolidone, dimethylaminoethyl methacrylate-methyl methacrylate copolymer and the like), enteric polymers (hydroxylpropylmethyl cellulose phthalate, cellulose acetate phthalate, hydroxylpropylmethyl cellulose acetate succinate, carboxymethylethyl cellulose, acrylic acid polymers and the like), biodegradable polymers (heat coagulation or cross-linked albumin, cross-linked gelatin, collagen, fibrin, polycyanoacrylate, polyglycolic acid, polylactic acid, poly β-hydroxyacetic acid, polycaprolactone and the like), which can be selected ad libitum on the basis of the dosage form.

In particular, silicone, ethylene-vinyl acetate copolymer, ethylene-vinyl alcohol copolymer, a partial ester of methylvinyl ether-maleic anhydride copolymer can be used for the control of drug release; cellulose acetate can be used as a material of a osmotic pressure pump; ethyl cellulose, hydroxypropylmethyl cellulose, hydroxypropyl cellulose, methyl cellulose can be used as a material of a membrane of slow dissolving formulations; and polyacryl cross-linked form can be used as an attaching agent to mucosa.

Further, the formulation can be manufactured with adding solvent, excipient, coating agent, base, binding agent, lubricant, disintegrant, solubilizing agent, suspending agent, thickening agent, emulsifying agent, stabilizing agent, buffering agent, isotonizing agent, soothing agent, preservative agent, flavoring agent, fragrance agent, coloring agent and the like in compliance with its dosage form (known dosages form such as forms for oral administration, injection, suppository and the like).

Although specific examples are respectively illustrated below, these examples should not be construed as limiting the present invention.

[solvent] purified water, water for injection, saline, peanut oil, ethanol, glycerol;

[excipient] starches, lactose, glucose, sucrose, crystalline cellulose, calcium sulfate, calcium carbonate, talc, titanium oxide, trehalose, xylitol;

[coating agent] sucrose, gelatin, cellulose acetate phthalate and polymers as described above;

[base] vaseline, vegetable oil, macrogol, base for oil in water emulsion, base for water in oil emulsion;

[binding agent] natural polymer compounds such as starch and derivatives thereof, cellulose and derivatives thereof, gelatin, sodium alginate, gum tragacanth, gum arabic, and the like; synthetic polymers such as polyvinylpyrrolidone and the like; dextrin, hydroxylpropyl starch;

[lubricant] stearic acid and salts thereof, talc, waxes, wheat starch, macrogol, hydrogenated vegetable oil, sucrose fatty acid ester, polyethylene glycol;

[disintegrant] starch and derivatives thereof, agar, gelatin powder, sodium bicarbonate, cellulose and derivatives thereof, carmellose calcium, hydroxypropyl starch, carboxymethyl cellulose, and salts and derivatives thereof, poorly substituted hydroxypropyl cellulose; [solubilizing agent]cyclodextrin, ethanol, propylene glycol, polyethylene glycol;

[suspending agent] gum arabic, gum tragacanth, sodium alginate, aluminum monostearate, citric acid, various surfactants;

[thickening agent] carmellose sodium, polyvinylpyrrolidone, methyl cellulose, hydroxypropylmethyl cellulose, polyvinyl alcohol, gum tragacanth, gum arabic, sodium alginate;

[emulsifying agent] gum arabic, cholesterol, gum tragacanth, methyl cellulose, various surfactants, lecithin;

[stabilizing agent] sodium bisulfite, ascorbic acid, tocopherol, chelating agent, inert gas, reducing agent;

[buffering agent] sodium hydrogenphosphate, sodium acetate, boric acid;

[isotonizing agent] sodium chloride, glucose;

[soothing agent] procaine hydrochloride, lidocaine, benzyl alcohol;

[preservative agent] benzoic acid and salts thereof, p-hydroxybenzoic esters, chlorobutanol, inverted soap, benzyl alcohol, phenol, thimerosal;

[flavoring agent] sucrose, saccharin, glycyrrhiza extract, sorbitol, xylitol, glycerol;

[fragrance agent] orange peel tincture, rose oil;

[coloring agent] water soluble edible dye, lake dye.

EXAMPLES

Novel collectin according to the present invention is described in more detail by the following non-limiting illustrative examples. However, the present invention should not be construed to be limited by the examples.

Specifically, search on EST database (Example 1); screening of a novel human collectin from a cDNA library derived from human liver by PCR and sequencing of the base sequence (Example 2); screening of a novel human collectin a cap site cDNA library derived from human kidney by PCR and sequencing of the base sequence (Example 3); homology search of the novel collectin (Example 4); obtaining the novel mouse collectin cDNA (Example 5); analysis of distribution of expression of the novel human collectin in human tissues (Example 6); genetic analysis of the novel human collectin (Example 7); analysis of distribution of expression of the novel collectin CL-L2-1 and CL-L2-2 in human tissues (Example 8); construction of an expression vector pcDNA3.1/Myc-His(+)-CL-L2-1,2 of the novel collectin (Example 9); production of a cell strain that is stably expressing the novel collectin (Example 10); analysis of sugar specificity of the novel collectin (Example 11) are described below.

Example 1

Search on EST Database

Figure 1:
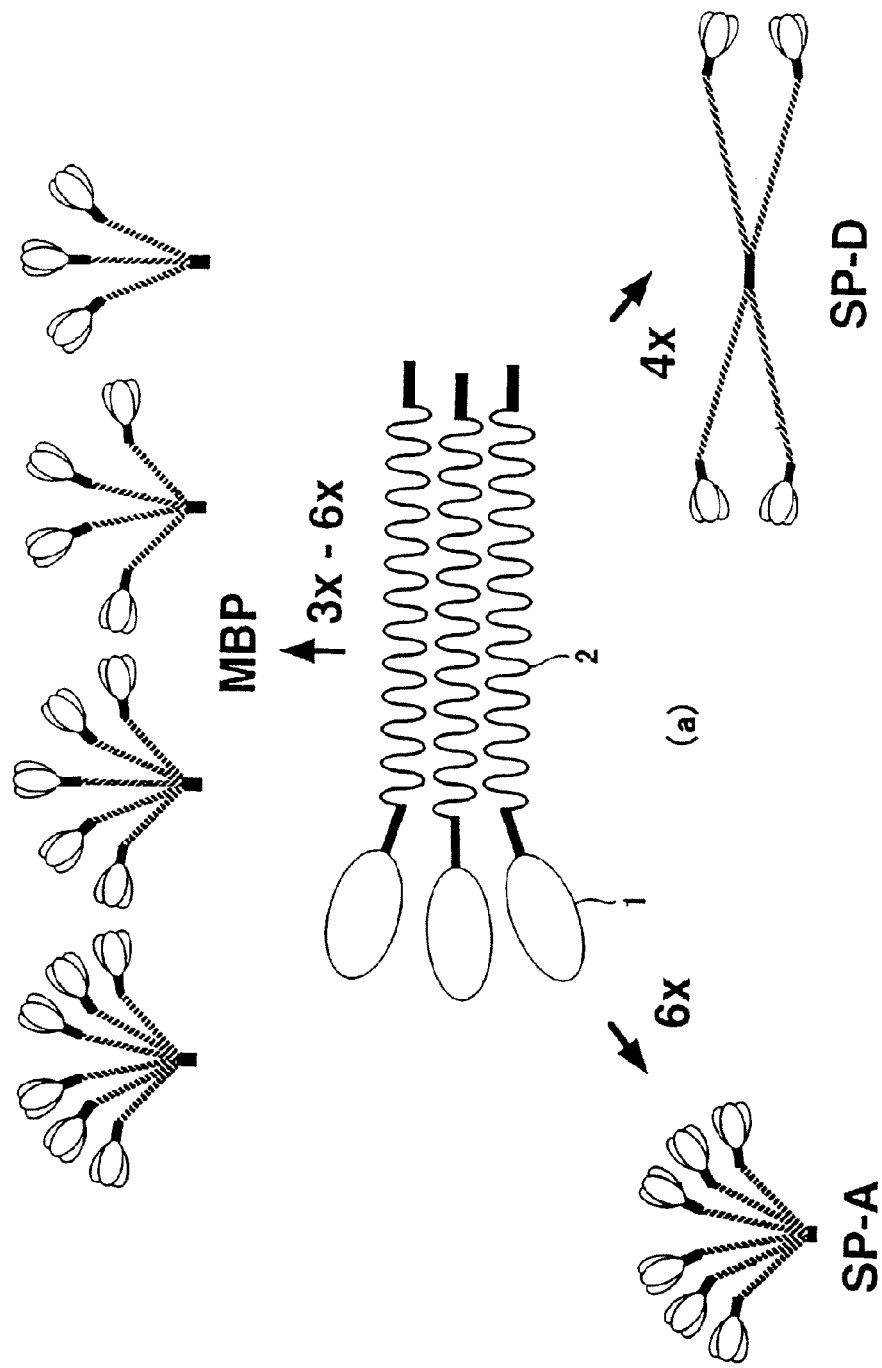
FIG. 1 is a schematic drawing illustrating a basic structure (a) of principal collectins reported heretofore and an overview of the protein (MBP, SP-A and SP-D).
Figure 2:
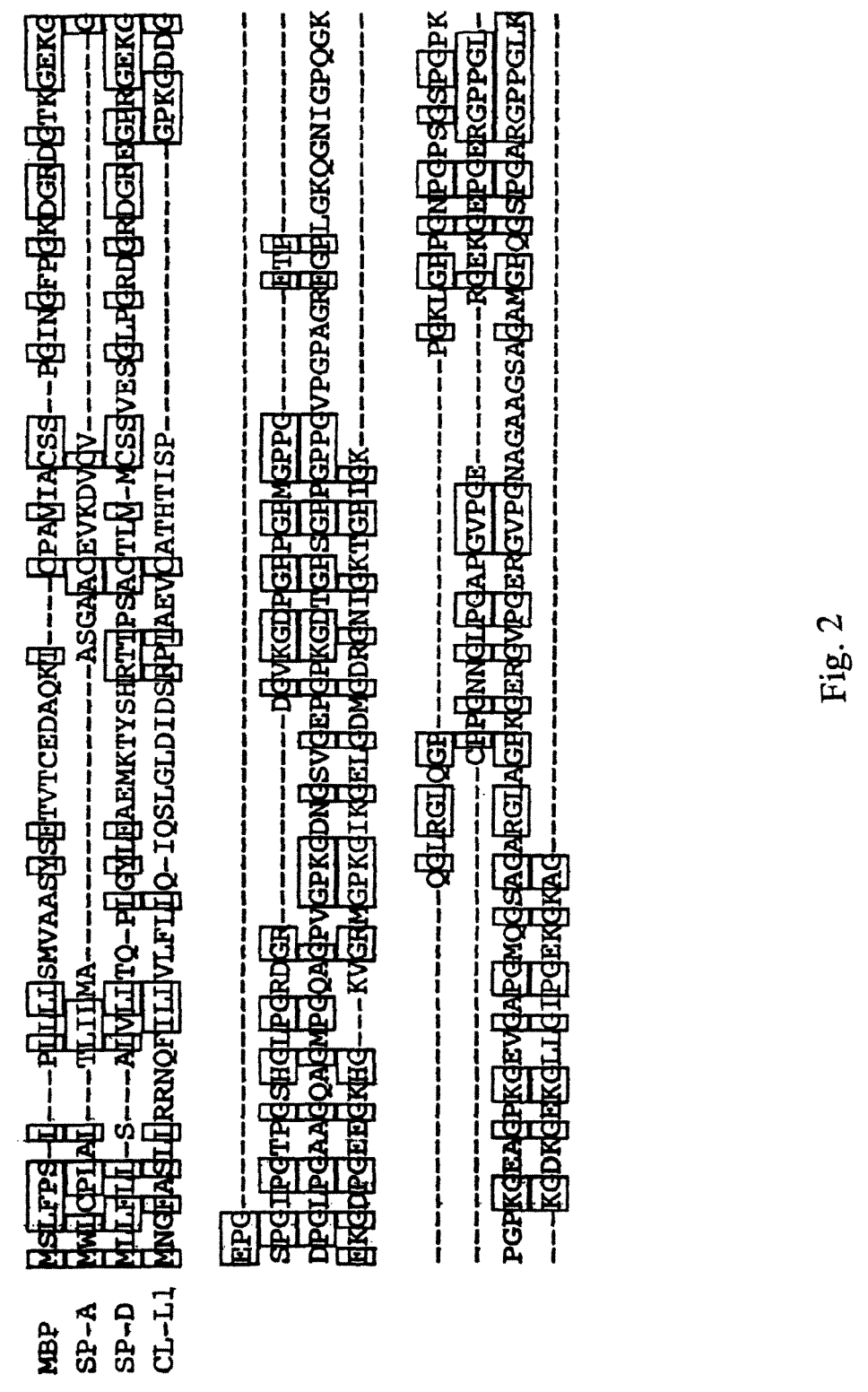
Figure 3:
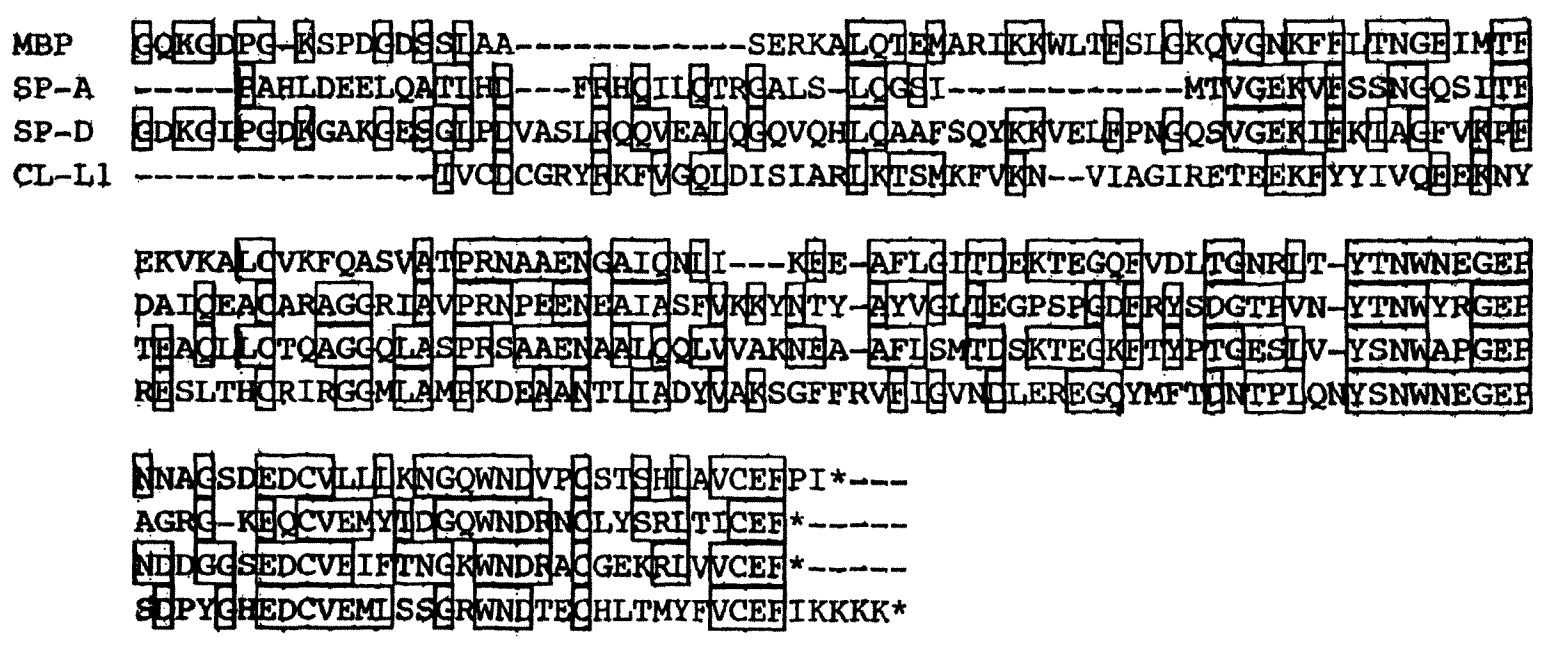

FIGS. 2 and 3 illustrate homology of amino acid residues of known collectins, i.e., human MBP, human SP-A, human SP-D and collectin CL-L1 derived from human liver, which was successfully isolated by the present inventor recently (see, Japanese patent unexamined publication No. Hei 11-206377), having a common structure as depicted in FIG. 1. In the Figure, portions of amino acid residues that are recognized as being homologous were boxed. An amino acid sequence of CRD (carbohydrate chain recognition domain) which is responsible for a lectin activity (SEQ ID NO: 14) of CL-L1 in this Figure was used to search on EST (Expressed Sequence Tags) database.

As a result, several data were obtained containing a highly homologous amino acid sequence. The amino acid sequences of thus resultant data were searched on GenBank/EST database, and determined whether they were either of known or unknown substance. Consequently, one datum (H30455, derived from thymus) that exhibits high homology but contains an unknown base sequence could be obtained. Using base sequence of the EST clone thus obtained, search of EST database was again conducted to give nine data (accession numbers: AA558494, derived from germ cells; AA582499, derived from kidney; AI420986, derived from prostate gland; AA742449, derived from germ cells; AA954657, derived from kidney; AA908360, derived from ovary; AI264145, derived from kidney; AA089855, derived from heart; AA456055, derived from melanocyte, pregnant uterus, fetal heart) that were found to include an identical base sequence. All of these were clones demonstrating a part of a base sequence of an identical novel collectin.

Example 2

Screening from a cDNA Library Derived from Human Liver by PCR and Sequencing of the Base Sequence A consensus sequence (SEQ ID NO: 15) was produced in view of base sequences of 10 clones described above. Then, two primers toward the upstream direction: CAP1 (5'-agattt-tattgtatagcttgg-3' (SEQ ID NO: 16)) and CAP2 (5'-ctggg-taataattacataatg-3' (SEQ ID NO: 17) on the basis of a consensus sequence obtained in Example 1, and primes pertinent to a part of a region of a vector of the cDNA library derived from human liver: λTriplEx-F1 (5'-aagctccgagatctggacgag-3' (SEQ ID NO: 18)) and λTriplEx-F2 (5'-ctcgggaagcgcgccat-tgtg-3' (SEQ ID NO: 19)) were synthesized with 392A DNA/RNA synthesizer manufactured by PE Applied Biosystems Inc., and the screening by PCR was conducted as described below in order to clone a 5' upstream region of a novel human collectin cDNA (see FIG. 4).

First PCR was conducted using a cDNA library derived from human (Clontech Co.) as a template of the screening by PCR. Reaction mixture contained LA PCR Buffer II ($Mg^{2+}$ free), 2.5 mM $MgCl_2$, each 1 μL of 200 μM dATP, dCTP, dGTP and dTTP (any of which is manufactured by Takara Shuzo Co., Ltd.), a cDNA library derived from human liver (Clontech Co.), 0.5 μM λTriplEx-F1 primer and 0.5 μM CAP1 primer in a total volume of 50 PCR was performed with a program of 35 cycles of heat denaturation at 95° C. for 20 seconds, annealing at 60° C. for 20 seconds, elongation reaction at 72° C. for 90 seconds; and in addition, heat denaturation at 95° C. for 5 min prior to the repeated reaction and final elongation reaction at 72° C. for 5 min. After completing the first PCR, second PCR was conducted. The product of the first PCR was used as a template at 1 μL, and primers employed were λTriplEx-F2 primer and CAP2 primer. The reaction was performed with a similar reaction constitution and program to the first PCR except that the cycle number was 25 cycles. The PCR hereinabove was performed with GeneAmp PCR System9700 manufactured by PE Applied Biosystems Inc. Thus resulting PCR product was verified on an agarose gel electrophoresis, and excised from the gel followed by freezing at −80° C. for 10 min. After centrifuging at 15000 rpm for 10 min, the product was purified by ethanol precipitation of the supernatant.

The purified DNA fragment was incorporated into pT7Blue Vector manufactured by Novagen CO., and the vector was transformed into competent cells, XL1-Blue cells. The transformant was cultured in a LB medium (100 μg/mL ampicillin) followed by extraction of the plasmid with an alkaline SDS method to sequence the base sequence thereof with BigDye Terminator Cycle Sequencing FS Ready Reaction kit and ABI PRISM 377 sequencer manufactured by Applied Biosystems Inc. Primers employed were M13 Universal Primer (5'-cgacgttgtaaaacgacggccagt-3' (SEQ ID NO: 20)) and M13 Reverse Primer (5'-caggaaacagctatgac-3' (SEQ ID NO: 21)), both of which were synthesized similarly to CAP1 primer. The base sequence accordingly obtained was revealed to be a base sequence having 575 bases longer than the CAP2 primer starting from 3'-end to N-terminal end thereof (a region corresponding to: the amino acid position of 68-271 of CL-L2-10RF shown in FIG. 4; or the amino acid position of 42-245 of CL-L2-2 ORF). However, slight difference was found from the base sequence of 5'-end region of the consensus sequence of EST obtained in Example 1.

Example 3

Screening of a Novel Human Collectin from a Cap Site cDNA Library Derived from Human Kidney by PCR and Sequencing of the Base Sequence In order to clone 5'-end region containing a transcription initiation site in addition to the base sequence obtained in Example 2, screening by PCR was conducted using a cap site cDNA as follows through synthesizing two primers toward the upstream direction: CAP3 (5'-ggtcctatgtcaccggaatc-3' (SEQ ID NO: 22)), CAP4 (5'-ttccatgacgacccacactgc-3' (SEQ ID NO: 23)) with 392A DNA/RNA synthesizer manufactured by PE Applied Biosystems Inc., on the basis of the base sequence obtained in Example 2 (FIG. 4).

First PCR was performed with Cap Site cDNA, Human Kidney manufactured by NIPPON GENE Co., Ltd. using attached 1RC2 primer (5'-caaggtacgccacagcgtatg-3' (SEQ ID NO: 24)) and CAP3 primer. Reaction mixture contained LA PCR Buffer II ($Mg^{2+}$ free), 2.5 mM $MgCl_2$, each 1 μL of 200 μM dATP, dCTP, dGTP and dTTP (any of which is manufactured by Takara Shuzo Co., Ltd.), a Cap Site cDNA Human kidney, 0.5 µM 1RC2 primer (both of which were manufactured by NIPPON GENE Co., Ltd.), and 0.5 µM CAP3 primer in a total volume of 50 PCR was performed with a program of 35 cycles of heat denaturation at 95° C. for 20 seconds, annealing at 60° C. for 20 seconds, elongation reaction at 72° C. for 60 seconds; and in addition, heat denaturation at 95° C. for 5 min prior to the repeated reaction and final elongation reaction at 72° C. for 10 min. After completing the first PCR, second PCR was conducted. The product of the first PCR was used as a template at 1 µL, and primers employed were attached 2RC2 primer (5'-gtacgccacagcgtatgatgc-3' (SEQ ID NO: 25)) and CAP4 primer. The reaction was performed with a similar reaction constitution and program to the first PCR except that the cycle number was 25 cycles. The PCR hereinabove was performed with GeneAmp PCR System9700 manufactured by PE Applied Biosystems Inc. Thus resulting PCR product was verified on an agarose gel electrophoresis, and excised from the gel followed by freezing at −80° C. for 10 min. After centrifuging at 15000 rpm for 10 min, the product was purified by ethanol precipitation of the supernatant.

The purified DNA fragment was incorporated into pT7Blue Vector manufactured by Novagen CO., and the vector was transformed into competent cells, XL1-Blue cells. The transformant was cultured in a LB medium (100 µg/mL ampicillin) followed by extraction of the plasmid with an alkaline SDS method to sequence the base sequence thereof with BigDye Terminator Cycle Sequencing FS Ready Reaction kit and ABI PRISM 377 sequencer manufactured by Applied Biosystems Inc. Primers employed were M13 Universal Primer (5'-cgacgttgtaaaacgacggccagt-3' (SEQ ID NO: 20)) and M13 Reverse Primer (5'-caggaaacagctatgac-3' (SEQ ID NO: 21)). Two base sequences accordingly obtained were revealed to be: a base sequence having 492 bases longer than the base sequence obtained in Example 2 to its N-terminal direction (SEQ ID NO: 1); and a base sequence having 274 bases longer than the base sequence obtained in Example 2 to its N-terminal direction (SEQ ID NO: 3).

Consequently, two cDNAs in connection with CL-L2 were obtained hereby including: cDNA having an ORF (open reading frame) of 813 bases (SEQ ID NO: 1) and encoding 271 amino acids set out in SEQ ID NO: 2 (CL-L2-1); and cDNA having an ORF (open reading frame) of 735 bases (SEQ ID NO: 3) and encoding 245 amino acids set out in SEQ ID NO: 4 (CL-L2-2).

Example 4

Homology Search

Next, homology search was conducted for DNA and amino acid on GenBank database. As a result, the obtained amino acid sequence was demonstrated to be a that of a novel protein, which is distinct from any of collectins that have been found so far.

Figure 5:
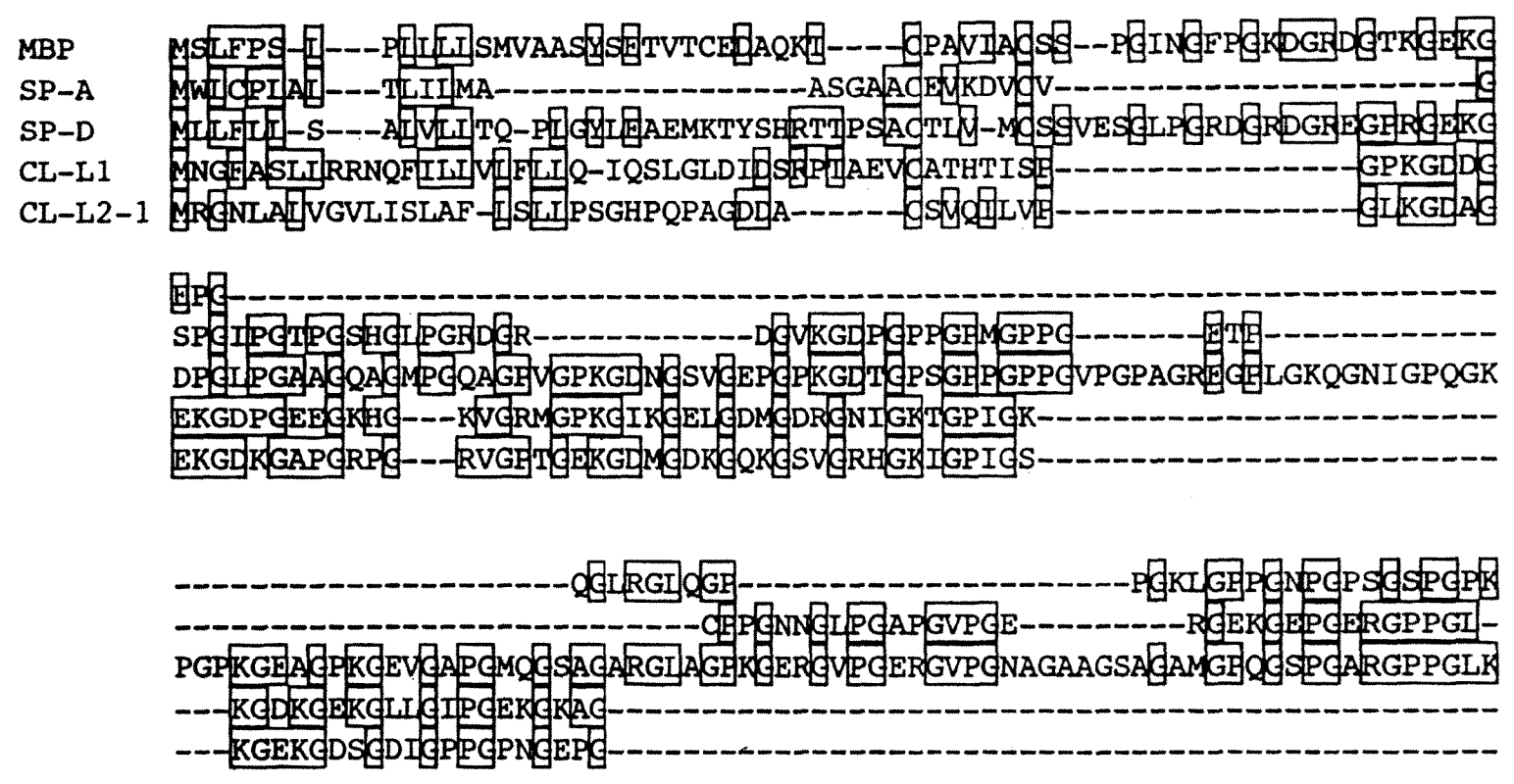

Amino acid sequences of three kinds of collectins reported so far (MBP, SP-A and SP-D) and collectin CL-L1 derived from human liver, which was successfully isolated by the present inventor recently (see, Japanese patent unexamined publication No. Hei 11-206377) were compared with the amino acid sequence of the collectin structural part of the novel collectin according to the present invention. The results are illustrated in FIG. 5 and FIG. 6. Similarly to FIGS. 2 and 3, portions of amino acid residues that are recognized as being homologous were boxed. According to this alignment, it was demonstrated that the resultant novel protein has homology to known collectin proteins, and that it belongs to a collectin family.

In addition, a mutant (SEQ ID NO: 6) encoded by the position of 141-731 of the base sequence set out in SEQ ID NO: 5 having deletion of amino acids of 18-65 in the amino acid sequence set out in SEQ ID NO: 4; a mutant (SEQ ID NO: 8) encoded by the position of 141-803 of the base sequence set out in SEQ ID NO: 7 having deletion of amino acids of 18-41 in the amino acid sequence set out in SEQ ID NO: 4; and a mutant (SEQ ID NO: 10) encoded by the position of 141-803 of the base sequence set out in SEQ ID NO: 9 having deletion of amino acids of 42-65 in the amino acid sequence set out in SEQ ID NO: 4 were obtained.

Example 5

Obtaining cDNA of Mouse Novel Mouse Collectin

In a similar manner to that for hCL-L2, mCL-L2 gene could be obtained through the screening of a mouse liver cDNA library. The resulting cDNA clone of mCL-L2 was confirmed to have an ORF (open reading frame) of 813 bases (SEQ ID NO: 12), and encode amino acids of 271 amino acids set out in SEQ ID NO: 13.

Example 6

Analysis of Distribution of Expression of the Novel Collectin in Human Tissues

In order to examine the expression of the novel collectin in various tissues, analysis was performed by RT-PCR. RT-PCR was performed using two primers which are capable of amplifying a cDNA sequence spanning from neck region to carbohydrate recognition domain of the novel collectin: RTF1 (5'-agattccggtgacataggacc-3' (SEQ ID NO: 26)), RTR1 (5'-tggtctgggctctgtccctgc-3' (SEQ ID NO: 27)), and two primers which are capable of amplifying a part of β-actin gene for use in comparison of the amount of expressed novel collectin in each of the tissues: human β-actin sense primer (5'-caagagatggccacggctgct-3' (SEQ ID NO: 28)), human β-actin antisense primer (5"-tccttctgcatcctgtcggca-3' (SEQ ID NO: 29)). All of these primers were synthesized in a similar manner to CAP1 primer to conduct RT-PCR.

RT-PCR was carried out using RNA LA PCR Kit (AMV) Ver.1.1 (TAKARA Syuzo, Co.) with each RNA derived from several human tissues ((1) brain, (2) heart, (3) kidney, (4) liver, (5) lung, (6) trachea, (7) bone marrow, (8) colon, (9) small intestine, (10) spleen, (11) stomach, (12) thymus, (13) mammary gland, (14) prostate gland, (15) skeletal muscle, (16) testis, (17) uterus, (18) cerebellum, (19) fetal brain, (20) fetal liver, (21) spinal cord, (22) placenta, (23) adrenal gland, (24) pancreas, (25) salivary gland, and (26) thyroid) as a template. First, a reverse transcription reaction was conducted in the following reaction mixture.

Figure 7:
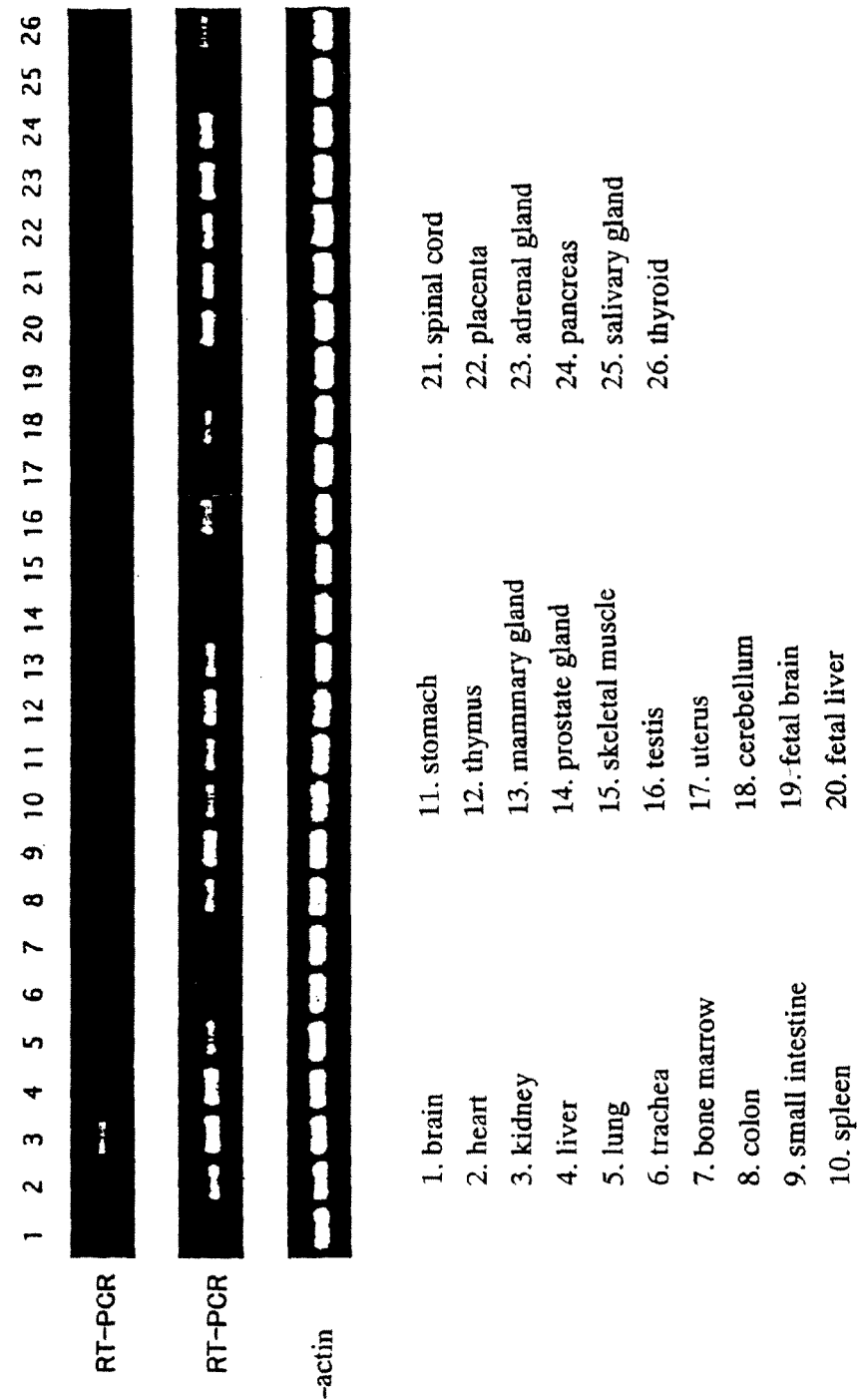
FIG. 7 shows results of analysis of distribution of mRNA in various human tissues demonstrating the tissue distribution of the novel collectin hCL-L2 of the present invention.

The reaction mixture contained 5 mM $MgCl_2$, 1×RNA PCR Buffer, 1 mM dNTP Mixture, 1 U/µl RNase inhibitor and 2 µg of RNA, and total volume of the mixture was adjusted to give 40 µl with RNase free distilled water. At the same time, a reaction mixture without reverse transcriptase was also prepared for a negative control. The reaction mixture as described above was placed in 0.2 ml tube, and subjected to a reverse transcription reaction with GeneAmp PCR System9700 manufactured by PE Applied Biosystems Inc. through 1 cycle of: 30 minutes at 42° C., 5 minutes at 99° C., and 5 minutes at 5° C. Thus resulting reverse transcription reaction product was subsequently used at 10 µL for LA PCR in the following reaction mixture with respectively 28 cycles and 35 cycles. Thereto were added 2.5 mM $MgCl_2$, 1×LA PCR Buffer ($Mg^{2+}$ free), 2U TaKaRa LA Taq, 0.2 µM RTF1 primer and 0.2 µM RTR1 primer, and the mixture was adjusted to give total volume of 50 µL with sterilized distilled water. PCR was performed with a program of 28 or 35 cycles of heat denaturation at 95° C. for 20 seconds, annealing at 60° C. for 20 seconds, elongation reaction at 72° C. for 60 seconds; and in addition, heat denaturation at 95° C. for 5 min prior to the repeated reaction and final elongation reaction at 72° C. for 10 min. The reaction product was separated on 1.5% agarose gel electrophoresis, followed by staining with ethidium bromide solution (0.1 µg/mL), verification of the electrophoretic pattern with transilluminator, and identification of the expressing tissue. In order to compare the expressed amount in each of the tissues, RT-PCR was performed to amplify a part of β-actin with each of the tissues, and the correction of the amount of RNA was conducted. The RT-PCR was performed similarly to the above procedure with reverse transcription reaction, PCR, and the estimation was executed. The results are illustrated in FIG. 7, which demonstrate the expression of the novel collectin according to the present invention for PCR performed with 28 cycles in kidney (lane 3) intensively, and also in liver (lane 4), small intestine (lane 9), thymus (lane 12), fetal liver (lane 20), spinal cord (lane 21), adrenal gland (lane 23) and pancreas (lane 24). Further, with respect to PCR performed with 35 cycles, ubiquitous expression of the novel collectin could be verified in all tissues tested, although varying intensity of expression was observed.

Example 7

Genetic Analysis of the Novel Collectin

On the basis of sequence of DNAs of the obtained novel collectin (hCL-L2-1 (SEQ ID NO: 1) and mCL-L2 (SEQ ID NO: 12)), a phylogenetic tree was produced through conducting the analysis for the purpose of clarifying genetic position among the known collectins.

Figure 8:
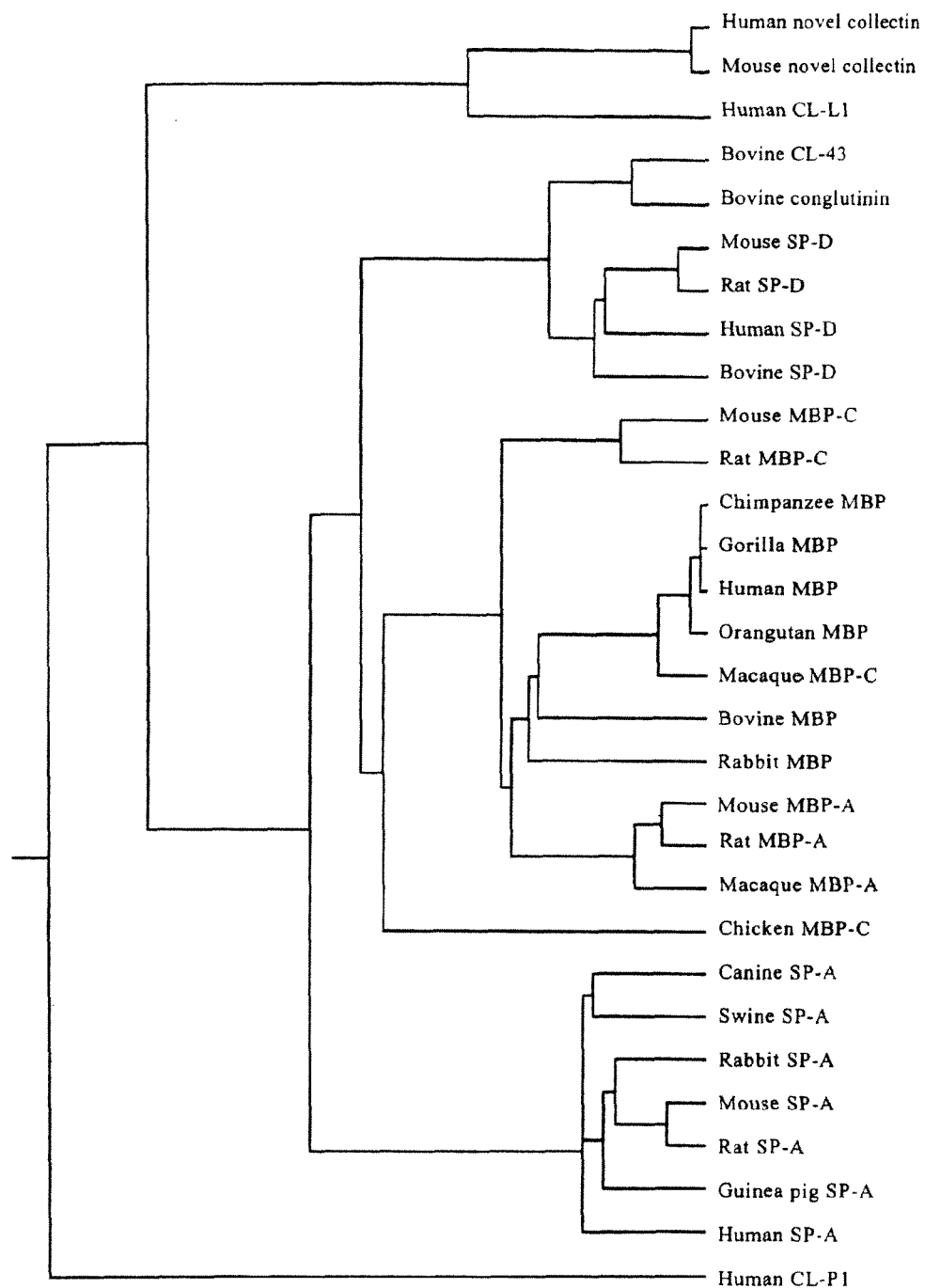
FIG. 8 shows a phylogenetic tree of various collectins.

Collectins targeted for the analysis were proteins in various collection families illustrated in FIG. 8 (in the Figure, CL-L1 and CL-P1 were successfully isolated by the present inventors). Multiple alignment was produced with clustalw method using a region containing a lectin domain on the basis of data which were obtained by searching each amino acid sequences from GenBank database. A phylogenetic tree was produced with Phylip version 3.57c package program using N-J process (neighbor-joining process) based on thus resulting multiple alignment.

Consequently, it was assumed that SP-D, bovine CL-43, and bovine conglutinin formed one cluster, whilst MBP and SP-A respectively form separate clusters, however, the novel collectin of the present invention did not belong in any of these clusters but belonged in the same cluster with CL-L1. Accordingly, it was speculated that the novel collectin of the present invention is a homologue of CL-L1.

Example 8

Analysis of Distribution of Expression of Novel Collectin (CL-L2-1 and CL-L2-2) in Human Tissues Analysis with RT-PCR technique was conducted in order to examine expression of CL-L2-1 (SEQ ID NO: 1) and CL-L2-2 (SEQ ID NO: 3) in various tissues. RT PCR was conducted using primers which are capable of amplifying the entire translated region of CL-L2-1 as obtained (RTF2 (5'-atgagggggaatctggccctggtg-3' (SEQ ID NO: 30)), RTR2 (5'-catgttctccttgtcaaactcac-3' (SEQ ID NO: 31))); primers which are capable of amplifying the entire translated region of CL-L2-2 as obtained (RTF3 (5'-atgtggtgggtgcctccgagtc-3' (SEQ ID NO: 32)), RTR2 (SEQ ID NO: 31)); and two human β-actin primers used in Example 6, which are capable of amplifying a part of β-actin gene for use in comparison of the amount of expressed novel collectin in each of the tissues. All of these primers were synthesized in a similar manner to CAP1 primer, and RT-PCR was performed similarly to Example 6.

Figure 9:
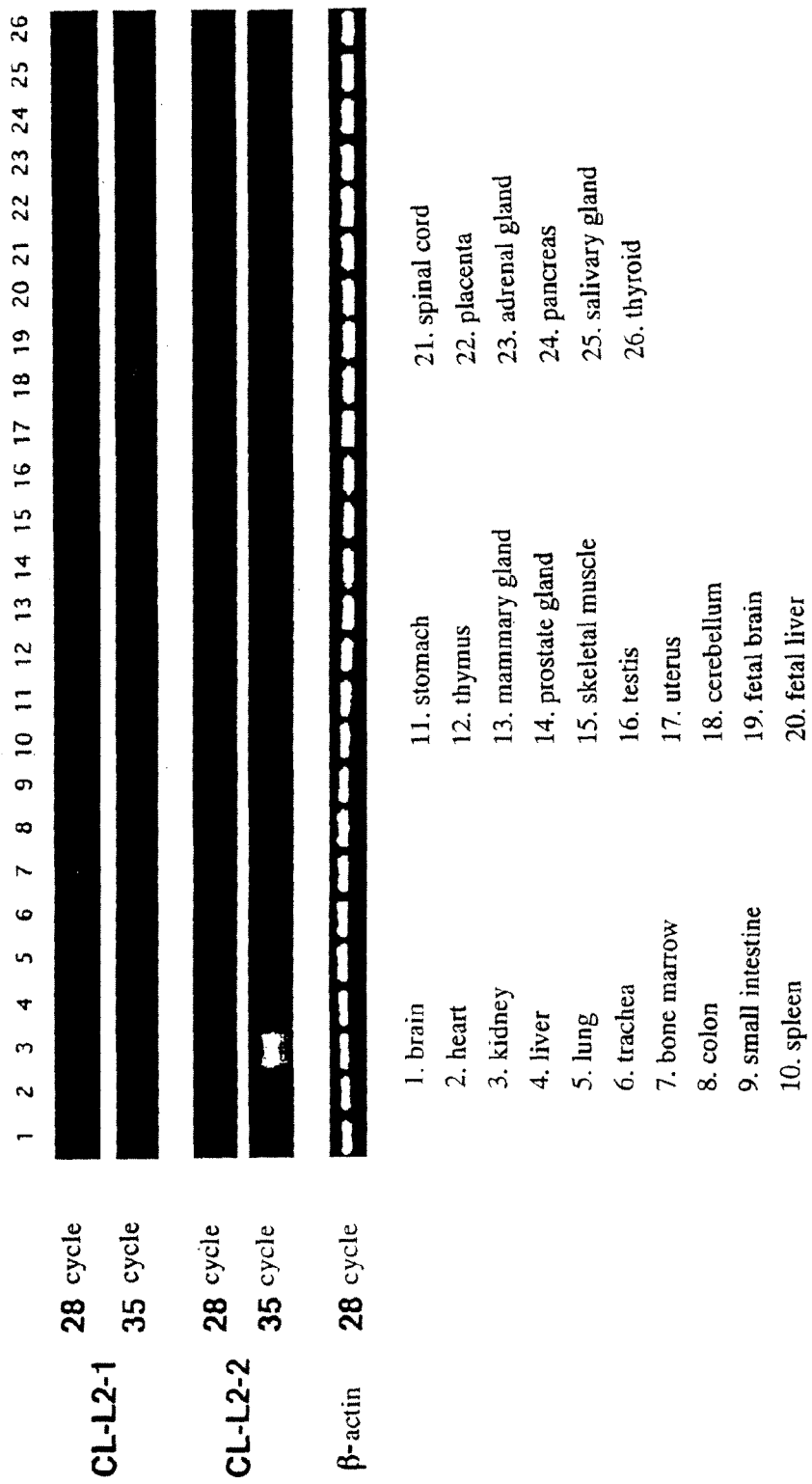
FIG. 9 shows results of analysis of distribution of mRNA in various human tissues demonstrating the tissue distribution of the novel collectin hCL-L2-1 and hCL-L2-2 of the present invention.

The results are illustrated in FIG. 9, which demonstrate intensive expression of CL-L2-1 (SEQ ID NO: 1) according to the present invention for PCR performed with 28 cycles in kidney (lane 3), liver (lane 4), small intestine (lane 9), thymus (lane 12), fetal liver (lane 20), spinal cord (lane 21), adrenal gland (lane 23), pancreas (lane 24). Further, with respect to PCR performed with 35 cycles, ubiquitous expression of CL-L2-1 (SEQ ID NO: 1) could be verified in all tissues tested, although varying intensity of expression was observed. Moreover, it was found that CL-L2-2 (SEQ ID NO: 3) was intensively expressed in kidney (lane 3) for PCR performed with 28 cycles, whilst for PCR performed with 35 cycles was expressed in kidney (lane 3) as well as in prostate gland (lane 14), testis (lane 16), spinal cord (lane 21), placenta (lane 22).

Additionally, several amplified fragments were found in RT-PCR products of CL-L2-1 and CL-L2-2 as shown in FIG. 9. These bands were excised from the gel, and purified by a similar process to that in Example 2, i.e., by freezing at −80° C. for 10 min, centrifuging at 15000 rpm for 10 min followed by ethanol precipitation of the supernatant. Purified DNA fragment was incorporated into pT7Blue Vector manufactured by Novagen Co., and thus resulting vector was transformed into competent cells, XL1-Blue cells. The transformant was cultured in a LB medium (100 ampicillin), and then a plasmid was extracted by an alkali SDS method. Base sequence was determined with BigDye Terminator Cycle Sequencing FS Ready Reaction kit and ABI PRISM 377 sequencer manufactured by PE Applied Biosystems Inc. Primers employed were M13 Universal Primer (5'-cgacgttg-taaaacgacggccagt-3'(SEQ ID NO: 20)) and M13 Reverse Primer (5'-caggaaacagctatgac-3' (SEQ ID NO: 21)).

Thus resulting base sequence was the same as CL-L2-2v1, CL-L2-2v2 and CL-L2-2v3 which are variants of CL-L2-2 (SEQ ID NO: 3) obtained in Example 2. Further, three proteins were present as CL-L2-1 set out in SEQ ID NO: 2, which were derived from alternative splicing of mRNA. Those are referred to as CL-L2-1v1 (SEQ ID NO: 36, 37), CL-L2-1v2 (SEQ ID NO: 38, 39) and CL-L2-1v3 (SEQ ID NO: 40, 41). CL-L2-1v1 has deletion of the amino acid position of 44-91 of CL-L2-1 set out in SEQ ID NO: 2 (deletion of the base position of 394-537 of CL-L2-1 set out in SEQ ID NO:1), whose amino acid sequence is encoded by the position of 265-933 of a base sequence set out in SEQ ID NO: 36 (SEQ ID NO: 59). CL-L2-1v2 has deletion of the amino acid position of 44-67 of CL-L2-1 set out in SEQ ID NO: 2 (deletion of the base position of 394-465 of CL-L2-1 set out in SEQ ID NO:1), whose amino acid sequence is encoded by the position of 265-1005 of a base sequence set out in SEQ ID NO: 38 (SEQ ID NO: 60). CL-L2-1v3 has deletion of the amino acid position of 68-91 of CL-L2-1 set out in SEQ ID NO: 2 (deletion of the base position of 466-537 of CL-L2-1 set out in SEQ ID NO:1), whose amino acid sequence is encoded by the position of 265-1005 of a base sequence set out in SEQ ID NO: 40 (SEQ ID NO: 61). Moreover, mCL-L2-2 gene can be obtained in a similar process to that in Example 4.

Example 9

Construction of Expression Vector pcDNA3.1/Myc-His(+)A-CL-L2-1,2 of Novel Collectin A translated region of CL-L2-1 (SEQ ID NO: 1) was amplified using CL-L2-1F primer (5'-gggaagcttcgatcaggat-gaggggaatctggccctggtg-3' (SEQ ID NO: 33)) and CL-L2-1R primer (5'-gggctcgagcatgttctccttgtcaaactcac-3' (SEQ ID NO: 34)) by PCR (Takara Thermal Cycler MP manufactured by Takara Shuzo Co., Ltd.) with a cDNA library derived from human kidney as a template. Further, a translated region of the novel collectin (SEQ ID NO: 3) was amplified using CL-L2-2F primer (5'-gggaagcttccagcacaatgtggtgggtgcctccgagtc-3' (SEQ ID NO: 35)) and CL-L2-1R primer (SEQ ID NO: 34)) by PCR with a cDNA library derived from human kidney as a template. Thus resulting CL-L2-1 cDNA was ligated to pT7Blue T-Vector (manufactured by Novagen Co.) and was transformed into *Escherichia coli* XLI-Blue. A plasmid containing CL-L2-1 cDNA was purified from the resulting clone. Following the confirmation of the base sequence of the resulting plasmid with a sequencer, the plasmid with no error was digested with restriction enzymes Hind III and Xho I, and ligated to pcDNA3.1/Myc-His(+)A vector (manufactured by Invitrogen Co.) that had been digested with the same enzymes and purified. After the ligated plasmid was transformed into *Escherichia coli*, XLI-Blue, the resulting clone was cultured. The plasmid was then purified to give an expression vector pcDNA3.1/Myc-His(+)A-CL-L2-1,2. At the same instant, expression vectors were similarly produced for variants of CL-L2-1 and CL-L2-2 (SEQ ID NO:5, SEQ ID NO: 7, SEQ ID NO: 9, SEQ ID NO: 36, SEQ ID NO: 38 and SEQ ID NO: 40).

Example 10

Production of Cell Strain which is Stably Expressing Novel Collectin

Transient expression was conducted through cotransfection of the expression vector pcDNA3.1/Myc-His(+)A-CL-L2-1 obtained in Example 9 and pEGFP-F vector (manufactured by Clontech Co.) to CHO cells using LIPOFECTAMINE 2000 (LF2000) Reagent (manufactured by GIBCO BRL Co.). A 0.5 ml solution of LF2000 Reagent (LF2000 Reagent 30 Nutrient Mixture F-12 Ham (Ham's F-12 medium, (manufactured by Sigma Co.))) was first prepared, and incubated at room temperature for 5 minutes. Then, 0.5 ml of a vector solution (pcDNA3.1/Myc-His(+)A-CL-L2-1,2: 7.5 pEGFP-F vector 2.5 µg, Ham's F-12 medium) was admixed therewith, followed by incubation for 20 minutes. Thereafter, the solution was added to CHO cells that had been cultured to a high density in a 25 $cm^2$ flask including 5 ml of Ham's F-12 medium containing 5% FCS. After incubating at 37° C. for 4 hours in the presence of 5% $CO_2$, the medium was replaced with a flesh medium, followed by subsequent incubation at 37° C. for 20 hours in the presence of 5% $CO_2$. Next, the medium was replaced with Ham's F-12 medium containing 5% FCS, 0.4 mg/ml Geneticin, (manufactured by GIBCO BRL Co.), and 10 days culture was subsequently conducted. In this process, replacement of the medium was once carried out.

Through this selection by a drug for 10 days, only the transformed cells could survive and proliferated, however to the contrary, cells that were not transformed were dead. In order to obtain highly expressing cells from the resulting transformed cells, sorting was performed by a cell sorter (manufactured by Becton Dickinson Co.) with fluorescence of GFP as a marker. After washing the transformed cells in the 25 $cm^2$ flask with 5 ml PBS(−) twice, the cells were stripped off with 0.3 ml of 0.02% EDTA solution (manufactured by Nakarai Tesc KK). The cells were suspended in 10 ml PBS (−), and thereafter centrifuged at 200×g for 7 minutes at 4° C. to remove the supernatant. The remaining cells were suspended in 0.5 ml of 2% FCS/PBS (−) to give a sorting sample. After the sample was passed through a 5 ml tube equipped with a cell strainer cap (manufactured by Becton Dickinson Co.), it was applied to a cell sorter. CHO cells without subjecting to the transformation, which had been similarly treated, were used as control cells. Accordingly, a sample was selected, which exhibited fluorescence intensity of 10 times or greater than the control sample. These cells were dispensed into 96-well cell culture plates, of which wells respectively contained 100 µl Ham's F-12 medium (containing 5% FCS, 0.4 mg/ml Geneticin), to charge a single cell per well. After the cells were cultured at 37° C. in the presence of 5% $CO_2$ for one week, each 100 µl of a culture medium was further added thereto followed by the additional culture for one week. A clone proliferated by the drug selection with Geneticin was divided into two parts, which were subjected to passages on 12-well and 24-well cell culture plates. Upon the passage, clones were excluded, which were derived from proliferation in a well where two or more cells existed per well, and the cells were plated at a cell number ratio of 9:1 for the 12-well and 24-well cell culture plates. The cells were cultured at 37° C. in the presence of 5% $CO_2$ until the cells in the 12-well plate reach to high density. Then, 200 µA of the culture supernatant was dot blotted on an Immobilon-P membrane (manufactured by Millipore Co., Ltd.) using Bio-Dot Microfiltration Apparatus (manufactured by BIO-RAD Co., Ltd.), and the membrane was incubated in a solution of anti-myc antibody (manufactured by Invitrogen Co.)×5000 diluted in 0.05% Tween 20/TBS buffer (manufactured by Takara Shuzo Co., Ltd.) at room temperature for 1 hour. Thereafter, the membrane was washed with 100 ml of 0.05% Tween 20/TBS buffer at room temperature for 20 min.×3 followed by further incubation in a solution of anti-IgG-HRP (manufactured by Chemicon Co., Ltd.)×5000 diluted in 0.05% Tween 20/TBS buffer at room temperature for 1 hour. Thereafter, the membrane was washed with 100 ml of 0.05% Tween 20/TBS buffer at room temperature for 20 minutes×3 followed by detection using TMB Membrane Peroxidase substrate system (manufactured by Funakoshi KK). After confirming the clones with intense color development, cells in respectively corresponding wells of the 24-well plate were identified as a stably expressing cell strain (CHO/CL-L2-1).

Example 11

Analysis of Sugar Binding Specificity of Novel Collectin

One litter of the culture supernatant of the stably expressing cell strain of the novel collectin (CHO/CL-L2-1) produced in Example 10 was concentrated to 50 ml using VIVAPORE10 (manufactured by Funakoshi KK), thereafter was added 200 µl of Ni-NTA agarose (manufactured by Quiagen Co., Ltd.) thereto. The novel collectin was bound to Ni-NTA agarose by incubation of the mixture with shaking at 4° C. overnight. Ni-NTA agarose was packed in Poly-Prep Chromatography Columns (manufactured by BIO-RAD Co., Ltd.) followed by washes with 5 ml of 50 mM NaH$_2$PO$_4$, 300 mM NaCl, 20 mM imidazole, 0.05% Tween20 (pH8.0) three times, and by elution with 200 µl of 50 mM NaH$_2$PO$_4$, 300 mM NaCl, 250 mM imidazole, 0.05% Tween20 (pH8.0) five times to purify the novel collectin. Purified novel collectin was quantitatively determined, and used for the analysis of sugar specificity.

Figure 10:
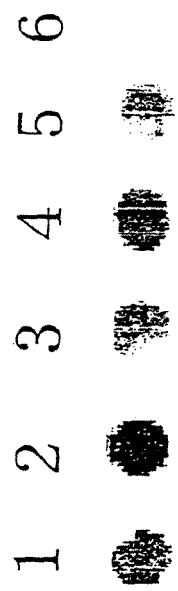
FIG. 10 is a schematic drawing illustrating a sugar binding characteristics of the novel collectin hCL-L2-1 of the present invention.

Specifically, 1 µg of the purified novel collectin was dot blotted on an Immobilon-P membrane (manufactured by Millipore Co., Ltd.) to give spots in a number corresponding to types of sugar chain probes to be examined for binding specificity, using Bio-Dot Microfiltration Apparatus (manufactured by BIO-RAD Co., Ltd.). Each dot was thereafter cut to yield 1 cm square, and was immersed in Block Ace (manufactured by Dai Nippon Pharmaceutical Co., Ltd.), and was incubated at room temperature for 1 hour. Next, the membrane was washed with 0.05% Tween20, 5 mM CaCl$_2$, TBS buffer three times, and was incubated in each sugar chain probe solution (see, FIG. 10) diluted with 5 mM CaCl$_2$, TBS buffer to give 1 µg/ml at room temperature for 1 hour. Thereafter, the membrane was again washed with 0.05% Tween20, 5 mM CaCl$_2$, TBS buffer three times. Then the membrane was incubated in a solution of Streptabvidin-biotinylated HRP (manufactured by Amersham Co.)×1000 diluted in 0.05% Tween20, 5 mM CaCl$_2$, TBS buffer at room temperature for 30 min. followed by washes with 0.05% Tween20, 5 mM CaCl$_2$, TBS buffer three times and by detection using TMB Membrane Peroxidase substrate system (manufactured by Funakoshi KK). As is shown in FIG. 10, the novel collectin was active in binding to mannose, fucose, N-acetylgalactosamine, N-acetylneuraminic acid, mannose-6-phosphoric acid.

Because CL-L2s protein of the present invention has a collectin structure, it is believed to be a substance that exerts characteristic effects to those structures. Therefore, it can be utilized in the elucidation of mechanisms of fundamental immunity; in the elucidation of mechanisms of the development of a wide variety of diseases such as bacterial infections; in the diagnostic, prophylactic and therapeutic methods thereof; and in the development of reagents and drugs for the same.

What is claimed is:

1. An isolated protein consisting of the amino acid sequence set forth in SEQ ID NO: 13.

2. The protein according to claim 1, which is produced by a method comprising the steps of culturing in a culture medium cells transformed with a vector comprising the base sequence set out in SEQ ID NO: 58 and harvesting the protein secreted from the cells in the culture medium.

3. The protein according to claim 2, wherein said cell is *Escherichia coli*.

4. The protein according to claim 2, wherein said cell is an animal cell.

5. The protein according to claim 2, wherein said cell is an insect cell.

* * * * *

```
                         SEQUENCE LISTING

<160> NUMBER OF SEQ ID NOS: 61

<210> SEQ ID NO 1
<211> LENGTH: 1341
<212> TYPE: DNA
<213> ORGANISM: Homo Sapiens
<220> FEATURE:
<221> NAME/KEY: CDS
<222> LOCATION: (265)..(1077)

<400> SEQUENCE: 1
cgcggccgcg tcgacggacg gtggacgcag cgcagacagg aagctccccg agataacgct      60
gcggccgggc ggcctgattt gctgggctgt ctgatggccc gggccgaggc ttctccctgc     120
gcctgggact gcggccgcct ctctaaatag cagccatgag gcgcctgggg gcagtgtcct     180
cgcggccgcg tcgaccgacg gccgcagtcg acgccccgtt cgcctagcgc gtgctcagga     240
gttggtgtcc tgcctgcgct cagg atg agg ggg aat ctg gcc ctg gtg ggc        291
                             Met Arg Gly Asn Leu Ala Leu Val Gly
                               1               5 gtt cta atc agc ctg gcc ttc ctg tca ctg ctg cca tct gga cat cct        339
Val Leu Ile Ser Leu Ala Phe Leu Ser Leu Leu Pro Ser Gly His Pro
 10              15                  20                  25 cag ccg gct ggc gat gac gcc tgc tct gtg cag atc ctc gtc cct ggc        387
Gln Pro Ala Gly Asp Asp Ala Cys Ser Val Gln Ile Leu Val Pro Gly
                 30                  35                  40 ctc aaa ggg gat gcg gga gag aag gga gac aaa ggc gcc ccc gga cgg        435
Leu Lys Gly Asp Ala Gly Glu Lys Gly Asp Lys Gly Ala Pro Gly Arg
             45                  50                  55 cct gga aga gtc ggc ccc acg gga gaa aaa gga gac atg ggg gac aaa        483
Pro Gly Arg Val Gly Pro Thr Gly Glu Lys Gly Asp Met Gly Asp Lys
         60                  65                  70 gga cag aaa ggc agt gtg ggt cgt cat gga aaa att ggt ccc att ggc        531
Gly Gln Lys Gly Ser Val Gly Arg His Gly Lys Ile Gly Pro Ile Gly
     75                  80                  85 tct aaa ggt gag aaa gga gat tcc ggt gac ata gga ccc cct ggt cct        579
Ser Lys Gly Glu Lys Gly Asp Ser Gly Asp Ile Gly Pro Pro Gly Pro
 90                  95                 100                 105 aat gga gaa cca ggc ctc cca tgt gag tgc agc cag ctg cgc aag gcc        627
```

-continued

```
Asn Gly Glu Pro Gly Leu Pro Cys Glu Cys Ser Gln Leu Arg Lys Ala
            110                 115                 120 atc ggg gag atg gac aac cag gtc tct cag ctg acc agc gag ctc aag    675
Ile Gly Glu Met Asp Asn Gln Val Ser Gln Leu Thr Ser Glu Leu Lys
            125                 130                 135 ttc atc aag aat gct gtc gcc ggt gtg cgc gag acg gag agc aag atc    723
Phe Ile Lys Asn Ala Val Ala Gly Val Arg Glu Thr Glu Ser Lys Ile
            140                 145                 150 tac ctg ctg gtg aag gag gag aag cgc tac gcg gac gcc cag ctg tcc    771
Tyr Leu Leu Val Lys Glu Glu Lys Arg Tyr Ala Asp Ala Gln Leu Ser
            155                 160                 165 tgc cag ggc cgc ggg ggc acg ctg agc atg ccc aag gac gag gct gcc    819
Cys Gln Gly Arg Gly Gly Thr Leu Ser Met Pro Lys Asp Glu Ala Ala
170                 175                 180                 185 aat ggc ctg atg gcc gca tac ctg gcg caa gcc ggc ctg gcc cgt gtc    867
Asn Gly Leu Met Ala Ala Tyr Leu Ala Gln Ala Gly Leu Ala Arg Val
                    190                 195                 200 ttc atc ggc atc aac gac ctg gag aag gag ggc gcc ttc gtg tac tct    915
Phe Ile Gly Ile Asn Asp Leu Glu Lys Glu Gly Ala Phe Val Tyr Ser
                    205                 210                 215 gac cac tcc ccc atg cgg acc ttc aac aag tgg cgc agc ggt gag ccc    963
Asp His Ser Pro Met Arg Thr Phe Asn Lys Trp Arg Ser Gly Glu Pro
                    220                 225                 230 aac aat gcc tac gac gag gag gac tgc gtg gag atg gtg gcc tcg ggc    1011
Asn Asn Ala Tyr Asp Glu Glu Asp Cys Val Glu Met Val Ala Ser Gly
                    235                 240                 245 ggc tgg aac gac gtg gcc tgc cac acc acc atg tac ttc atg tgt gag    1059
Gly Trp Asn Asp Val Ala Cys His Thr Thr Met Tyr Phe Met Cys Glu
250                 255                 260                 265 ttt gac aag gag aac atg tgagcctcag gctggggctg cccattgggg           1107
Phe Asp Lys Glu Asn Met
            270 gccccacatg tccctgcagg gttggcaggg acagagccca gaccatggtg ccagccaggg  1167 agctgtccct ctgtgaaggg tggaggctca ctgagtagag ggctgttgtc taaactgaga  1227 aaatggccta tgcttaagag gaaaatgaaa gtgttcctgg ggtgctgtct ctgaagaagc  1287 agagtttcat tacctgtatt gtagccccaa tgtcattatg taattattac ccag        1341
```

<210> SEQ ID NO 2
<211> LENGTH: 271
<212> TYPE: PRT
<213> ORGANISM: Homo Sapiens
<220> FEATURE:
<223> OTHER INFORMATION: Deduced Amino Acid Sequence of Novel Collectin
       from Nucleotide Sequence set out in SEQ ID NO:1.

<400> SEQUENCE: 2

```
Met Arg Gly Asn Leu Ala Leu Val Gly Val Leu Ile Ser Leu Ala Phe
1               5                   10                  15

Leu Ser Leu Leu Pro Ser Gly His Pro Gln Pro Ala Gly Asp Asp Ala
            20                  25                  30

Cys Ser Val Gln Ile Leu Val Pro Gly Leu Lys Gly Asp Ala Gly Glu
        35                  40                  45

Lys Gly Asp Lys Gly Ala Pro Gly Arg Pro Gly Arg Val Gly Pro Thr
    50                  55                  60

Gly Glu Lys Gly Asp Met Gly Asp Lys Gly Gln Lys Gly Ser Val Gly
65                  70                  75                  80

Arg His Gly Lys Ile Gly Pro Ile Gly Ser Lys Gly Glu Lys Gly Asp
                85                  90                  95
```

-continued

```
Ser Gly Asp Ile Gly Pro Pro Gly Pro Asn Gly Glu Pro Gly Leu Pro
            100                 105                 110

Cys Glu Cys Ser Gln Leu Arg Lys Ala Ile Gly Glu Met Asp Asn Gln
        115                 120                 125

Val Ser Gln Leu Thr Ser Glu Leu Lys Phe Ile Lys Asn Ala Val Ala
    130                 135                 140

Gly Val Arg Glu Thr Glu Ser Lys Ile Tyr Leu Leu Val Lys Glu Glu
145                 150                 155                 160

Lys Arg Tyr Ala Asp Ala Gln Leu Ser Cys Gln Arg Gly Gly Thr
                165                 170                 175

Leu Ser Met Pro Lys Asp Glu Ala Ala Asn Gly Leu Met Ala Ala Tyr
            180                 185                 190

Leu Ala Gln Ala Gly Leu Ala Arg Val Phe Ile Gly Ile Asn Asp Leu
        195                 200                 205

Glu Lys Glu Gly Ala Phe Val Tyr Ser Asp His Ser Pro Met Arg Thr
    210                 215                 220

Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
                245                 250                 255

His Thr Thr Met Tyr Phe Met Cys Glu Phe Asp Lys Glu Asn Met
            260                 265                 270

<210> SEQ ID NO 3
<211> LENGTH: 1139
<212> TYPE: DNA
<213> ORGANISM: Homo Sapiens
<220> FEATURE:
<221> NAME/KEY: CDS
<222> LOCATION: (141)..(875)

<400> SEQUENCE: 3
cagaagtttt ggtgaaagtg ctttggccc tgactttgtg gtagcgtgtg tgggtttgtg      60
agtggaacct tcagctttag gttggaaacg gtggctgtgg agagctggac ttttggctgt    120
ggaggtcacg tccctgccca atg tgg tgg gtg cct ccg agt ccc tac ggt tgt    173
                     Met Trp Trp Val Pro Pro Ser Pro Tyr Gly Cys
                      1               5                  10 ctt ccc tgc gcc ctg cca ggg gat gcg gga gag aag gga gac aaa ggc    221
Leu Pro Cys Ala Leu Pro Gly Asp Ala Gly Glu Lys Gly Asp Lys Gly
            15                  20                  25 gcc ccc gga cgg cct gga aga gtc ggc ccc acg gga gaa aaa gga gac    269
Ala Pro Gly Arg Pro Gly Arg Val Gly Pro Thr Gly Glu Lys Gly Asp
        30                  35                  40 atg ggg gac aaa gga cag aaa ggc agt gtg ggt cgt cat gga aaa att    317
Met Gly Asp Lys Gly Gln Lys Gly Ser Val Gly Arg His Gly Lys Ile
    45                  50                  55 ggt ccc att ggc tct aaa ggt gag aaa gga gat tcc ggt gac ata gga    365
Gly Pro Ile Gly Ser Lys Gly Glu Lys Gly Asp Ser Gly Asp Ile Gly
60                  65                  70                  75 ccc cct ggt cct aat gga gaa cca ggc ctc cca tgt gag tgc agc cag    413
Pro Pro Gly Pro Asn Gly Glu Pro Gly Leu Pro Cys Glu Cys Ser Gln
                80                  85                  90 ctg cgc aag gcc atc ggg gag atg gac aac cag gtc tct cag ctg acc    461
Leu Arg Lys Ala Ile Gly Glu Met Asp Asn Gln Val Ser Gln Leu Thr
            95                 100                 105 agc gag ctc aag ttc atc aag aat gct gtc gcc ggt gtg cgc gag acg    509
Ser Glu Leu Lys Phe Ile Lys Asn Ala Val Ala Gly Val Arg Glu Thr
        110                 115                 120
```

```
gag agc aag atc tac ctg ctg gtg aag gag gag aag cgc tac gcg gac      557
Glu Ser Lys Ile Tyr Leu Leu Val Lys Glu Glu Lys Arg Tyr Ala Asp
    125                 130                 135 gcc cag ctg tcc tgc cag ggc cgc ggg ggc acg ctg agc atg ccc aag      605
Ala Gln Leu Ser Cys Gln Gly Arg Gly Gly Thr Leu Ser Met Pro Lys
140                 145                 150                 155 gac gag gct gcc aat ggc ctg atg gcc gca tac ctg gcg caa gcc ggc      653
Asp Glu Ala Ala Asn Gly Leu Met Ala Ala Tyr Leu Ala Gln Ala Gly
                160                 165                 170 ctg gcc cgt gtc ttc atc ggc atc aac gac ctg gag aag gag ggc gcc      701
Leu Ala Arg Val Phe Ile Gly Ile Asn Asp Leu Glu Lys Glu Gly Ala
            175                 180                 185 ttc gtg tac tct gac cac tcc ccc atg cgg acc ttc aac aag tgg cgc      749
Phe Val Tyr Ser Asp His Ser Pro Met Arg Thr Phe Asn Lys Trp Arg
        190                 195                 200 agc ggt gag ccc aac aat gcc tac gac gag gag gac tgc gtg gag atg      797
Ser Gly Glu Pro Asn Asn Ala Tyr Asp Glu Glu Asp Cys Val Glu Met
    205                 210                 215 gtg gcc tcg ggc ggc tgg aac gac gtg gcc tgc cac acc acc atg tac      845
Val Ala Ser Gly Gly Trp Asn Asp Val Ala Cys His Thr Thr Met Tyr
220                 225                 230                 235 ttc atg tgt gag ttt gac aag gag aac atg tgagcctcag gctggggctg        895
Phe Met Cys Glu Phe Asp Lys Glu Asn Met
                240                 245 cccattgggg gccccacatg tccctgcagg gttggcaggg acagagccca gaccatggtg    955
ccagccaggg agctgtccct ctgtgaaggg tggaggctca ctgagtagag ggctgttgtc   1015
taaactgaga aaatggccta tgcttaagag gaaaatgaaa gtgttcctgg ggtgctgtct   1075
ctgaagaagc agagtttcat tacctgtatt gtagccccaa tgtcattatg taattattac   1135
ccag                                                                1139
```

<210> SEQ ID NO 4
<211> LENGTH: 245
<212> TYPE: PRT
<213> ORGANISM: Homo Sapiens
<220> FEATURE:
<223> OTHER INFORMATION: Deduced Amino Acid Sequence of Novel Collectin
      from Nucleotide Sequence set out in SEQ ID NO:3.

<400> SEQUENCE: 4

```
Met Trp Trp Val Pro Pro Ser Pro Tyr Gly Cys Leu Pro Cys Ala Leu
 1               5                  10                  15

Pro Gly Asp Ala Gly Glu Lys Gly Asp Lys Gly Ala Pro Gly Arg Pro
                20                  25                  30

Gly Arg Val Gly Pro Thr Gly Glu Lys Gly Asp Met Gly Asp Lys Gly
            35                  40                  45

Gln Lys Gly Ser Val Gly Arg His Gly Lys Ile Gly Pro Ile Gly Ser
        50                  55                  60

Lys Gly Glu Lys Gly Asp Ser Gly Asp Ile Gly Pro Pro Gly Pro Asn
65                  70                  75                  80

Gly Glu Pro Gly Leu Pro Cys Glu Cys Ser Gln Leu Arg Lys Ala Ile
                85                  90                  95

Gly Glu Met Asp Asn Gln Val Ser Gln Leu Thr Ser Glu Leu Lys Phe
            100                 105                 110

Ile Lys Asn Ala Val Ala Gly Val Arg Glu Thr Glu Ser Lys Ile Tyr
        115                 120                 125

Leu Leu Val Lys Glu Glu Lys Arg Tyr Ala Asp Ala Gln Leu Ser Cys
    130                 135                 140
```

```
Gln Gly Arg Gly Gly Thr Leu Ser Met Pro Lys Asp Glu Ala Ala Asn
145                 150                 155                 160

Gly Leu Met Ala Ala Tyr Leu Ala Gln Ala Gly Leu Ala Arg Val Phe
                165                 170                 175

Ile Gly Ile Asn Asp Leu Glu Lys Glu Gly Ala Phe Val Tyr Ser Asp
            180                 185                 190

His Ser Pro Met Arg Thr Phe Asn Lys Trp Arg Ser Gly Glu Pro Asn
        195                 200                 205

Asn Ala Tyr Asp Glu Glu Asp Cys Val Glu Met Val Ala Ser Gly Gly
    210                 215                 220

Trp Asn Asp Val Ala Cys His Thr Thr Met Tyr Phe Met Cys Glu Phe
225                 230                 235                 240

Asp Lys Glu Asn Met
            245

<210> SEQ ID NO 5
<211> LENGTH: 995
<212> TYPE: DNA
<213> ORGANISM: Homo Sapiens
<220> FEATURE:
<221> NAME/KEY: CDS
<222> LOCATION: (141)..(731)

<400> SEQUENCE: 5
cagaagtttt ggtgaaagtg ctttggccc tgactttgtg gtagcgtgtg tgggtttgtg     60
agtggaacct tcagctttag gttggaaacg gtggctgtgg agagctggac ttttggctgt   120
ggaggtcacg tccctgccca atg tgg tgg gtg cct ccg agt ccc tac ggt tgt   173
                       Met Trp Trp Val Pro Pro Ser Pro Tyr Gly Cys
                         1               5                  10 ctt ccc tgc gcc ctg cca ggt gag aaa gga gat tcc ggt gac ata gga   221
Leu Pro Cys Ala Leu Pro Gly Glu Lys Gly Asp Ser Gly Asp Ile Gly
                15                  20                  25 ccc cct ggt cct aat gga gaa cca ggc ctc cca tgt gag tgc agc cag   269
Pro Pro Gly Pro Asn Gly Glu Pro Gly Leu Pro Cys Glu Cys Ser Gln
        30                  35                  40 ctg cgc aag gcc atc ggg gag atg gac aac cag gtc tct cag ctg acc   317
Leu Arg Lys Ala Ile Gly Glu Met Asp Asn Gln Val Ser Gln Leu Thr
    45                  50                  55 agc gag ctc aag ttc atc aag aat gct gtc gcc ggt gtg cgc gag acg   365
Ser Glu Leu Lys Phe Ile Lys Asn Ala Val Ala Gly Val Arg Glu Thr
60                  65                  70                  75 gag agc aag atc tac ctg ctg gtg aag gag gag aag cgc tac gcg gac   413
Glu Ser Lys Ile Tyr Leu Leu Val Lys Glu Glu Lys Arg Tyr Ala Asp
                80                  85                  90 gcc cag ctg tcc tgc cag ggc cgc ggg ggc acg ctg agc atg ccc aag   461
Ala Gln Leu Ser Cys Gln Gly Arg Gly Gly Thr Leu Ser Met Pro Lys
            95                  100                 105 gac gag gct gcc aat ggc ctg atg gcc gca tac ctg gcg caa gcc ggc   509
Asp Glu Ala Ala Asn Gly Leu Met Ala Ala Tyr Leu Ala Gln Ala Gly
        110                 115                 120 ctg gcc cgt gtc ttc atc ggc atc aac gac ctg gag aag gag ggc gcc   557
Leu Ala Arg Val Phe Ile Gly Ile Asn Asp Leu Glu Lys Glu Gly Ala
    125                 130                 135 ttc gtg tac tct gac cac tcc ccc atg cgg acc ttc aac aag tgg cgc   605
Phe Val Tyr Ser Asp His Ser Pro Met Arg Thr Phe Asn Lys Trp Arg
140                 145                 150                 155 agc ggt gag ccc aac aat gcc tac gac gag gag gac tgc gtg gag atg   653
Ser Gly Glu Pro Asn Asn Ala Tyr Asp Glu Glu Asp Cys Val Glu Met
                160                 165                 170
```

```
gtg gcc tcg ggc ggc tgg aac gac gtg gcc tgc cac acc acc atg tac    701
Val Ala Ser Gly Gly Trp Asn Asp Val Ala Cys His Thr Thr Met Tyr
    175             180             185 ttc atg tgt gag ttt gac aag gag aac atg tgagcctcag gctggggctg     751
Phe Met Cys Glu Phe Asp Lys Glu Asn Met
190             195 ccccattgggg gccccacatg tccctgcagg gttggcaggg acagagccca gaccatggtg  811
ccagccaggg agctgtccct ctgtgaaggg tggaggctca ctgagtagag ggctgttgtc   871
taaactgaga aaatggccta tgcttaagag gaaaatgaaa gtgttcctgg ggtgctgtct   931
ctgaagaagc agagtttcat tacctgtatt gtagccccaa tgtcattatg taattattac   991
ccag                                                                995

<210> SEQ ID NO 6
<211> LENGTH: 197
<212> TYPE: PRT
<213> ORGANISM: Homo Sapiens
<220> FEATURE:
<223> OTHER INFORMATION: Deduced Amino Acid Sequence of Novel Collectin
      from Nucleotide Sequence set out in SEQ ID NO:5.

<400> SEQUENCE: 6

Met Trp Trp Val Pro Pro Ser Pro Tyr Gly Cys Leu Pro Cys Ala Leu
 1               5                  10                  15

Pro Gly Glu Lys Gly Asp Ser Gly Asp Ile Gly Pro Pro Gly Pro Asn
                20                  25                  30

Gly Glu Pro Gly Leu Pro Cys Glu Cys Ser Gln Leu Arg Lys Ala Ile
            35                  40                  45

Gly Glu Met Asp Asn Gln Val Ser Gln Leu Thr Ser Glu Leu Lys Phe
        50                  55                  60

Ile Lys Asn Ala Val Ala Gly Val Arg Glu Thr Glu Ser Lys Ile Tyr
65                  70                  75                  80

Leu Leu Val Lys Glu Glu Lys Arg Tyr Ala Asp Ala Gln Leu Ser Cys
                85                  90                  95

Gln Gly Arg Gly Gly Thr Leu Ser Met Pro Lys Asp Glu Ala Ala Asn
            100                 105                 110

Gly Leu Met Ala Ala Tyr Leu Ala Gln Ala Gly Leu Ala Arg Val Phe
        115                 120                 125

Ile Gly Ile Asn Asp Leu Glu Lys Glu Gly Ala Phe Val Tyr Ser Asp
    130                 135                 140

His Ser Pro Met Arg Thr Phe Asn Lys Trp Arg Ser Gly Glu Pro Asn
145                 150                 155                 160

Asn Ala Tyr Asp Glu Glu Asp Cys Val Glu Met Val Ala Ser Gly Gly
                165                 170                 175

Trp Asn Asp Val Ala Cys His Thr Thr Met Tyr Phe Met Cys Glu Phe
            180                 185                 190

Asp Lys Glu Asn Met
        195

<210> SEQ ID NO 7
<211> LENGTH: 1067
<212> TYPE: DNA
<213> ORGANISM: Homo Sapiens
<220> FEATURE:
<221> NAME/KEY: CDS
<222> LOCATION: (141)..(803)

<400> SEQUENCE: 7
```

```
cagaagttttt ggtgaaagtg ctttggccc tgactttgtg gtagcgtgtg tgggtttgtg        60
agtggaacct tcagctttag gttggaaacg tggctgtgg agagctggac ttttggctgt        120
ggaggtcacg tccctgccca atg tgg tgg gtg cct ccg agt ccc tac ggt tgt      173
                      Met Trp Trp Val Pro Pro Ser Pro Tyr Gly Cys
                       1               5                      10 ctt ccc tgc gcc ctg cca gga gac atg ggg gac aaa gga cag aaa ggc        221
Leu Pro Cys Ala Leu Pro Gly Asp Met Gly Asp Lys Gly Gln Lys Gly
                15                  20                  25 agt gtg ggt cgt cat gga aaa att ggt ccc att ggc tct aaa ggt gag        269
Ser Val Gly Arg His Gly Lys Ile Gly Pro Ile Gly Ser Lys Gly Glu
         30                  35                  40 aaa gga gat tcc ggt gac ata gga ccc cct ggt cct aat gga gaa cca        317
Lys Gly Asp Ser Gly Asp Ile Gly Pro Pro Gly Pro Asn Gly Glu Pro
     45                  50                  55 ggc ctc cca tgt gag tgc agc cag ctg cgc aag gcc atc ggg gag atg        365
Gly Leu Pro Cys Glu Cys Ser Gln Leu Arg Lys Ala Ile Gly Glu Met
 60                  65                  70                  75 gac aac cag gtc tct cag ctg acc agc gag ctc aag ttc atc aag aat        413
Asp Asn Gln Val Ser Gln Leu Thr Ser Glu Leu Lys Phe Ile Lys Asn
                 80                  85                  90 gct gtc gcc ggt gtg cgc gag acg gag agc aag atc tac ctg ctg gtg        461
Ala Val Ala Gly Val Arg Glu Thr Glu Ser Lys Ile Tyr Leu Leu Val
             95                 100                 105 aag gag gag aag cgc tac gcg gac gcc cag ctg tcc tgc cag ggc cgc        509
Lys Glu Glu Lys Arg Tyr Ala Asp Ala Gln Leu Ser Cys Gln Gly Arg
        110                 115                 120 ggg ggc acg ctg agc atg ccc aag gac gag gct gcc aat ggc ctg atg        557
Gly Gly Thr Leu Ser Met Pro Lys Asp Glu Ala Ala Asn Gly Leu Met
125                 130                 135 gcc gca tac ctg gcg caa gcc ggc ctg gcc cgt gtc ttc atc ggc atc        605
Ala Ala Tyr Leu Ala Gln Ala Gly Leu Ala Arg Val Phe Ile Gly Ile
140                 145                 150                 155 aac gac ctg gag aag gag ggc gcc ttc gtg tac tct gac cac tcc ccc        653
Asn Asp Leu Glu Lys Glu Gly Ala Phe Val Tyr Ser Asp His Ser Pro
                160                 165                 170 atg cgg acc ttc aac aag tgg cgc agc ggt gag ccc aac aat gcc tac        701
Met Arg Thr Phe Asn Lys Trp Arg Ser Gly Glu Pro Asn Asn Ala Tyr
            175                 180                 185 gac gag gag gac tgc gtg gag atg gtg gcc tcg ggc ggc tgg aac gac        749
Asp Glu Glu Asp Cys Val Glu Met Val Ala Ser Gly Gly Trp Asn Asp
        190                 195                 200 gtg gcc tgc cac acc acc atg tac ttc atg tgt gag ttt gac aag gag        797
Val Ala Cys His Thr Thr Met Tyr Phe Met Cys Glu Phe Asp Lys Glu
    205                 210                 215 aac atg tgagcctcag gctggggctg cccattgggg gccccacatg tccctgcagg         853
Asn Met
220 gttggcaggg acagagccca gaccatggtg ccagccaggg agctgtccct ctgtgaaggg       913 tggaggctca ctgagtagag ggctgttgtc taaactgaga aaatggccta tgcttaagag       973 gaaaatgaaa gtgttcctgg ggtgctgtct ctgaagaagc agagtttcat tacctgtatt      1033 gtagccccaa tgtcattatg taattattac ccag                                  1067
```

<210> SEQ ID NO 8
<211> LENGTH: 221
<212> TYPE: PRT
<213> ORGANISM: Homo Sapiens
<220> FEATURE:
<223> OTHER INFORMATION: Deduced Amino Acid Sequence of Novel Collectin
      from Nucleotide Sequence set out in SEQ ID NO:7.

<400> SEQUENCE: 8

| Met | Trp | Trp | Val | Pro | Pro | Ser | Pro | Tyr | Gly | Cys | Leu | Pro | Cys | Ala | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Pro Gly Asp Met Gly Asp Lys Gly Gln Lys Gly Ser Val Gly Arg His
            20                  25                  30

Gly Lys Ile Gly Pro Ile Gly Ser Lys Gly Glu Lys Gly Asp Ser Gly
        35                  40                  45

Asp Ile Gly Pro Pro Gly Pro Asn Gly Glu Pro Gly Leu Pro Cys Glu
    50                  55                  60

Cys Ser Gln Leu Arg Lys Ala Ile Gly Glu Met Asp Asn Gln Val Ser
65                  70                  75                  80

Gln Leu Thr Ser Glu Leu Lys Phe Ile Lys Asn Ala Val Ala Gly Val
                85                  90                  95

Arg Glu Thr Glu Ser Lys Ile Tyr Leu Leu Val Lys Glu Glu Lys Arg
            100                 105                 110

Tyr Ala Asp Ala Gln Leu Ser Cys Gln Gly Arg Gly Gly Thr Leu Ser
        115                 120                 125

Met Pro Lys Asp Glu Ala Ala Asn Gly Leu Met Ala Ala Tyr Leu Ala
    130                 135                 140

Gln Ala Gly Leu Ala Arg Val Phe Ile Gly Ile Asn Asp Leu Glu Lys
145                 150                 155                 160

Glu Gly Ala Phe Val Tyr Ser Asp His Ser Pro Met Arg Thr Phe Asn
                165                 170                 175

Lys Trp Arg Ser Gly Glu Pro Asn Asn Ala Tyr Asp Glu Glu Asp Cys
            180                 185                 190

Val Glu Met Val Ala Ser Gly Gly Trp Asn Asp Val Ala Cys His Thr
        195                 200                 205

Thr Met Tyr Phe Met Cys Glu Phe Asp Lys Glu Asn Met
    210                 215                 220

<210> SEQ ID NO 9
<211> LENGTH: 1067
<212> TYPE: DNA
<213> ORGANISM: Homo Sapiens
<220> FEATURE:
<221> NAME/KEY: CDS
<222> LOCATION: (141)..(803)

<400> SEQUENCE: 9

| cagaagtttt ggtgaaagtg gctttggccc tgactttgtg gtagcgtgtg tgggtttgtg | 60 |
|---|---|
| agtggaacct tcagctttag gttggaaacg gtggctgtgg agagctggac ttttggctgt | 120 |

| ggaggtcacg tccctgccca atg tgg tgg gtg cct ccg agt ccc tac ggt tgt | 173 |
|---|---|
|                    Met Trp Trp Val Pro Pro Ser Pro Tyr Gly Cys | |
|                     1               5                       10 | |

| ctt ccc tgc gcc ctg cca ggg gat gcg gga gag aag gga gac aaa ggc | 221 |
|---|---|
| Leu Pro Cys Ala Leu Pro Gly Asp Ala Gly Glu Lys Gly Asp Lys Gly | |
|             15                  20                  25 | |

| gcc ccc gga cgg cct gga aga gtc ggc ccc acg gga gaa aaa ggt gag | 269 |
|---|---|
| Ala Pro Gly Arg Pro Gly Arg Val Gly Pro Thr Gly Glu Lys Gly Glu | |
|         30                  35                  40 | |

| aaa gga gat tcc ggt gac ata gga ccc cct ggt cct aat gga gaa cca | 317 |
|---|---|
| Lys Gly Asp Ser Gly Asp Ile Gly Pro Pro Gly Pro Asn Gly Glu Pro | |
|     45                  50                  55 | |

| ggc ctc cca tgt gag tgc agc cag ctg cgc aag gcc atc ggg gag atg | 365 |
|---|---|
| Gly Leu Pro Cys Glu Cys Ser Gln Leu Arg Lys Ala Ile Gly Glu Met | |
| 60                  65                  70                  75 | |

```
gac aac cag gtc tct cag ctg acc agc gag ctc aag ttc atc aag aat    413
Asp Asn Gln Val Ser Gln Leu Thr Ser Glu Leu Lys Phe Ile Lys Asn
                80                  85                  90 gct gtc gcc ggt gtg cgc gag acg gag agc aag atc tac ctg ctg gtg    461
Ala Val Ala Gly Val Arg Glu Thr Glu Ser Lys Ile Tyr Leu Leu Val
            95                 100                 105 aag gag gag aag cgc tac gcg gac gcc cag ctg tcc tgc cag ggc cgc    509
Lys Glu Glu Lys Arg Tyr Ala Asp Ala Gln Leu Ser Cys Gln Gly Arg
        110                 115                 120 ggg ggc acg ctg agc atg ccc aag gac gag gct gcc aat ggc ctg atg    557
Gly Gly Thr Leu Ser Met Pro Lys Asp Glu Ala Ala Asn Gly Leu Met
    125                 130                 135 gcc gca tac ctg gcg caa gcc ggc ctg gcc cgt gtc ttc atc ggc atc    605
Ala Ala Tyr Leu Ala Gln Ala Gly Leu Ala Arg Val Phe Ile Gly Ile
140                 145                 150                 155 aac gac ctg gag aag gag ggc gcc ttc gtg tac tct gac cac tcc ccc    653
Asn Asp Leu Glu Lys Glu Gly Ala Phe Val Tyr Ser Asp His Ser Pro
                160                 165                 170 atg cgg acc ttc aac aag tgg cgc agc ggt gag ccc aac aat gcc tac    701
Met Arg Thr Phe Asn Lys Trp Arg Ser Gly Glu Pro Asn Asn Ala Tyr
            175                 180                 185 gac gag gag gac tgc gtg gag atg gtg gcc tcg ggc ggc tgg aac gac    749
Asp Glu Glu Asp Cys Val Glu Met Val Ala Ser Gly Gly Trp Asn Asp
        190                 195                 200 gtg gcc tgc cac acc acc atg tac ttc atg tgt gag ttt gac aag gag    797
Val Ala Cys His Thr Thr Met Tyr Phe Met Cys Glu Phe Asp Lys Glu
    205                 210                 215 aac atg tgagcctcag gctggggctg cccattgggg gccccacatg tccctgcagg     853
Asn Met
220 gttggcaggg acagagccca gaccatggtg ccagccaggg agctgtccct ctgtgaaggg    913 tggaggctca ctgagtagag ggctgttgtc taaactgaga aaatggccta tgcttaagag    973 gaaaatgaaa gtgttcctgg ggtgctgtct ctgaagaagc agagtttcat tacctgtatt   1033 gtagccccaa tgtcattatg taattattac ccag                              1067

<210> SEQ ID NO 10
<211> LENGTH: 221
<212> TYPE: PRT
<213> ORGANISM: Homo Sapiens
<220> FEATURE:
<223> OTHER INFORMATION: Deduced Amino Acid Sequence of Novel Collectin
      from Nucleotide Sequence set out in SEQ ID NO:9.

<400> SEQUENCE: 10

Met Trp Trp Val Pro Pro Ser Pro Tyr Gly Cys Leu Pro Cys Ala Leu
 1               5                  10                  15

Pro Gly Asp Ala Gly Glu Lys Gly Asp Lys Gly Ala Pro Gly Arg Pro
            20                  25                  30

Gly Arg Val Gly Pro Thr Gly Glu Lys Gly Glu Lys Gly Asp Ser Gly
        35                  40                  45

Asp Ile Gly Pro Pro Gly Pro Asn Gly Glu Pro Gly Leu Pro Cys Glu
    50                  55                  60

Cys Ser Gln Leu Arg Lys Ala Ile Gly Glu Met Asp Asn Gln Val Ser
65                  70                  75                  80

Gln Leu Thr Ser Glu Leu Lys Phe Ile Lys Asn Ala Val Ala Gly Val
                85                  90                  95

Arg Glu Thr Glu Ser Lys Ile Tyr Leu Leu Val Lys Glu Glu Lys Arg
            100                 105                 110
```

```
Tyr Ala Asp Ala Gln Leu Ser Cys Gln Gly Arg Gly Gly Thr Leu Ser
            115                 120                 125
Met Pro Lys Asp Glu Ala Ala Asn Gly Leu Met Ala Ala Tyr Leu Ala
    130                 135                 140
Gln Ala Gly Leu Ala Arg Val Phe Ile Gly Ile Asn Asp Leu Glu Lys
145                 150                 155                 160
Glu Gly Ala Phe Val Tyr Ser Asp His Ser Pro Met Arg Thr Phe Asn
                165                 170                 175
Lys Trp Arg Ser Gly Glu Pro Asn Asn Ala Tyr Asp Glu Glu Asp Cys
            180                 185                 190
Val Glu Met Val Ala Ser Gly Gly Trp Asn Asp Val Ala Cys His Thr
        195                 200                 205
Thr Met Tyr Phe Met Cys Glu Phe Asp Lys Glu Asn Met
    210                 215                 220

<210> SEQ ID NO 11
<211> LENGTH: 45
<212> TYPE: PRT
<213> ORGANISM: Homo Sapiens
<220> FEATURE:
<223> OTHER INFORMATION: Deduced Amino Acid Sequence of a collagen-like
      domain of mutated Novel Collectin.

<400> SEQUENCE: 11

Gly Asp Ala Gly Glu Lys Gly Asp Lys Gly Ala Pro Gly Arg Pro Gly
  1               5                   10                  15
Arg Val Gly Pro Thr Gly Glu Lys Gly Glu Lys Gly Asp Ser Gly Asp
                20                  25                  30
Ile Gly Pro Pro Gly Pro Asn Gly Glu Pro Gly Leu Pro
                35                  40                  45

<210> SEQ ID NO 12
<211> LENGTH: 1522
<212> TYPE: DNA
<213> ORGANISM: Mus musculus
<220> FEATURE:
<221> NAME/KEY: CDS
<222> LOCATION: (157)..(969)

<400> SEQUENCE: 12
cagcccagcg aatctctctg agctggactg cagctggtct ctgtaaataa cagccatgag      60
gctccttgga gcagtgtctc tgccagccgg tgactgtcag gacagctcct tcgcctagtg     120
tgcatccagg agtctagtgt cctgcctgca ctcatg atg atg agg gac ctg gct      174
                                  Met Met Arg Asp Leu Ala
                                    1               5 ctt gca ggc atg ctg att agc ctg gct ttc ctg tcc ctg ctg cca tct      222
Leu Ala Gly Met Leu Ile Ser Leu Ala Phe Leu Ser Leu Leu Pro Ser
                10                  15                  20 gga tgt cct cag cag acc aca gag gac gcc tgc tct gtg cag att ctt      270
Gly Cys Pro Gln Gln Thr Thr Glu Asp Ala Cys Ser Val Gln Ile Leu
            25                  30                  35 gtc ccc ggc ctc aaa ggg gat gca gga gaa aag gga gac aaa gga gcc      318
Val Pro Gly Leu Lys Gly Asp Ala Gly Glu Lys Gly Asp Lys Gly Ala
    40                  45                  50 cca gga cgg cca gga aga gtc ggc cct aca gga gaa aaa gga gac atg      366
Pro Gly Arg Pro Gly Arg Val Gly Pro Thr Gly Glu Lys Gly Asp Met
55                  60                  65                  70 ggg gac aaa gga cag aaa ggc act gtg ggc cgc cat gga aaa att ggt      414
Gly Asp Lys Gly Gln Lys Gly Thr Val Gly Arg His Gly Lys Ile Gly
                75                  80                  85
```

| | | |
|---|---|---|
| ccc att ggc gca aaa ggt gaa aaa gga gat tct ggt gat atc gga ccc<br>Pro Ile Gly Ala Lys Gly Glu Lys Gly Asp Ser Gly Asp Ile Gly Pro<br>                90                        95                      100 | 462 |
| cct ggc ccc agt gga gaa cct ggt att cca tgt gag tgc agt cag ctg<br>Pro Gly Pro Ser Gly Glu Pro Gly Ile Pro Cys Glu Cys Ser Gln Leu<br>                105                     110                    115 | 510 |
| agg aag gct att ggg gag atg gac aac cag gtc act caa ctg aca act<br>Arg Lys Ala Ile Gly Glu Met Asp Asn Gln Val Thr Gln Leu Thr Thr<br>120                        125                     130 | 558 |
| gag cta aaa ttc ata aaa aat gct gtt gct ggc gtg cgc gag act gag<br>Glu Leu Lys Phe Ile Lys Asn Ala Val Ala Gly Val Arg Glu Thr Glu<br>135                    140                     145                 150 | 606 |
| agc aag atc tac ctg ctg gtg aag gag gag aag cgg tac gca gat gcc<br>Ser Lys Ile Tyr Leu Leu Val Lys Glu Glu Lys Arg Tyr Ala Asp Ala<br>                155                     160                    165 | 654 |
| cag ctg tcc tgc caa gcc cga ggc ggc aca ctg agc atg ccc aaa gac<br>Gln Leu Ser Cys Gln Ala Arg Gly Gly Thr Leu Ser Met Pro Lys Asp<br>                170                     175                    180 | 702 |
| gag gca gcc aat ggc ctg atg gct tca tac ctg gca cag gct ggc ctg<br>Glu Ala Ala Asn Gly Leu Met Ala Ser Tyr Leu Ala Gln Ala Gly Leu<br>                    185                     190                    195 | 750 |
| gcc cga gtc ttc atc ggt atc aat gac ctg gag aaa gaa ggt gct ttc<br>Ala Arg Val Phe Ile Gly Ile Asn Asp Leu Glu Lys Glu Gly Ala Phe<br>200                        205                     210 | 798 |
| gtg tac tcg gac cgc tcc ccc atg cag acc ttc aac aag tgg cgc agt<br>Val Tyr Ser Asp Arg Ser Pro Met Gln Thr Phe Asn Lys Trp Arg Ser<br>215                        220                     225                 230 | 846 |
| gga gag ccc aac aac gcc tat gat gag gag gac tgt gtg gag atg gtg<br>Gly Glu Pro Asn Asn Ala Tyr Asp Glu Glu Asp Cys Val Glu Met Val<br>                    235                     240                    245 | 894 |
| gcc tca ggt ggc tgg aat gat gtg gcc tgc cac att acc atg tac ttc<br>Ala Ser Gly Gly Trp Asn Asp Val Ala Cys His Ile Thr Met Tyr Phe<br>                250                     255                    260 | 942 |
| atg tgc gag ttt gac aaa gag aac ttg tgagagccga caggggagat<br>Met Cys Glu Phe Asp Lys Glu Asn Leu<br>                265                     270 | 989 |
| ggccatctga acgccacctt ttatagacac cagcggccac aaactaaccc tgagcaccag | 1049 |
| tcgccatgtc tgcgggttcc tctctgcatg gaagtgccgg gcctcattga cagttggaag | 1109 |
| ggctgtttga accgtaggag gggagaaacc ttgcttccgg ggctgttctg aataggtggc | 1169 |
| gtattatcac ctttgtcaga cgttcattat ggctaaccac tcggaaggat gctgtgaagc | 1229 |
| tcttgtcttg gtccagcata gtaaattttg cagcagtcat caaactggct ataggggcag | 1289 |
| gagttgccgc ccaccctata aagtacacag agtgcccagg tggtgaccaa tgtttctata | 1349 |
| ggttatgcta tcacatagat tcctttcact attatccggg taggaagact gctgctctgc | 1409 |
| ttcacatcca tatttcagga aaacaaataa atcctctgat ttctgctaaa aaaaaaaaa | 1469 |
| aaaaaaaaaa aaaaaaaaaa aaaaaaaaaa aaaaaaaaaa aaaaaaaaaa aaa | 1522 |

<210> SEQ ID NO 13
<211> LENGTH: 271
<212> TYPE: PRT
<213> ORGANISM: Mus musculus
<220> FEATURE:
<223> OTHER INFORMATION: Deduced Amino Acid Sequence of Novel Collectin
    from Nucleotide Sequence set out in SEQ ID NO:12.

<400> SEQUENCE: 13

Met Met Arg Asp Leu Ala Leu Ala Gly Met Leu Ile Ser Leu Ala Phe
1               5                   10                  15

-continued

```
Leu Ser Leu Leu Pro Ser Gly Cys Pro Gln Gln Thr Thr Glu Asp Ala
             20                  25                  30

Cys Ser Val Gln Ile Leu Val Pro Gly Leu Lys Gly Asp Ala Gly Glu
         35                  40                  45

Lys Gly Asp Lys Gly Ala Pro Gly Arg Pro Gly Arg Val Gly Pro Thr
 50                  55                  60

Gly Glu Lys Gly Asp Met Gly Asp Lys Gly Gln Lys Gly Thr Val Gly
 65                  70                  75                  80

Arg His Gly Lys Ile Gly Pro Ile Gly Ala Lys Gly Glu Lys Gly Asp
                 85                  90                  95

Ser Gly Asp Ile Gly Pro Pro Gly Pro Ser Gly Glu Pro Gly Ile Pro
            100                 105                 110

Cys Glu Cys Ser Gln Leu Arg Lys Ala Ile Gly Glu Met Asp Asn Gln
        115                 120                 125

Val Thr Gln Leu Thr Thr Glu Leu Lys Phe Ile Lys Asn Ala Val Ala
130                 135                 140

Gly Val Arg Glu Thr Glu Ser Lys Ile Tyr Leu Leu Val Lys Glu Glu
145                 150                 155                 160

Lys Arg Tyr Ala Asp Ala Gln Leu Ser Cys Gln Ala Arg Gly Gly Thr
                165                 170                 175

Leu Ser Met Pro Lys Asp Glu Ala Ala Asn Gly Leu Met Ala Ser Tyr
            180                 185                 190

Leu Ala Gln Ala Gly Leu Ala Arg Val Phe Ile Gly Ile Asn Asp Leu
        195                 200                 205

Glu Lys Glu Gly Ala Phe Val Tyr Ser Asp Arg Ser Pro Met Gln Thr
    210                 215                 220

Phe Asn Lys Trp Arg Ser Gly Glu Pro Asn Asn Ala Tyr Asp Glu Glu
225                 230                 235                 240

Asp Cys Val Glu Met Val Ala Ser Gly Gly Trp Asn Asp Val Ala Cys
                245                 250                 255

His Ile Thr Met Tyr Phe Met Cys Glu Phe Asp Lys Glu Asn Leu
            260                 265                 270

<210> SEQ ID NO 14
<211> LENGTH: 159
<212> TYPE: PRT
<213> ORGANISM: Homo sapiens
<220> FEATURE:
<223> OTHER INFORMATION: Known CRD amino acid sequence of reported CL-L1
      which was employed for searching EST data base.

<400> SEQUENCE: 14

Cys Asp Cys Gly Arg Tyr Arg Lys Phe Val Gly Gln Leu Asp Ile Ser
  1               5                  10                  15

Ile Ala Arg Leu Lys Thr Ser Met Lys Phe Val Lys Asn Val Ile Ala
             20                  25                  30

Gly Ile Arg Glu Thr Glu Glu Lys Phe Tyr Tyr Ile Val Gln Glu Glu
         35                  40                  45

Lys Asn Tyr Arg Glu Ser Leu Thr His Cys Arg Ile Arg Gly Gly Met
 50                  55                  60

Leu Ala Met Pro Lys Asp Glu Ala Ala Asn Thr Leu Ile Ala Asp Tyr
 65                  70                  75                  80

Val Ala Lys Ser Gly Phe Phe Arg Val Phe Ile Gly Val Asn Asp Leu
                 85                  90                  95

Glu Arg Glu Gly Gln Tyr Met Phe Thr Asp Asn Thr Pro Leu Gln Asn
            100                 105                 110
```

```
Tyr Ser Asn Trp Asn Glu Gly Glu Pro Ser Asp Pro Tyr Gly His Glu
        115                 120                 125

Asp Cys Val Glu Met Leu Ser Ser Gly Arg Trp Asn Asp Thr Glu Cys
130                 135                 140

His Leu Thr Met Tyr Phe Val Cys Glu Phe Ile Lys Lys Lys Lys
145                 150                 155

<210> SEQ ID NO 15
<211> LENGTH: 619
<212> TYPE: DNA
<213> ORGANISM: Artificial Sequence
<220> FEATURE:
<223> OTHER INFORMATION: Consensus nucleotide sequence of novel
      collectin derived from several nucleotide sequences obtained from
      EST data base.
<220> FEATURE:
<221> NAME/KEY: misc_feature
<222> LOCATION: 118
<223> OTHER INFORMATION: N = A or T or G or C
<220> FEATURE:
<221> NAME/KEY: misc_feature
<222> LOCATION: 119
<223> OTHER INFORMATION: N = A or T or G or C

<400> SEQUENCE: 15
ttctcagatg attcctgtgc atggcgaagt ttggaaactc tgagtgttgc ttttgagatc      60
agacatacag tgctatccat tggtgccctc gtgaggatg gaacttactt gttgactnnt     120
gccacaccac catgtacttc atgtgtgagt ttgacaagga gaacatgtga ccctcaggct    180
ggggctgccc attgggggcc ccacatgtcc ctgcagggtt ggcagggaca gagcccagac    240
catggtgcca gccagggagc tgtccctctg tgaaggtggg aggctcactg agtagagggc    300
tgttgtctaa actgagaaaa tggcctatgc ttaagaggaa aatgaaagtg ttcctggggt    360
gctgtctctg aagaagcaga gtttcattac ctgtattgta gccccaatgt cattatgtaa    420
ttattaccca gaattgctct tccataaagc ttgtgccttt gtccaagcta acaataaaa     480 tctttaagta gtgcagtagt taagtccaaa aagtggcaat ggggtcttga aaaaaaaaa    540 aaaaatttat aaaaaaaaaa gaactcactt tgaccaacac ttctgtaaat tacattacaa    600
tataggttcc ttcacacta                                                619

<210> SEQ ID NO 16
<211> LENGTH: 21
<212> TYPE: DNA
<213> ORGANISM: Artificial Sequence
<220> FEATURE:
<223> OTHER INFORMATION: Synthetic primer CAP1 for cloning 5'-upstream
      region of novel collectin.

<400> SEQUENCE: 16 agatttttatt gtatagcttg g                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic primer CAP2 for cloning 5'-upstream
      region of novel collectin.

<400> SEQUENCE: 17
ctgggtaata attacataat g                                               21

<210> SEQ ID NO 18
<211> LENGTH: 21
```

```
<212> TYPE: DNA
<213> ORGANISM: Artificial Sequence
<220> FEATURE:
<223> OTHER INFORMATION: Synthetic primer TriplEx-F1 for cloning
      5'-upstream region of novel collectin.

<400> SEQUENCE: 18
aagctccgag atctggacga g                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic primer TriplEx-F2 for cloning
      5'-upstream region of novel collectin.

<400> SEQUENCE: 19
ctcgggaagc gcgccattgt g                                              21

<210> SEQ ID NO 20
<211> LENGTH: 24
<212> TYPE: DNA
<213> ORGANISM: Artificial Sequence
<220> FEATURE:
<223> OTHER INFORMATION: Synthetic M13 Universal primer for sequencing
      novel collectin.

<400> SEQUENCE: 20
cgacgttgta aaacgacggc cagt                                           24

<210> SEQ ID NO 21
<211> LENGTH: 17
<212> TYPE: DNA
<213> ORGANISM: Artificial Sequence
<220> FEATURE:
<223> OTHER INFORMATION: Synthetic M13 Reverse primer for sequencing
      novel collectin.

<400> SEQUENCE: 21
caggaaacag ctatgac                                                   17

<210> SEQ ID NO 22
<211> LENGTH: 20
<212> TYPE: DNA
<213> ORGANISM: Artificial Sequence
<220> FEATURE:
<223> OTHER INFORMATION: Synthetic primer CAP3 for further cloning of
      5'-upstream region of novel collectin.

<400> SEQUENCE: 22
ggtcctatgt caccggaatc                                                20

<210> SEQ ID NO 23
<211> LENGTH: 21
<212> TYPE: DNA
<213> ORGANISM: Artificial Sequence
<220> FEATURE:
<223> OTHER INFORMATION: Synthetic primer CAP4 for further cloning of
      5'-upstream region of novel collectin.

<400> SEQUENCE: 23
ttccatgacg acccacactg c                                              21

<210> SEQ ID NO 24
<211> LENGTH: 21
<212> TYPE: DNA
<213> ORGANISM: Artificial Sequence
```

```
<220> FEATURE:
<223> OTHER INFORMATION: Synthetic primer 1RC2 for further cloning of
      5'-upstream region of novel collectin.

<400> SEQUENCE: 24
caaggtacgc cacagcgtat g                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic primer 2RC2 for further cloning of
      5'-upstream region of novel collectin.

<400> SEQUENCE: 25
gtacgccaca gcgtatgatg c                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic primer RTF1 for RT-PCR to determine
      tissue distribution of novel collectin.

<400> SEQUENCE: 26
agattccggt gacataggac c                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic primer RTR1 for RT-PCR to determine
      tissue distribution of novel collectin.

<400> SEQUENCE: 27
tggtctgggc tctgtccctg c                                              21

<210> SEQ ID NO 28
<211> LENGTH: 21
<212> TYPE: DNA
<213> ORGANISM: Artificial Sequence
<220> FEATURE:
<223> OTHER INFORMATION: Synthetic actin sense primer for RT-PCR to
      determine control level.

<400> SEQUENCE: 28
caagagatgg ccacggctgc t                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic actin anti-sense primer for RT-PCR to
      determine control level.

<400> SEQUENCE: 29
tccttctgca tcctgtcggc a                                              21

<210> SEQ ID NO 30
<211> LENGTH: 24
<212> TYPE: DNA
<213> ORGANISM: Artificial Sequence
<220> FEATURE:
<223> OTHER INFORMATION: Synthetic primer RTF2 for amplification of CL-
```

```
                              L2-1.

<400> SEQUENCE: 30
atgaggggga atctggccct ggtg                                           24

<210> SEQ ID NO 31
<211> LENGTH: 23
<212> TYPE: DNA
<213> ORGANISM: Artificial Sequence
<220> FEATURE:
<223> OTHER INFORMATION: Synthetic primer RTR2 for amplification of CL-
      L2-1.

<400> SEQUENCE: 31
catgttctcc ttgtcaaact cac                                            23

<210> SEQ ID NO 32
<211> LENGTH: 22
<212> TYPE: DNA
<213> ORGANISM: Artificial Sequence
<220> FEATURE:
<223> OTHER INFORMATION: Synthetic primer RTF3 for amplification of CL-
      L2-2.

<400> SEQUENCE: 32
atgtggtggg tgcctccgag tc                                             22

<210> SEQ ID NO 33
<211> LENGTH: 41
<212> TYPE: DNA
<213> ORGANISM: Artificial Sequence
<220> FEATURE:
<223> OTHER INFORMATION: Synthetic primer CL-L2-1F for amplification of
      CL-L2-1.

<400> SEQUENCE: 33
gggaagcttc gatcaggatg aggggaatc tggccctggt g                         41

<210> SEQ ID NO 34
<211> LENGTH: 32
<212> TYPE: DNA
<213> ORGANISM: Artificial Sequence
<220> FEATURE:
<223> OTHER INFORMATION: Synthetic primer CL-L2-1R for amplification of
      CL-L2-1.

<400> SEQUENCE: 34
gggctcgagc atgttctcct tgtcaaactc ac                                  32

<210> SEQ ID NO 35
<211> LENGTH: 46
<212> TYPE: DNA
<213> ORGANISM: Artificial Sequence
<220> FEATURE:
<223> OTHER INFORMATION: Synthetic primer CL-L2-2F for amplification of
      CL-L2-2.

<400> SEQUENCE: 35
gggaagcttc cagcacaatg tggtgggtgc ctccgagtcc ctggtg                   46

<210> SEQ ID NO 36
<211> LENGTH: 1197
<212> TYPE: DNA
<213> ORGANISM: Homo Sapiens
<220> FEATURE:
<221> NAME/KEY: CDS
<222> LOCATION: (265)..(933)
```

<400> SEQUENCE: 36

```
cgcggccgcg tcgacggacg gtggacgcag cgcagacagg aagctccccg agataacgct      60
gcggccgggc ggcctgattt gctgggctgt ctgatggccc gggccgaggc ttctccctgc     120
gcctgggact gcgccgcct ctctaaatag cagccatgag gcgcctgggg gcagtgtcct      180
cgcggccgcg tcgaccgacg gccgcagtcg acgccccgtt cgcctagcgc gtgctcagga     240
gttggtgtcc tgcctgcgct cagg atg agg ggg aat ctg gcc ctg gtg ggc        291
                             Met Arg Gly Asn Leu Ala Leu Val Gly
                              1               5 gtt cta atc agc ctg gcc ttc ctg tca ctg ctg cca tct gga cat cct       339
Val Leu Ile Ser Leu Ala Phe Leu Ser Leu Leu Pro Ser Gly His Pro
 10              15                  20                  25 cag ccg gct ggc gat gac gcc tgc tct gtg cag atc ctc gtc cct ggc       387
Gln Pro Ala Gly Asp Asp Ala Cys Ser Val Gln Ile Leu Val Pro Gly
             30                  35                  40 ctc aaa ggt gag aaa gga gat tcc ggt gac ata gga ccc cct ggt cct       435
Leu Lys Gly Glu Lys Gly Asp Ser Gly Asp Ile Gly Pro Pro Gly Pro
         45                  50                  55 aat gga gaa cca ggc ctc cca tgt gag tgc agc cag ctg cgc aag gcc       483
Asn Gly Glu Pro Gly Leu Pro Cys Glu Cys Ser Gln Leu Arg Lys Ala
     60                  65                  70 atc ggg gag atg gac aac cag gtc tct cag ctg acc agc gag ctc aag       531
Ile Gly Glu Met Asp Asn Gln Val Ser Gln Leu Thr Ser Glu Leu Lys
 75                  80                  85 ttc atc aag aat gct gtc gcc ggt gtg cgc gag acg gag agc aag atc       579
Phe Ile Lys Asn Ala Val Ala Gly Val Arg Glu Thr Glu Ser Lys Ile
 90                  95                 100                 105 tac ctg ctg gtg aag gag gag aag cgc tac gcg gac gcc cag ctg tcc       627
Tyr Leu Leu Val Lys Glu Glu Lys Arg Tyr Ala Asp Ala Gln Leu Ser
             110                 115                 120 tgc cag ggc cgc ggg ggc acg ctg agc atg ccc aag gac gag gct gcc       675
Cys Gln Gly Arg Gly Gly Thr Leu Ser Met Pro Lys Asp Glu Ala Ala
         125                 130                 135 aat ggc ctg atg gcc gca tac ctg gcg caa gcc ggc ctg gcc cgt gtc       723
Asn Gly Leu Met Ala Ala Tyr Leu Ala Gln Ala Gly Leu Ala Arg Val
     140                 145                 150 ttc atc ggc atc aac gac ctg gag aag gag ggc gcc ttc gtg tac tct       771
Phe Ile Gly Ile Asn Asp Leu Glu Lys Glu Gly Ala Phe Val Tyr Ser
 155                 160                 165 gac cac tcc ccc atg cgg acc ttc aac aag tgg cgc agc ggt gag ccc       819
Asp His Ser Pro Met Arg Thr Phe Asn Lys Trp Arg Ser Gly Glu Pro
170                 175                 180                 185 aac aat gcc tac gac gag gag gac tgc gtg gag atg gtg gcc tcg ggc       867
Asn Asn Ala Tyr Asp Glu Glu Asp Cys Val Glu Met Val Ala Ser Gly
             190                 195                 200 ggc tgg aac gac gtg gcc tgc cac acc acc atg tac ttc atg tgt gag       915
Gly Trp Asn Asp Val Ala Cys His Thr Thr Met Tyr Phe Met Cys Glu
         205                 210                 215 ttt gac aag gag aac atg tgagcctcag gctggggctg cccattgggg              963
Phe Asp Lys Glu Asn Met
         220 gccccacatg tccctgcagg gttggcaggg acagagccca gaccatggtg ccagccaggg    1023 agctgtccct ctgtgaaggg tggaggctca ctgagtagag ggctgttgtc taaactgaga    1083 aaatggccta tgcttaagag gaaaatgaaa gtgttcctgg ggtgctgtct ctgaagaagc    1143 agagtttcat tacctgtatt gtagccccaa tgtcattatg taattattac ccag          1197
```

<210> SEQ ID NO 37

```
<211> LENGTH: 223
<212> TYPE: PRT
<213> ORGANISM: Homo Sapiens
<220> FEATURE:
<223> OTHER INFORMATION: Deduced Amino Acid Sequence of Novel Collectin
      variant from Nucleotide Sequence set out in SEQ ID NO:36.

<400> SEQUENCE: 37

Met Arg Gly Asn Leu Ala Leu Val Gly Val Leu Ile Ser Leu Ala Phe
 1               5                  10                  15

Leu Ser Leu Leu Pro Ser Gly His Pro Gln Pro Ala Gly Asp Asp Ala
            20                  25                  30

Cys Ser Val Gln Ile Leu Val Pro Gly Leu Lys Gly Glu Lys Gly Asp
        35                  40                  45

Ser Gly Asp Ile Gly Pro Pro Gly Pro Asn Gly Glu Pro Gly Leu Pro
    50                  55                  60

Cys Glu Cys Ser Gln Leu Arg Lys Ala Ile Gly Glu Met Asp Asn Gln
65                  70                  75                  80

Val Ser Gln Leu Thr Ser Glu Leu Lys Phe Ile Lys Asn Ala Val Ala
                85                  90                  95

Gly Val Arg Glu Thr Glu Ser Lys Ile Tyr Leu Leu Val Lys Glu Glu
            100                 105                 110

Lys Arg Tyr Ala Asp Ala Gln Leu Ser Cys Gln Gly Arg Gly Gly Thr
        115                 120                 125

Leu Ser Met Pro Lys Asp Glu Ala Ala Asn Gly Leu Met Ala Ala Tyr
    130                 135                 140

Leu Ala Gln Ala Gly Leu Ala Arg Val Phe Ile Gly Ile Asn Asp Leu
145                 150                 155                 160

Glu Lys Glu Gly Ala Phe Val Tyr Ser Asp His Ser Pro Met Arg Thr
                165                 170                 175

Phe Asn Lys Trp Arg Ser Gly Glu Pro Asn Asn Ala Tyr Asp Glu Glu
            180                 185                 190

Asp Cys Val Glu Met Val Ala Ser Gly Gly Trp Asn Asp Val Ala Cys
        195                 200                 205

His Thr Thr Met Tyr Phe Met Cys Glu Phe Asp Lys Glu Asn Met
    210                 215                 220

<210> SEQ ID NO 38
<211> LENGTH: 1269
<212> TYPE: DNA
<213> ORGANISM: Homo Sapiens
<220> FEATURE:
<221> NAME/KEY: CDS
<222> LOCATION: (265)..(1005)

<400> SEQUENCE: 38
cgcggccgcg tcgacggacg gtggacgcag cgcagacagg aagctccccg agataacgct      60
gcggccgggc ggcctgattt gctgggctgt ctgatggccc gggccgaggc ttctccctgc     120
gcctgggact gcggccgcct ctctaaatag cagccatgag gcgcctgggg gcagtgtcct     180
cgcggccgcg tcgaccgacg gccgcagtcg acgccccgtt cgcctagcgc gtgctcagga     240
gttggtgtcc tgcctgcgct cagg atg agg ggg aat ctg gcc ctg gtg ggc        291
                            Met Arg Gly Asn Leu Ala Leu Val Gly
                             1               5 gtt cta atc agc ctg gcc ttc ctg tca ctg ctg cca tct gga cat cct        339
Val Leu Ile Ser Leu Ala Phe Leu Ser Leu Leu Pro Ser Gly His Pro
 10                  15                  20                  25 cag ccg gct ggc gat gac gcc tgc tct gtg cag atc ctc gtc cct ggc        387
Gln Pro Ala Gly Asp Asp Ala Cys Ser Val Gln Ile Leu Val Pro Gly
```

```
                 30                  35                  40
ctc aaa gga gac atg ggg gac aaa gga cag aaa ggc agt gtg ggt cgt    435
Leu Lys Gly Asp Met Gly Asp Lys Gly Gln Lys Gly Ser Val Gly Arg
             45                  50                  55 cat gga aaa att ggt ccc att ggc tct aaa ggt gag aaa gga gat tcc    483
His Gly Lys Ile Gly Pro Ile Gly Ser Lys Gly Glu Lys Gly Asp Ser
         60                  65                  70 ggt gac ata gga ccc cct ggt cct aat gga gaa cca ggc ctc cca tgt    531
Gly Asp Ile Gly Pro Pro Gly Pro Asn Gly Glu Pro Gly Leu Pro Cys
     75                  80                  85 gag tgc agc cag ctg cgc aag gcc atc ggg gag atg gac aac cag gtc    579
Glu Cys Ser Gln Leu Arg Lys Ala Ile Gly Glu Met Asp Asn Gln Val
 90                  95                 100                 105 tct cag ctg acc agc gag ctc aag ttc atc aag aat gct gtc gcc ggt    627
Ser Gln Leu Thr Ser Glu Leu Lys Phe Ile Lys Asn Ala Val Ala Gly
                110                 115                 120 gtg cgc gag acg gag agc aag atc tac ctg ctg gtg aag gag gag aag    675
Val Arg Glu Thr Glu Ser Lys Ile Tyr Leu Leu Val Lys Glu Glu Lys
            125                 130                 135 cgc tac gcg gac gcc cag ctg tcc tgc cag ggc cgc ggg ggc acg ctg    723
Arg Tyr Ala Asp Ala Gln Leu Ser Cys Gln Gly Arg Gly Gly Thr Leu
        140                 145                 150 agc atg ccc aag gac gag gct gcc aat ggc ctg atg gcc gca tac ctg    771
Ser Met Pro Lys Asp Glu Ala Ala Asn Gly Leu Met Ala Ala Tyr Leu
    155                 160                 165 gcg caa gcc ggc ctg gcc cgt gtc ttc atc ggc atc aac gac ctg gag    819
Ala Gln Ala Gly Leu Ala Arg Val Phe Ile Gly Ile Asn Asp Leu Glu
170                 175                 180                 185 aag gag ggc gcc ttc gtg tac tct gac cac tcc ccc atg cgg acc ttc    867
Lys Glu Gly Ala Phe Val Tyr Ser Asp His Ser Pro Met Arg Thr Phe
                190                 195                 200 aac aag tgg cgc agc ggt gag ccc aac aat gcc tac gac gag gag gac    915
Asn Lys Trp Arg Ser Gly Glu Pro Asn Asn Ala Tyr Asp Glu Glu Asp
            205                 210                 215 tgc gtg gag atg gtg gcc tcg ggc ggc tgg aac gac gtg gcc tgc cac    963
Cys Val Glu Met Val Ala Ser Gly Gly Trp Asn Asp Val Ala Cys His
        220                 225                 230 acc acc atg tac ttc atg tgt gag ttt gac aag gag aac atg           1005
Thr Thr Met Tyr Phe Met Cys Glu Phe Asp Lys Glu Asn Met
    235                 240                 245 tgagcctcag gctggggctg cccattgggg gccccacatg tccctgcagg gttggcaggg  1065
acagagccca gaccatggtg ccagccaggg agctgtccct ctgtgaaggg tggaggctca  1125
ctgagtagag ggctgttgtc taaactgaga aaatggccta tgcttaagag gaaaatgaaa  1185
gtgttcctgg ggtgctgtct ctgaagaagc agagtttcat tacctgtatt gtagccccaa  1245
tgtcattatg taattattac ccag                                        1269

<210> SEQ ID NO 39
<211> LENGTH: 247
<212> TYPE: PRT
<213> ORGANISM: Homo Sapiens
<220> FEATURE:
<223> OTHER INFORMATION: Deduced Amino Acid Sequence of Novel Collectin
      variant from Nucleotide Sequence set out in SEQ ID NO:38.

<400> SEQUENCE: 39

Met Arg Gly Asn Leu Ala Leu Val Gly Val Leu Ile Ser Leu Ala Phe
 1               5                  10                  15

Leu Ser Leu Leu Pro Ser Gly His Pro Gln Pro Ala Gly Asp Asp Ala
            20                  25                  30
```

```
Cys Ser Val Gln Ile Leu Val Pro Gly Leu Lys Gly Asp Met Gly Asp
         35                  40                  45

Lys Gly Gln Lys Gly Ser Val Gly Arg His Gly Lys Ile Gly Pro Ile
 50                  55                  60

Gly Ser Lys Gly Glu Lys Gly Asp Ser Gly Asp Ile Gly Pro Pro Gly
 65                  70                  75                  80

Pro Asn Gly Glu Pro Gly Leu Pro Cys Glu Cys Ser Gln Leu Arg Lys
             85                  90                  95

Ala Ile Gly Glu Met Asp Asn Gln Val Ser Gln Leu Thr Ser Glu Leu
            100                 105                 110

Lys Phe Ile Lys Asn Ala Val Ala Gly Val Arg Glu Thr Glu Ser Lys
        115                 120                 125

Ile Tyr Leu Leu Val Lys Glu Glu Lys Arg Tyr Ala Asp Ala Gln Leu
    130                 135                 140

Ser Cys Gln Gly Arg Gly Gly Thr Leu Ser Met Pro Lys Asp Glu Ala
145                 150                 155                 160

Ala Asn Gly Leu Met Ala Ala Tyr Leu Ala Gln Ala Gly Leu Ala Arg
                165                 170                 175

Val Phe Ile Gly Ile Asn Asp Leu Glu Lys Glu Gly Ala Phe Val Tyr
            180                 185                 190

Ser Asp His Ser Pro Met Arg Thr Phe Asn Lys Trp Arg Ser Gly Glu
        195                 200                 205

Pro Asn Asn Ala Tyr Asp Glu Glu Asp Cys Val Glu Met Val Ala Ser
    210                 215                 220

Gly Gly Trp Asn Asp Val Ala Cys His Thr Thr Met Tyr Phe Met Cys
225                 230                 235                 240

Glu Phe Asp Lys Glu Asn Met
                245

<210> SEQ ID NO 40
<211> LENGTH: 1269
<212> TYPE: DNA
<213> ORGANISM: Homo Sapiens
<220> FEATURE:
<221> NAME/KEY: CDS
<222> LOCATION: (265)..(1005)

<400> SEQUENCE: 40
cgcggccgcg tcgacggacg gtggacgcag cgcagacagg aagctccccg agataacgct      60
gcggccgggc ggcctgattt gctgggctgt ctgatggccc gggccgaggc ttctccctgc     120
gcctgggact gcggccgcct ctctaaatag cagccatgag gcgcctgggg gcagtgtcct     180
cgcggccgcg tcgaccgacg gccgcagtcg acgccccgtt cgcctagcgc gtgctcagga     240
gttggtgtcc tgcctgcgct cagg atg agg ggg aat ctg gcc ctg gtg ggc       291
                              Met Arg Gly Asn Leu Ala Leu Val Gly
                                1               5 gtt cta atc agc ctg gcc ttc ctg tca ctg ctg cca tct gga cat cct      339
Val Leu Ile Ser Leu Ala Phe Leu Ser Leu Leu Pro Ser Gly His Pro
 10              15                  20                  25 cag ccg gct ggc gat gac gcc tgc tct gtg cag atc ctc gtc cct ggc      387
Gln Pro Ala Gly Asp Asp Ala Cys Ser Val Gln Ile Leu Val Pro Gly
             30                  35                  40 ctc aaa ggg gat gcg gga gag aag gga gac aaa ggc gcc ccc gga cgg      435
Leu Lys Gly Asp Ala Gly Glu Lys Gly Asp Lys Gly Ala Pro Gly Arg
         45                  50                  55 cct gga aga gtc ggc ccc acg gga gaa aaa ggt gag aaa gga gat tcc      483
Pro Gly Arg Val Gly Pro Thr Gly Glu Lys Gly Glu Lys Gly Asp Ser
```

-continued

```
                60              65              70
ggt gac ata gga ccc cct ggt cct aat gga gaa cca ggc ctc cca tgt    531
Gly Asp Ile Gly Pro Pro Gly Pro Asn Gly Glu Pro Gly Leu Pro Cys
         75              80              85 gag tgc agc cag ctg cgc aag gcc atc ggg gag atg gac aac cag gtc    579
Glu Cys Ser Gln Leu Arg Lys Ala Ile Gly Glu Met Asp Asn Gln Val
 90              95             100             105 tct cag ctg acc agc gag ctc aag ttc atc aag aat gct gtc gcc ggt    627
Ser Gln Leu Thr Ser Glu Leu Lys Phe Ile Lys Asn Ala Val Ala Gly
                110             115             120 gtg cgc gag acg gag agc aag atc tac ctg ctg gtg aag gag gag aag    675
Val Arg Glu Thr Glu Ser Lys Ile Tyr Leu Leu Val Lys Glu Glu Lys
             125             130             135 cgc tac gcg gac gcc cag ctg tcc tgc cag ggc cgc ggg ggc acg ctg    723
Arg Tyr Ala Asp Ala Gln Leu Ser Cys Gln Gly Arg Gly Gly Thr Leu
         140             145             150 agc atg ccc aag gac gag gct gcc aat ggc ctg atg gcc gca tac ctg    771
Ser Met Pro Lys Asp Glu Ala Ala Asn Gly Leu Met Ala Ala Tyr Leu
     155             160             165 gcg caa gcc ggc ctg gcc cgt gtc ttc atc ggc atc aac gac ctg gag    819
Ala Gln Ala Gly Leu Ala Arg Val Phe Ile Gly Ile Asn Asp Leu Glu
170             175             180             185 aag gag ggc gcc ttc gtg tac tct gac cac tcc ccc atg cgg acc ttc    867
Lys Glu Gly Ala Phe Val Tyr Ser Asp His Ser Pro Met Arg Thr Phe
                190             195             200 aac aag tgg cgc agc ggt gag ccc aac aat gcc tac gac gag gag gac    915
Asn Lys Trp Arg Ser Gly Glu Pro Asn Asn Ala Tyr Asp Glu Glu Asp
             205             210             215 tgc gtg gag atg gtg gcc tcg ggc ggc tgg aac gac gtg gcc tgc cac    963
Cys Val Glu Met Val Ala Ser Gly Gly Trp Asn Asp Val Ala Cys His
         220             225             230 acc acc atg tac ttc atg tgt gag ttt gac aag gag aac atg           1005
Thr Thr Met Tyr Phe Met Cys Glu Phe Asp Lys Glu Asn Met
     235             240             245 tgagcctcag gctggggctg cccattgggg gccccacatg tccctgcagg gttggcaggg   1065
acagagccca gaccatggtg ccagccaggg agctgtccct ctgtgaaggg tggaggctca   1125
ctgagtagag ggctgttgtc taaactgaga aaatggccta tgcttaagag gaaaatgaaa   1185
gtgttcctgg ggtgctgtct ctgaagaagc agagtttcat tacctgtatt gtagccccaa   1245
tgtcattatg taattattac ccag                                         1269

<210> SEQ ID NO 41
<211> LENGTH: 247
<212> TYPE: PRT
<213> ORGANISM: Homo Sapiens
<220> FEATURE:
<223> OTHER INFORMATION: Deduced Amino Acid Sequence of Novel Collectin
      variant from Nucleotide Sequence set out in SEQ ID NO:40.

<400> SEQUENCE: 41

Met Arg Gly Asn Leu Ala Leu Val Gly Val Leu Ile Ser Leu Ala Phe
 1               5                  10                  15

Leu Ser Leu Leu Pro Ser Gly His Pro Gln Pro Ala Gly Asp Asp Ala
             20                  25                  30

Cys Ser Val Gln Ile Leu Val Pro Gly Leu Lys Gly Asp Ala Gly Glu
         35                  40                  45

Lys Gly Asp Lys Gly Ala Pro Gly Arg Pro Gly Arg Val Gly Pro Thr
     50                  55                  60

Gly Glu Lys Gly Glu Lys Gly Asp Ser Gly Asp Ile Gly Pro Pro Gly
```

```
                65                  70                  75                  80
Pro Asn Gly Glu Pro Gly Leu Pro Cys Glu Cys Ser Gln Leu Arg Lys
                85                  90                  95

Ala Ile Gly Glu Met Asp Asn Gln Val Ser Gln Leu Thr Ser Glu Leu
            100                 105                 110

Lys Phe Ile Lys Asn Ala Val Ala Gly Val Arg Glu Thr Glu Ser Lys
            115                 120                 125

Ile Tyr Leu Leu Val Lys Glu Lys Arg Tyr Ala Asp Ala Gln Leu
        130                 135                 140

Ser Cys Gln Gly Arg Gly Gly Thr Leu Ser Met Pro Lys Asp Glu Ala
145                 150                 155                 160

Ala Asn Gly Leu Met Ala Ala Tyr Leu Ala Gln Ala Gly Leu Ala Arg
            165                 170                 175

Val Phe Ile Gly Ile Asn Asp Leu Glu Lys Glu Gly Ala Phe Val Tyr
            180                 185                 190

Ser Asp His Ser Pro Met Arg Thr Phe Asn Lys Trp Arg Ser Gly Glu
            195                 200                 205

Pro Asn Asn Ala Tyr Asp Glu Glu Asp Cys Val Glu Met Val Ala Ser
        210                 215                 220

Gly Gly Trp Asn Asp Val Ala Cys His Thr Thr Met Tyr Phe Met Cys
225                 230                 235                 240

Glu Phe Asp Lys Glu Asn Met
                245

<210> SEQ ID NO 42
<211> LENGTH: 48
<212> TYPE: PRT
<213> ORGANISM: Homo Sapiens
<220> FEATURE:
<223> OTHER INFORMATION: Deduced Amino Acid Sequence of a collagen-like
      domain of mutated Novel Collectin.

<400> SEQUENCE: 42

Gly Leu Lys Gly Asp Met Gly Asp Lys Gly Gln Lys Gly Ser Val Gly
  1               5                  10                  15

Arg His Gly Lys Ile Gly Pro Ile Gly Ser Lys Gly Glu Lys Gly Asp
             20                  25                  30

Ser Gly Asp Ile Gly Pro Pro Gly Pro Asn Gly Glu Pro Gly Leu Pro
         35                  40                  45

<210> SEQ ID NO 43
<211> LENGTH: 24
<212> TYPE: PRT
<213> ORGANISM: Homo Sapiens
<220> FEATURE:
<223> OTHER INFORMATION: Deduced Amino Acid Sequence of a collagen-like
      domain of mutated Novel Collectin.

<400> SEQUENCE: 43

Gly Leu Lys Gly Glu Lys Gly Asp Ser Gly Asp Ile Gly Pro Pro Gly
  1               5                  10                  15

Pro Asn Gly Glu Pro Gly Leu Pro
             20

<210> SEQ ID NO 44
<211> LENGTH: 48
<212> TYPE: PRT
<213> ORGANISM: Homo Sapiens
<220> FEATURE:
<223> OTHER INFORMATION: Deduced Amino Acid Sequence of a collagen-like
      domain of mutated Novel Collectin.
```

<400> SEQUENCE: 44

Gly Leu Lys Gly Asp Ala Gly Glu Lys Gly Asp Lys Gly Ala Pro Gly
 1               5                  10                  15

Arg Pro Gly Arg Val Gly Pro Thr Gly Glu Lys Gly Glu Lys Gly Asp
            20                  25                  30

Ser Gly Asp Ile Gly Pro Pro Gly Pro Asn Gly Glu Pro Gly Leu Pro
        35                  40                  45

<210> SEQ ID NO 45
<211> LENGTH: 813
<212> TYPE: DNA
<213> ORGANISM: Homo Sapiens

<400> SEQUENCE: 45

```
atgaggggga atctggccct ggtgggcgtt ctaatcagcc tggccttcct gtcactgctg      60
ccatctggac atcctcagcc ggctggcgat gacgcctgct ctgtgcagat cctcgtccct     120
ggcctcaaag gggatgcggg agagaaggga gacaaaggcg ccccggacg gcctggaaga      180
gtcggcccca cggagaaaa aggagacatg ggggacaaag gacagaaagg cagtgtgggt     240
cgtcatggaa aaattggtcc cattggctct aaaggtgaga aggagattc cggtgacata      300
ggacccctg gtcctaatgg agaaccaggc ctcccatgtg agtgcagcca gctgcgcaag     360
gccatcgggg agatggacaa ccaggtctct cagctgacca gcgagctcaa gttcatcaag     420
aatgctgtcg ccggtgtgcg cgagacggag agcaagatct acctgctggt gaaggaggag     480
aagcgctacg cggacgccca gctgtcctgc agggccgcg ggggcacgct gagcatgccc      540
aaggacgagg ctgccaatgg cctgatggcc gcatacctgg cgcaagccgg cctggcccgt     600
gtcttcatcg gcatcaacga cctggagaag gagggcgcct tcgtgtactc tgaccactcc     660
cccatgcgga ccttcaacaa gtggcgcagc ggtgagccca caatgccta cgacgaggag     720
gactgcgtgg agatggtggc ctcgggcggc tggaacgacg tggcctgcca caccaccatg     780
tacttcatgt gtgagtttga caaggagaac atg                                 813
```

<210> SEQ ID NO 46
<211> LENGTH: 735
<212> TYPE: DNA
<213> ORGANISM: Homo Sapiens

<400> SEQUENCE: 46

```
atgtggtggg tgcctccgag tccctacggt tgtcttccct gcgccctgcc aggggatgcg      60
ggagagaagg gagacaaagg cgcccccgga cggcctggaa gagtcggccc acgggagaa     120
aaggagacag tggggacaa aggacagaaa ggcagtgtgg gtcgtcatgg aaaaattggt      180
cccattggct ctaaaggtga aaggagat ccggtgaca taggacccc tggtcctaat        240
ggagaaccag gcctcccatg tgagtgcagc cagctgcgca aggccatcgg ggagatggac     300
aaccaggtct ctcagctgac cagcgagctc aagttcatca gaatgctgt cgccggtgtg     360
cgcgagacgg agagcaagat ctacctgctg gtgaaggagg agaagcgcta cgcggacgcc     420
cagctgtcct gccagggccg cggggcacg ctgagcatgc caaggacga ggctgccaat      480
ggcctgatgg ccgcatacct ggcgcaagcc ggcctggccc gtgtcttcat cggcatcaac     540
gacctggaga aggagggcgc cttcgtgtac tctgaccact cccccatgcg gaccttcaac     600
aagtggcgca gcggtgagcc caacaatgcc tacgacgagg aggactgcgt ggagatggtg     660
gcctcgggcg gctggaacga cgtggcctgc cacaccacca tgtacttcat gtgtgagttt     720
```

```
gacaaggaga acatg                                                   735
```

```
<210> SEQ ID NO 47
<211> LENGTH: 159
<212> TYPE: PRT
<213> ORGANISM: Homo Sapiens

<400> SEQUENCE: 47
```

```
Cys Glu Cys Ser Gln Leu Arg Lys Ala Ile Gly Glu Met Asp Asn Gln
  1               5                  10                  15

Val Ser Gln Leu Thr Ser Glu Leu Lys Phe Ile Lys Asn Ala Val Ala
                 20                  25                  30

Gly Val Arg Glu Thr Glu Ser Lys Ile Tyr Leu Leu Val Lys Glu Glu
             35                  40                  45

Lys Arg Tyr Ala Asp Ala Gln Leu Ser Cys Gln Gly Arg Gly Gly Thr
 50                  55                  60

Leu Ser Met Pro Lys Asp Glu Ala Ala Asn Gly Leu Met Ala Ala Tyr
 65                  70                  75                  80

Leu Ala Gln Ala Gly Leu Ala Arg Val Phe Ile Gly Ile Asn Asp Leu
                 85                  90                  95

Glu Lys Glu Gly Ala Phe Val Tyr Ser Asp His Ser Pro Met Arg Thr
            100                 105                 110

Phe Asn Lys Trp Arg Ser Gly Glu Pro Asn Asn Ala Tyr Asp Glu Glu
        115                 120                 125

Asp Cys Val Glu Met Val Ala Ser Gly Gly Trp Asn Asp Val Ala Cys
    130                 135                 140

His Thr Thr Met Tyr Phe Met Cys Glu Phe Asp Lys Glu Asn Met
145                 150                 155
```

```
<210> SEQ ID NO 48
<211> LENGTH: 477
<212> TYPE: DNA
<213> ORGANISM: Homo Sapiens

<400> SEQUENCE: 48
tgtgagtgca gccagctgcg caaggccatc ggggagatgg acaaccaggt ctctcagctg    60
accagcgagc tcaagttcat caagaatgct gtcgccggtg tgcgcgagac ggagagcaag   120
atctacctgc tggtgaagga ggagaagcgc tacgcggacg cccagctgtc ctgccagggc   180
cgcgggggca cgctgagcat gcccaaggac gaggctgcca atggcctgat ggccgcatac   240
ctggcgcaag ccggcctggc ccgtgtcttc atcggcatca acgacctgga aaggagggc    300 gccttcgtgt actctgacca ctcccccatg cggaccttca acaagtggcg cagcggtgag   360
cccaacaatg cctacgacga ggaggactgc gtggagatgg tggcctcggg cggctggaac   420
gacgtggcct gccacaccac catgtacttc atgtgtgagt ttgacaagga gaacatg      477
```

```
<210> SEQ ID NO 49
<211> LENGTH: 72
<212> TYPE: PRT
<213> ORGANISM: Homo Sapiens

<400> SEQUENCE: 49
```

```
Gly Leu Lys Gly Asp Ala Gly Glu Lys Gly Asp Lys Gly Ala Pro Gly
  1               5                  10                  15

Arg Pro Gly Arg Val Gly Pro Thr Gly Glu Lys Gly Asp Met Gly Asp
                 20                  25                  30

Lys Gly Gln Lys Gly Ser Val Gly Arg His Gly Lys Ile Gly Pro Ile
             35                  40                  45
```

```
Gly Ser Lys Gly Glu Lys Gly Asp Ser Gly Asp Ile Gly Pro Pro Gly
    50                  55                  60

Pro Asn Gly Glu Pro Gly Leu Pro
 65                  70

<210> SEQ ID NO 50
<211> LENGTH: 69
<212> TYPE: PRT
<213> ORGANISM: Homo Sapiens

<400> SEQUENCE: 50

Gly Asp Ala Gly Glu Lys Gly Asp Lys Gly Ala Pro Gly Arg Pro Gly
 1               5                  10                  15

Arg Val Gly Pro Thr Gly Glu Lys Gly Asp Met Gly Asp Lys Gly Gln
                20                  25                  30

Lys Gly Ser Val Gly Arg His Gly Lys Ile Gly Pro Ile Gly Ser Lys
            35                  40                  45

Gly Glu Lys Gly Asp Ser Gly Asp Ile Gly Pro Pro Gly Pro Asn Gly
        50                  55                  60

Glu Pro Gly Leu Pro
 65

<210> SEQ ID NO 51
<211> LENGTH: 21
<212> TYPE: PRT
<213> ORGANISM: Homo Sapiens

<400> SEQUENCE: 51

Gly Glu Lys Gly Asp Ser Gly Asp Ile Gly Pro Pro Gly Pro Asn Gly
 1               5                  10                  15

Glu Pro Gly Leu Pro
                20

<210> SEQ ID NO 52
<211> LENGTH: 45
<212> TYPE: PRT
<213> ORGANISM: Homo Sapiens

<400> SEQUENCE: 52

Gly Asp Met Gly Asp Lys Gly Gln Lys Gly Ser Val Gly Arg His Gly
 1               5                  10                  15

Lys Ile Gly Pro Ile Gly Ser Lys Gly Glu Lys Gly Asp Ser Gly Asp
                20                  25                  30

Ile Gly Pro Pro Gly Pro Asn Gly Glu Pro Gly Leu Pro
            35                  40                  45

<210> SEQ ID NO 53
<211> LENGTH: 40
<212> TYPE: PRT
<213> ORGANISM: Homo Sapiens

<400> SEQUENCE: 53

Met Arg Gly Asn Leu Ala Leu Val Gly Val Leu Ile Ser Leu Ala Phe
 1               5                  10                  15

Leu Ser Leu Leu Pro Ser Gly His Pro Gln Pro Ala Gly Asp Asp Ala
                20                  25                  30

Cys Ser Val Gln Ile Leu Val Pro
            35                  40

<210> SEQ ID NO 54
```

```
<211> LENGTH: 17
<212> TYPE: PRT
<213> ORGANISM: Homo Sapiens

<400> SEQUENCE: 54

Met Trp Trp Val Pro Pro Ser Pro Tyr Gly Cys Leu Pro Cys Ala Leu
 1               5                  10                  15

Pro

<210> SEQ ID NO 55
<211> LENGTH: 591
<212> TYPE: DNA
<213> ORGANISM: Homo Sapiens

<400> SEQUENCE: 55
atgtggtggg tgcctccgag tccctacggt tgtcttccct gcgccctgcc aggtgagaaa    60
ggagattccg gtgacatagg accccctggt cctaatggag aaccaggcct cccatgtgag   120
tgcagccagc tgcgcaaggc catcggggag atggacaacc aggtctctca gctgaccagc   180
gagctcaagt tcatcaagaa tgctgtcgcc ggtgtgcgcg agacggagag caagatctac   240
ctgctggtga aggaggagaa agcgctacgc gacgcccagc tgtcctgcca gggccgcggg   300
ggcacgctga gcatgcccaa ggacgaggct gccaatggcc tgatggccgc atacctggcg   360
caagccggcc tggcccgtgt cttcatcggc atcaacgacc tggagaagga gggcgccttc   420
gtgtactctg accactcccc catgcggacc ttcaacaagt ggcgcagcgg tgagcccaac   480
aatgcctacg acgaggagga ctgcgtggag atggtggcct cgggcggctg aacgacgtg    540 gcctgccaca ccaccatgta cttcatgtgt gagtttgaca aggagaacat g            591

<210> SEQ ID NO 56
<211> LENGTH: 663
<212> TYPE: DNA
<213> ORGANISM: Homo Sapiens

<400> SEQUENCE: 56
atgtggtggg tgcctccgag tccctacggt tgtcttccct gcgccctgcc aggagacatg    60
ggggacaaag gacagaaagg cagtgtgggt cgtcatggaa aaattggtcc cattggctct   120
aaaggtgaga aggagattc cggtgacata ggaccccctg gtcctaatgg agaaccaggc    180
ctcccatgtg agtgcagcca gctgcgcaag gccatcgggg agatggacaa ccaggtctct   240
cagctgacca gcgagctcaa gttcatcaag aatgctgtcg ccggtgtgcg cgagacggag   300
agcaagatct acctgctggt gaaggaggag aagcgctacg cggacgccca gctgtcctgc   360
cagggccgcg ggggcacgct gagcatgccc aaggacgagg ctgccaatgg cctgatggcc   420
gcatacctgg cgcaagccgg cctggcccgt gtcttcatcg gcatcaacga cctggagaag   480
gagggcgcct cgtgtactc tgaccactcc cccatgcgga ccttcaacaa gtggcgcagc   540
ggtgagccca caatgccta cgacgaggag gactgcgtgg agatggtggc ctcgggcggc   600
tggaacgacg tggcctgcca caccaccatg tacttcatgt gtgagtttga caaggagaac   660
atg                                                                  663

<210> SEQ ID NO 57
<211> LENGTH: 663
<212> TYPE: DNA
<213> ORGANISM: Homo Sapiens

<400> SEQUENCE: 57
atgtggtggg tgcctccgag tccctacggt tgtcttccct gcgccctgcc agggatgcg    60
```

```
ggagagaagg gagacaaagg cgcccccgga cggcctggaa gagtcggccc cacgggagaa    120
aaaggtgaga aaggagattc cggtgacata ggaccccctg gtcctaatgg agaaccaggc    180
ctcccatgtg agtgcagcca gctgcgcaag gccatcgggg agatggacaa ccaggtctct    240
cagctgacca gcgagctcaa gttcatcaag aatgctgtcg ccggtgtgcg cgagacggag    300
agcaagatct acctgctggt gaaggaggag aagcgctacg cggacgccca gctgtcctgc    360
cagggccgcg ggggcacgct gagcatgccc aaggacgagg ctgccaatgg cctgatggcc    420
gcatacctgg cgcaagccgg cctggcccgt gtcttcatcg gcatcaacga cctggagaag    480
gagggcgcct tcgtgtactc tgaccactcc cccatgcgga ccttcaacaa gtggcgcagc    540
ggtgagccca acaatgccta cgacgaggag gactgcgtgg agatggtggc ctcgggcggc    600
tggaacgacg tggcctgcca caccaccatg tacttcatgt gtgagtttga caaggagaac    660
atg                                                                  663

<210> SEQ ID NO 58
<211> LENGTH: 813
<212> TYPE: DNA
<213> ORGANISM: Mus musculus

<400> SEQUENCE: 58
atgatgaggg acctggctct tgcaggcatg ctgattagcc tggctttcct gtccctgctg     60
ccatctggat gtcctcagca gaccacagag gacgcctgct ctgtgcagat tcttgtcccc    120
ggcctcaaag gggatgcagg agaaaaggga gacaaaggag ccccaggacg gccaggaaga    180
gtcggcccta caggagaaaa aggagacatg ggggacaaag gacagaaagg cactgtgggc    240
cgccatggaa aaattggtcc cattggcgca aaaggtgaaa aaggagattc tggtgatatc    300
ggaccccctg gccccagtgg agaacctggt attccatgtg agtgcagtca gctgaggaag    360
gctattgggg agatggacaa ccaggtcact caactgacaa ctgagctaaa attcataaaa    420
aatgctgttg ctggcgtgcg cgagactgag agcaagatct acctgctggt gaaggaggag    480
aagcggtacg cagatgccca gctgtcctgc aagcccgag gcggcacact gagcatgccc    540
aaagacgagg cagccaatgg cctgatggct tcatacctgg cacaggctgg cctggcccga    600
gtcttcatcg gtatcaatga cctggagaaa gaaggtgctt tcgtgtactc ggaccgctcc    660
cccatgcaga ccttcaacaa gtggcgcagt ggagagccca caacgcctg tgatgaggag    720 gactgtgtgg agatggtggc ctcaggtggc tggaatgatg tggcctgcca cattaccatg    780
tacttcatgt gcgagtttga caaagagaac ttg                                 813

<210> SEQ ID NO 59
<211> LENGTH: 669
<212> TYPE: DNA
<213> ORGANISM: Homo Sapiens

<400> SEQUENCE: 59
atgaggggga atctggccct ggtgggcgtt ctaatcagcc tggccttcct gtcactgctg     60
ccatctggac atcctcagcc ggctggcgat acgcctgct ctgtgcagat cctcgtccct    120
ggcctcaaag gtgagaaagg agattccggt gacataggac ccctggtcc taatggagaa    180 ccaggcctcc catgtgagtg cagccagctg cgcaaggcca tcggggagat ggacaaccag    240
gtctctcagc tgaccagcga gctcaagttc atcaagaatg ctgtcgccgg tgtgcgcgag    300
acggagagca gatctaccct gctggtgaag gaggagaagc gctacgcgga cgcccagctg    360
tcctgccagg gccgcggggg cacgctgagc atgcccaagg acgaggctgc caatggcctg    420
```

```
atggccgcat acctggcgca agccggcctg gcccgtgtct tcatcggcat caacgacctg      480
gagaaggagg gcgccttcgt gtactctgac cactccccca tgcggacctt caacaagtgg      540
cgcagcggtg agcccaacaa tgcctacgac gaggaggact gcgtggagat ggtggcctcg      600
ggcggctgga acgacgtggc ctgccacacc accatgtact tcatgtgtga gtttgacaag      660
gagaacatg                                                              669
```

<210> SEQ ID NO 60
<211> LENGTH: 741
<212> TYPE: DNA
<213> ORGANISM: Homo Sapiens

<400> SEQUENCE: 60

```
atgaggggga atctggccct ggtgggcgtt ctaatcagcc tggccttcct gtcactgctg       60
ccatctggac atcctcagcc ggctggcgat gacgcctgct ctgtgcagat cctcgtccct      120
ggcctcaaag gagacatggg ggacaaagga cagaaaggca gtgtgggtcg tcatggaaaa      180
attggtccca ttggctctaa aggtgagaaa ggagattccg gtgacatagg acccccctggt    240 cctaatggag aaccaggcct cccatgtgag tgcagccagc tgcgcaaggc catcggggag      300
atggacaacc aggtctctca gctgaccagc gagctcaagt tcatcaagaa tgctgtcgcc      360
ggtgtgcgcg agacggagag caagatctac ctgctggtga aggaggagaa gcgctacgcg      420
gacgcccagc tgtcctgcca gggccgcggg gcacgctga gcatgcccaa ggacgaggct       480
gccaatggcc tgatggccgc atacctggcg caagccggcc tggcccgtgt cttcatcggc      540
atcaacgacc tggagaagga gggcgccttc gtgtactctg accactcccc catgcggacc      600
ttcaacaagt ggcgcagcgg tgagcccaac aatgcctacg acgaggagga ctgcgtggag      660
atggtggcct cgggcggctg gaacgacgtg gcctgccaca ccaccatgta cttcatgtgt      720
gagtttgaca aggagaacat g                                                741
```

<210> SEQ ID NO 61
<211> LENGTH: 741
<212> TYPE: DNA
<213> ORGANISM: Homo Sapiens

<400> SEQUENCE: 61

```
atgaggggga atctggccct ggtgggcgtt ctaatcagcc tggccttcct gtcactgctg       60
ccatctggac atcctcagcc ggctggcgat gacgcctgct ctgtgcagat cctcgtccct      120
ggcctcaaag gggatgcggg agagaaggga gacaaaggcg cccccggacg gcctggaaga     180
gtcggcccca cgggagaaaa aggtgagaaa ggagattccg gtgacatagg acccccctggt    240 cctaatggag aaccaggcct cccatgtgag tgcagccagc tgcgcaaggc catcggggag      300
atggacaacc aggtctctca gctgaccagc gagctcaagt tcatcaagaa tgctgtcgcc      360
ggtgtgcgcg agacggagag caagatctac ctgctggtga aggaggagaa gcgctacgcg      420
gacgcccagc tgtcctgcca gggccgcggg gcacgctga gcatgcccaa ggacgaggct       480
gccaatggcc tgatggccgc atacctggcg caagccggcc tggcccgtgt cttcatcggc      540
atcaacgacc tggagaagga gggcgccttc gtgtactctg accactcccc catgcggacc      600
ttcaacaagt ggcgcagcgg tgagcccaac aatgcctacg acgaggagga ctgcgtggag      660
atggtggcct cgggcggctg gaacgacgtg gcctgccaca ccaccatgta cttcatgtgt      720
gagtttgaca aggagaacat g                                                741
```